United States Patent
Tani et al.

(10) Patent No.: US 9,953,768 B2
(45) Date of Patent: Apr. 24, 2018

(54) METAL-COMPLEX DYE, PHOTOELECTRIC CONVERSION ELEMENT, DYE-SENSITIZED SOLAR CELL, AND DYE SOLUTION CONTAINING METAL-COMPLEX DYE

(71) Applicant: FUJIFILM Corporation, Minato-ku, Tokyo (JP)

(72) Inventors: Yukio Tani, Kanagawa (JP); Katsumi Kobayashi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 11 days.

(21) Appl. No.: 14/860,001

(22) Filed: Sep. 21, 2015

(65) Prior Publication Data

US 2016/0012977 A1    Jan. 14, 2016

Related U.S. Application Data

(63) Continuation of application No. PCT/JP2014/057892, filed on Mar. 20, 2014.

(30) Foreign Application Priority Data

Mar. 25, 2013  (JP) .................................. 2013-062890
Mar. 14, 2014  (JP) .................................. 2014-052685

(51) Int. Cl.
  *C09B 57/10*    (2006.01)
  *H01L 51/50*    (2006.01)
  (Continued)

(52) U.S. Cl.
  CPC ....... *H01G 9/2059* (2013.01); *C07F 15/0026* (2013.01); *C07F 15/0053* (2013.01);
  (Continued)

(58) Field of Classification Search
  None
  See application file for complete search history.

(56) References Cited

U.S. PATENT DOCUMENTS

2008/0210296 A1  9/2008  Morooka et al.
2010/0258175 A1  10/2010 Chi et al.
(Continued)

FOREIGN PATENT DOCUMENTS

CN     102015908 A    4/2011
EP     2551951 A1     1/2013
(Continued)

OTHER PUBLICATIONS

Bo-So Chen et al, "Neutral, panchromatic Ru(II) terpyridine sensitizers bearing pyridine pyrazolate chelates with superior DSSC performance", Chemical Communications, 2009, p. 5844-5846.
(Continued)

*Primary Examiner* — Katie L Hammer
(74) *Attorney, Agent, or Firm* — Sughrue Mion, PLLC

(57) ABSTRACT

A photoelectric conversion element, a photoelectric conversion element, a dye-sensitized solar cell and a dye solution, having an electrically conductive support, a photoconductor layer containing an electrolyte, a charge transfer layer containing an electrolyte, and a counter electrode, wherein the photoconductor layer contains semiconductor fine particles carrying a metal complex dye; and wherein the metal complex dye has at least a carboxyl group and a salt of the carboxyl group, the salt being selected from the group consisting of a potassium salt, a lithium salt, and a cesium salt, and the ratio α of the number of the salt of the carboxyl group divided by the total number of the carboxyl group and the salt of the carboxyl group to be found in one molecule of the metal complex dye, lying in the range of 0.1 to 0.9.

22 Claims, 1 Drawing Sheet

(51) Int. Cl.
*H01G 9/20* (2006.01)
*C07F 15/00* (2006.01)
*H01L 51/00* (2006.01)
*C09B 23/01* (2006.01)
*C09B 23/10* (2006.01)
*C09B 23/14* (2006.01)

(52) U.S. Cl.
CPC .......... *C09B 23/005* (2013.01); *C09B 23/105* (2013.01); *C09B 23/145* (2013.01); *C09B 57/10* (2013.01); *H01L 51/0086* (2013.01); *H01L 51/0088* (2013.01); *Y02E 10/542* (2013.01); *Y02E 10/549* (2013.01)

(56) References Cited

U.S. PATENT DOCUMENTS

| | | | |
|---|---|---|---|
| 2011/0155238 A1* | 6/2011 | Shen | C07F 15/002 136/256 |
| 2012/0073660 A1 | 3/2012 | Chi et al. | |
| 2012/0111410 A1 | 5/2012 | Chi et al. | |

FOREIGN PATENT DOCUMENTS

| | | |
|---|---|---|
| JP | 2006-252986 A | 9/2006 |
| JP | 2007-141473 A | 6/2007 |
| JP | 2008-192546 A | 8/2008 |
| JP | 2012-036237 A | 2/2012 |
| JP | 2012-216496 A | 11/2012 |
| WO | 2013/047614 A1 | 4/2013 |
| WO | 2013/047615 A1 | 4/2013 |
| WO | 2013/088898 A1 | 6/2013 |
| WO | 2013/118709 A1 | 8/2013 |

OTHER PUBLICATIONS

Cristina Sens et al, Synthesis, Structure, and Acid-Base and Redox Properties of a Family of New Ru(II) Isomeric Complexes Containing the Trpy and the Dinucleating Hbpp Ligands, Inorganic Chemistry, vol. 42, No. 25, 2003, pp. 8385-8394.
Extended European Search Report dated May 3, 2016 in corresponding European Application No. 14775287.7.
Communication dated May 10, 2016, from the Japanese Patent Office in counterpart application No. 2014-052685.
International Search Report for PCT/JP2014/057892 dated Jun. 17, 2014.
Communication dated Oct. 24, 2017 from the Taiwanese Intellectual Property Office in counterpart Application No. 103110959.

* cited by examiner

{Fig. 1}
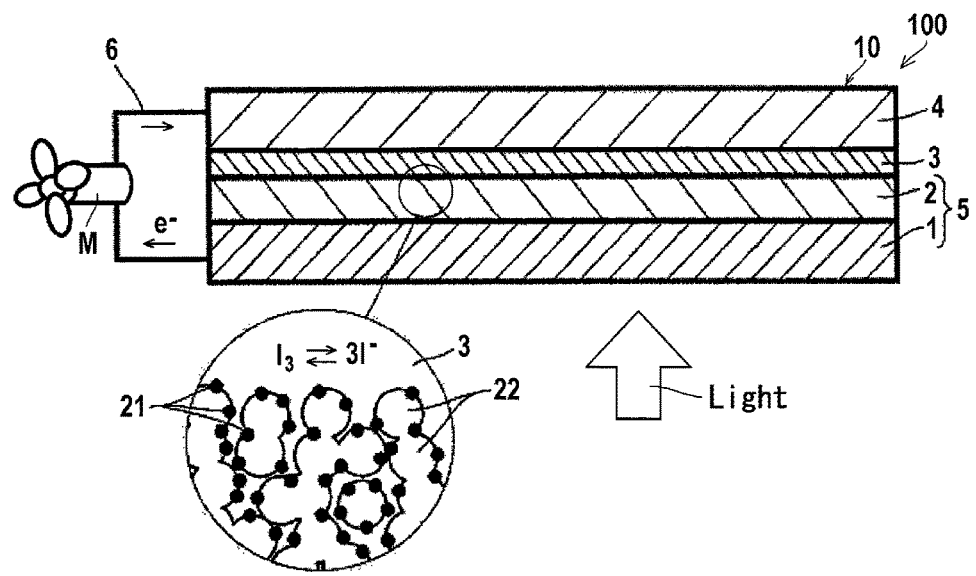
{Fig. 2}
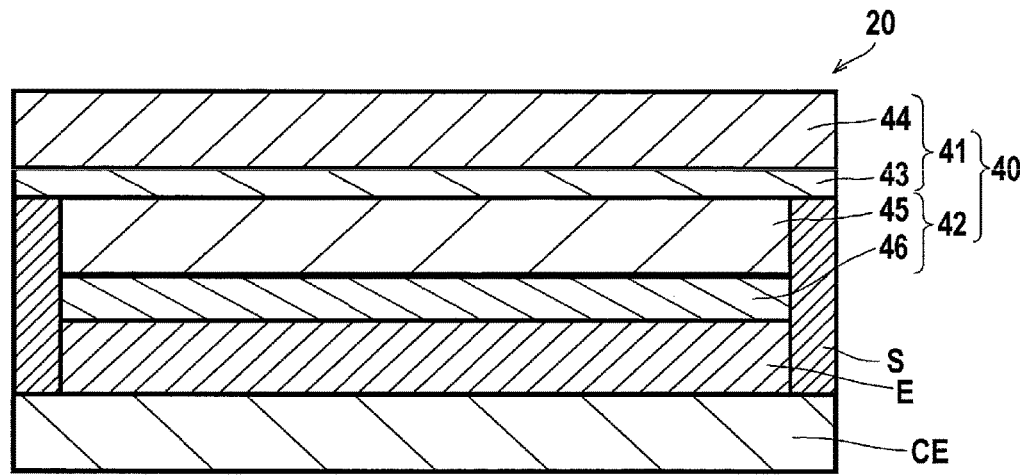

METAL-COMPLEX DYE, PHOTOELECTRIC CONVERSION ELEMENT, DYE-SENSITIZED SOLAR CELL, AND DYE SOLUTION CONTAINING METAL-COMPLEX DYE

CROSS-REFERENCE TO RELATED APPLICATIONS

This application is a Continuation of PCT International Application No. PCT/JP2014/057892 filed on Mar. 20, 2014, which claims priority under 35 U.S.C. § 119 (a) to Japanese Patent Application No. 2013-062890 filed in Japan on Mar. 25, 2013, and Patent Application No. 2014-052685 filed in Japan on Mar. 14, 2014. Each of the above applications is hereby expressly incorporated by reference, in its entirety, into the present application.

TECHNICAL FIELD

The present invention relates to a metal complex dye, a photoelectric conversion element, a dye-sensitized solar cell, and a dye solution containing a metal complex dye.

BACKGROUND ART

Photoelectric conversion elements are used in various photosensors, copying machines, solar cells, and the like. These photoelectric conversion elements have adopted various systems to be put into use, such as elements utilizing metals, elements utilizing semiconductors, elements utilizing organic pigments or dyes, or combinations of these elements. In particular, solar cells using non-exhaustive solar energy do not necessitate fuels, and besides can utilize an inexhaustible clean energy; full-fledged implementation thereof is being highly expected. Among these, research and development of silicon-based solar cells have long been in progress. Many countries support the silicon-based solar cells in policy-wise considerations, and thus they are progressively prevailed. However, silicon is an inorganic material, and hence it has its own limitations in terms of improving throughput, cost, and the like.

Under such circumstances, research is being vigorously carried out on dye-sensitized solar cells. Especially, the research results by Graetzel et al. of École Polytechnique Fédérale de Lausanne in Switzerland is recognized as a turning point. They employed a structure in which a dye formed from a ruthenium complex was fixed at the surface of a porous titanium oxide thin film, and realized a conversion efficiency that was comparable to that of amorphous silicon. Thus, the dye-sensitized solar cells that can be produced even without using an expensive vacuum apparatus instantly attracted the attention of researchers all over the world.

Hitherto, as metal complex dyes to be used in photoelectric conversion elements, dyes generally called as N3, N719, Z907, and J2 have been developed.

Recently, a Ru metal complex dye is proposed, having a particular substituent-having [4-styryl-2-(3-trifluoromethyl)-1H-pyrazole-5-yl] pyridine of a bidentate ligand and 4,4',4''-tricarboxy-terpyridine of a terdentate ligand (see Patent Literature 1). A novel metal complex is also proposed, having a particular 2,6-bis(nitrogen-containing aromatic ring) pyridine of a terdentate ligand and 4,4',4''-tricarboxy-terpyridine of a terdentate ligand (see Patent Literature 2).

Further, N719, Black Dye is proposed, having a carboxyl group neutralized with an alkali compound in order to prevent dye association, the carboxyl group playing as a roll of adsorbing it on the surface of semiconductor fine particles (see Patent Literature 3).

CITATION LIST

Patent Literatures

Patent Literature 1: US 2012/0111410
Patent Literature 2: US 2012/0073660
Patent Literature 3: JP-A-2006-252986 ("JP-A" means unexamined published Japanese patent application)

SUMMARY OF INVENTION

Technical Problem

As to the conventional metal complex dyes including those metal complex dyes described in Patent Literature 1 and Patent Literature 2, a greater upgrading or improvement are required in terms of increase in photoelectric conversion efficiencies and durability, compared to those of the solar cells using an inorganic material of silicon. The improvement in durability of organic material is particularly a difficult task, as its destiny, and it is hence important to find out a new angle of development of it. Further, the metal complex dyes described in Patent Literature 1 and Patent Literature 2 require a long time in order to adsorb the dye on the surface of semiconductor fine particles because solubility of the dye is too low. Since the reduction in productivity may directly cause to cost increases, the reduction of the adsorption time was required.

On the other hand, in Patent Literature 3, N719 and Black Dye are neutralized with an alkali compound to suppress a dye association, thereby increasing photoelectric conversion efficiencies. However, these dyes were not expected to make any further improvement to durability even by neutralizing them with the alkali compound because durability of these dyes is intrinsically low. As to these dyes, solubility in an electrolyte is too high because these dyes are hydrophilic, so that in the state of a cell, equilibrium between the state of adsorption on the semiconductor fine particles and the state of dissolution in the electrolyte is relatively deflected on the side of the electrolyte, and therefore desorption of the dye is easily caused, which results in low durability.

As mentioned above, ordinarily, the dye having excessively low solubility requires a long adsorption time and, in contrast, the dye having high solubility results in low durability, so that there exists a trade-off relationship between them. As a result, it was difficult to attain the both requirements simultaneously.

Therefore, the present invention addresses to the provision of a metal complex dye, a photoelectric conversion element, a dye-sensitized solar cell, and a dye solution containing the metal complex dye which have broken out of the above trade-off, thereby simultaneously attaining further improvement in durability and reduction in adsorption time.

Solution to Problem

As a result of detailed studies simultaneously to attain reduction in adsorption time and improvement in durability, the present inventors have found that although the dye association is also an important factor, rather another factor such as a relation to a dye adsorption on the surface of the semiconductor fine particles works in a coordination metal complex dye having a particular chemical structure that combined one terdentate ligand, one bidentate ligand and one monodentate ligand, compared to a metal complex dye that combined one terdentate ligand and three monodentate ligands like Black Dye, or a metal complex dye that combined two bidentate ligands and two monodentate ligands like N719.

Further, the present inventors have found that these findings are not expected from metal complex dyes having high hydrophilicity and high solubility like the Black Dye and the N719, but the analysis of physical and chemical factors of the metal complex dye is important.

As a result of studies conducted from the above viewpoints, the present invention has been made.

That is, the tasks of the present invention can be achieved by the following means.

(1) A photoelectric conversion element, having an electrically conductive support, a photoconductor layer containing an electrolyte, a charge transfer layer containing an electrolyte, and a counter electrode, wherein the photoconductor layer contains semiconductor fine particles carrying a metal complex dye represented by the following Formula (I); and wherein the metal complex dye has at least a carboxyl group and a salt of the carboxyl group, the salt being selected from the group consisting of a potassium salt, a lithium salt, and a cesium salt, and the ratio α of the number of the salt of the carboxyl group divided by the total number of the carboxyl group and the salt of the carboxyl group to be found in one molecule of the metal complex dye, lying in the range of 0.1 to 0.9:

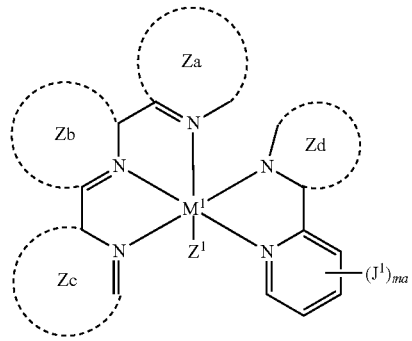

Formula (I)

wherein, in Formula (I), $M^1$ represents a Ru atom or an Os atom; $Z^1$ represents a monodentate ligand; the rings Za, Zb and Zc each independently represent a group of nonmetallic atoms necessary for forming a nitrogen-containing 5- or 6-membered ring, provided that at least two rings among the rings formed by Za, Zb and Zc each contain a carboxyl group, or a potassium salt, a lithium salt or a cesium salt of a carboxyl group; the ring Zd represents a group represented by any one of the following Formulas (Zd-1) to (Zd-5); $J^1$ represents a substituent; and ma represents an integer of 0 to 2;

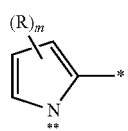

Formula (Zd-1)

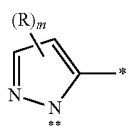

Formula (Zd-2)

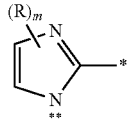

Formula (Zd-3)

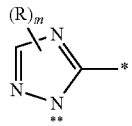

Formula (Zd-4)

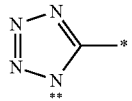

Formula (Zd-5)

wherein, in Formulas (Zd-1) to (Zd-5), R represents an alkyl group which may be substituted with a halogen atom, an aromatic group, or a heterocyclic group; m represents an integer of 0 or more; the symbol "*" represents a binding site with the pyridine ring having $J^1$; and the symbol "**" represents an atom or an atom anion coordinated with $M^1$.

(2) The photoelectric conversion element described in item (1), wherein, in Formula (I), when any two of rings formed as the ring Za, the ring Zb and the ring Zc have the carboxyl group, or the potassium salt, the lithium salt or the cesium salt of the carboxyl group, the ratio α is 0.15 to 0.55, and when all of rings formed as the ring Za, the ring Zb and the ring Zc have the carboxyl group, or the potassium salt, the lithium salt or the cesium salt of the carboxyl group, the ratio α is 0.1 to 0.7.

(3) The photoelectric conversion element described in item (1) or (2), wherein, in Formula (I), all of the rings formed as the ring Za, the ring Zb and the ring Zc have a carboxyl group, or a potassium salt, a lithium salt or a cesium salt of a carboxyl group; and the ratio α is 0.1 to 0.7.

(4) The photoelectric conversion element described in any one of items (1) to (3), wherein the ratio α is 0.2 to 0.5.

(5) The photoelectric conversion element described in any one of items (1) to (4), wherein the ratio α is 0.25 to 0.4.

(6) The photoelectric conversion element described in any one of items (1) to (5), wherein the metal complex dye is represented by the following Formula (I-1):

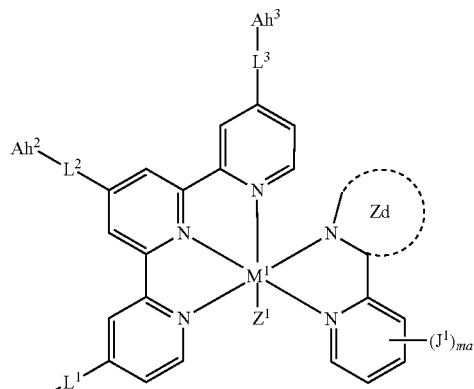

Formula (I-1)

wherein, in Formula (I-1), the ring Zd, $M^1$, $Z^1$, $J^1$ and ma have the same meaning as the ring Zd, $M^1$, $Z^1$, $J^1$ and ma in Formula (I); $L^1$ to $L^3$ each independently represent a single bond or a divalent linking group; $Ah^1$ to $Ah^3$ each independently represent a hydrogen atom, a carboxyl group, or a potassium salt, a lithium salt or a cesium salt of a carboxyl group; and at least two of $Ah^1$ to $Ah^3$ are a carboxyl group, or a potassium salt, a lithium salt or a cesium salt of a carboxyl group.

(7) The photoelectric conversion element described in any one of items (1) to (6), wherein the metal complex dye is represented by the following Formula (I-2):

Formula (I-2)

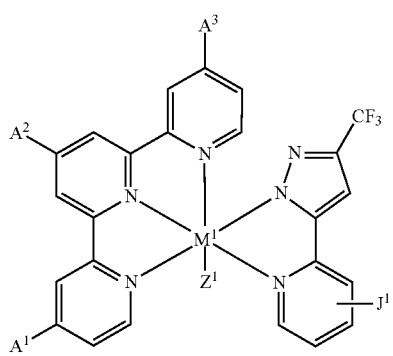

wherein, in Formula (I-2), $M^1$, $Z^1$ and $J^1$ have the same meaning as $M^1$, $Z^1$ and $J^1$ in Formula (I-1); $A^1$ to $A^3$ each independently represent a carboxyl group, or a potassium salt, a lithium salt or a cesium salt of a carboxyl group; and at least two of $A^1$ to $A^3$ are a carboxyl group, or a potassium salt, a lithium salt or a cesium salt of a carboxyl group.

(8) The photoelectric conversion element described in any one of items (1) to (7), wherein the metal complex dye is represented by any one of the following Formulas (I-3A) to (I-3C):

Formula (I-3A)

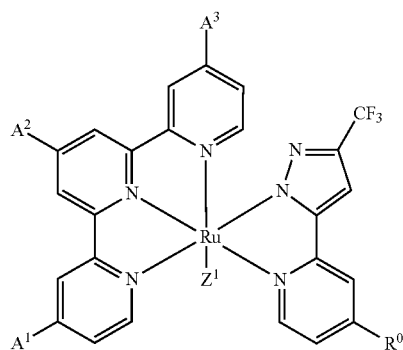

Formula (I-3B)

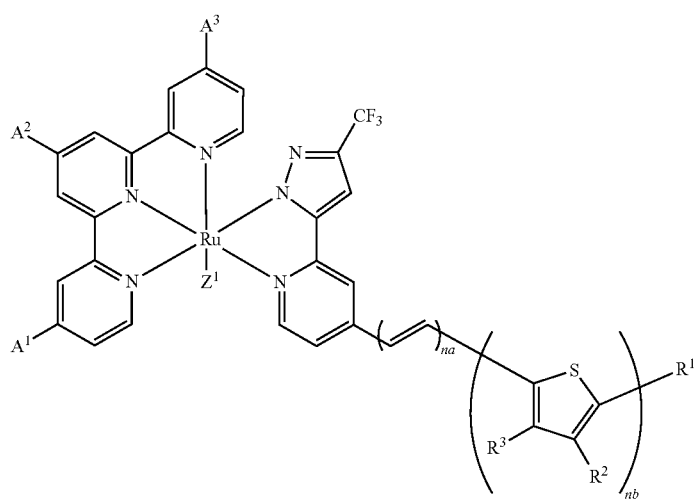

Formula (I-3C)

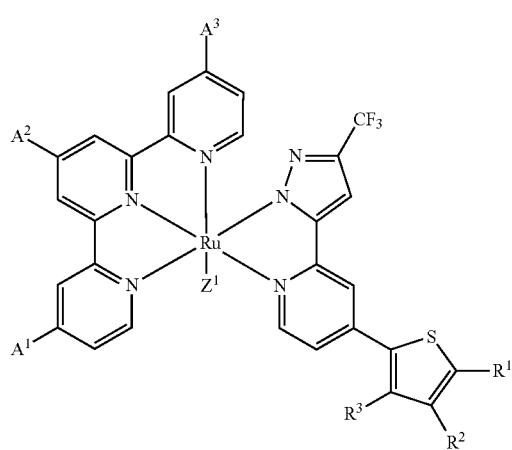

wherein, in Formulas (I-3A) to (I-3C), $Z^1$ has the same meaning as $Z^1$ in Formula (I); $A^1$ to $A^3$ each independently represent a carboxyl group, or a potassium salt, a lithium salt or a cesium salt of a carboxyl group; at least two of $A^1$ to $A^3$ are a carboxyl group, or a potassium salt, a lithium salt or a cesium salt of a carboxyl group; $R^0$ represents a hydrogen atom; $R^1$ represents a hydrogen atom, an alkyl group, an alkynyl group, an alkenyl group, an alkylthio group, an amino group or a heterocyclic group; $R^2$ and $R^3$ each independently represent a hydrogen atom, an alkyl group, an alkoxy group or a heterocyclic group; and na and nb each independently represent an integer of 0 or more, provided that the sum of na and nb is 2 or more.

(9) The photoelectric conversion element described in item (8), wherein, in Formula (I-3B), $R^1$ is an alkyl group, an alkynyl group, an amino group or an alkylthio group, and $R^2$ and $R^3$ each independently are a hydrogen atom or an alkoxy group.

(10) The photoelectric conversion element described in item (8), wherein, in Formula (I-3C), $R^1$ is an alkyl group, an alkynyl group or a heterocyclic group, and $R^2$ and $R^3$ are a hydrogen atom; or wherein, in Formula (I-3C), $R^1$ and $R^2$ are a hydrogen atom, and $R^3$ is an alkyl group.

(11) A photoelectric conversion element, having an electrically conductive support, a photoconductor layer containing an electrolyte, a charge transfer layer containing an electrolyte, and a counter electrode,
wherein the photoconductor layer contains semiconductor fine particles carrying a metal complex dye represented by the following Formula (IA):

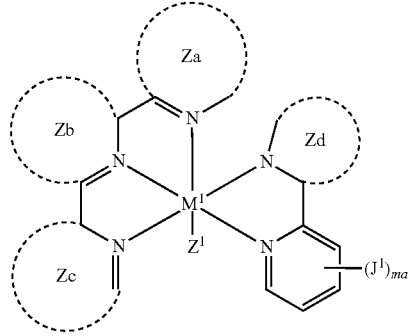

Formula (IA)

wherein, in Formula (IA), $M^1$ represents a Ru atom or an Os atom; $Z^1$ represents a monodentate ligand; the rings Za, Zb and Zc each independently represent a group of nonmetallic atoms necessary for forming a nitrogen-containing 5- or 6-membered ring, provided that at least two of rings formed as the rings Za, Zb and Zc have a carboxyl group, or a potassium salt, a lithium salt or a cesium salt of the carboxyl group, at least one thereof being the carboxyl group, and at least one of the remainder being the potassium salt, the lithium salt or the cesium salt of the carboxyl group; the ring Zd is represented by any one of the following Formulas (Zd-1) to (Zd-5); $J^1$ represents a substituent; and ma represents an integer of 0 to 2.

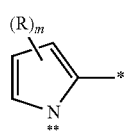

Formula (Zd-1)

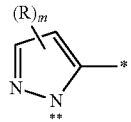

Formula (Zd-2)

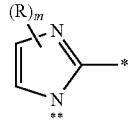

Formula (Zd-3)

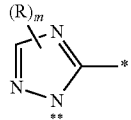

Formula (Zd-4)

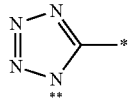

Formula (Zd-5)

wherein, in Formulas (Zd-1) to (Zd-5), R represents an alkyl group which may be substituted with a halogen atom, an aromatic group, or a heterocyclic group; m represents an integer of 0 or more; the symbol "*" represents a binding site with the pyridine ring having $J^1$; and the symbol "**" represents an atom or an atom anion coordinated with $M^1$.

(12) The photoelectric conversion element described in item (11), wherein the metal complex dye represented by Formula (IA) is represented by the following Formula (IA-1):

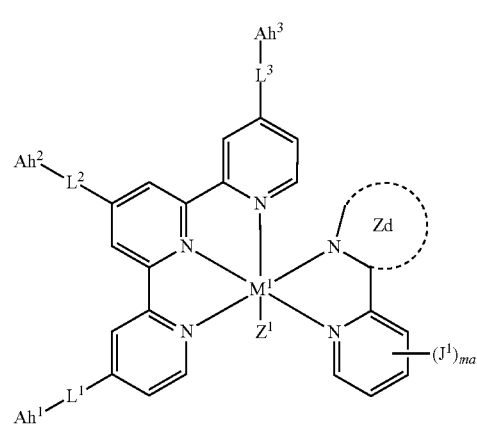

Formula (IA-1)

wherein, in Formula (IA-1), the ring Zd, $M^1$, $Z^1$, $J^1$ and ma have the same meaning as the ring Zd, $M^1$, $Z^1$, $J^1$ and ma in Formula (IA); $L^1$ to $L^3$ each independently represent a single bond or a divalent linking group; $Ah^1$ to $Ah^3$ each independently represent a hydrogen atom, a carboxyl group, or a potassium salt, a lithium salt or a cesium salt of a carboxyl group; and at least two of $Ah^1$ to $Ah^3$ are a carboxyl group, or a potassium salt, a lithium salt or a cesium salt of a carboxyl group.

(13) The photoelectric conversion element described in item (11) or (12), wherein the metal complex dye is represented by the following Formula (IA-2):

Formula (IA-2)

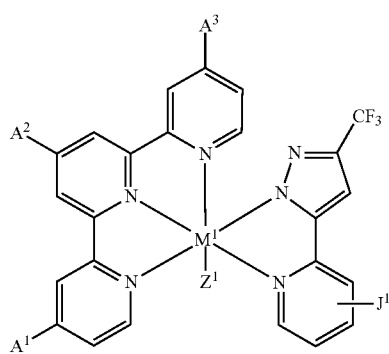

wherein, in Formula (IA-2), $M^1$, $Z^1$ and $J^1$ have the same meaning as $M^1$, $Z^1$ and $J^1$ in Formula (IA-1); $A^1$ to $A^3$ each independently represent a carboxyl group, or a potassium salt, a lithium salt or a cesium salt of a carboxyl group, provided that at least one of $A^1$ to $A^3$ represents a carboxyl group, and at least one of $A^1$ to $A^3$ represents a potassium salt, a lithium salt or a cesium salt of a carboxyl group.

(14) The photoelectric conversion element described in any one of items (11) to (13), wherein the metal complex dye is represented by any one of the following Formulas (IA-3A) to (IA-3C):

Formula (I-3A)

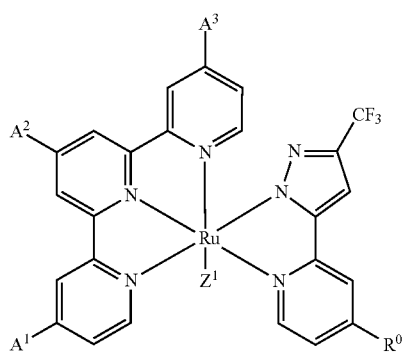

Formula (I-3B)

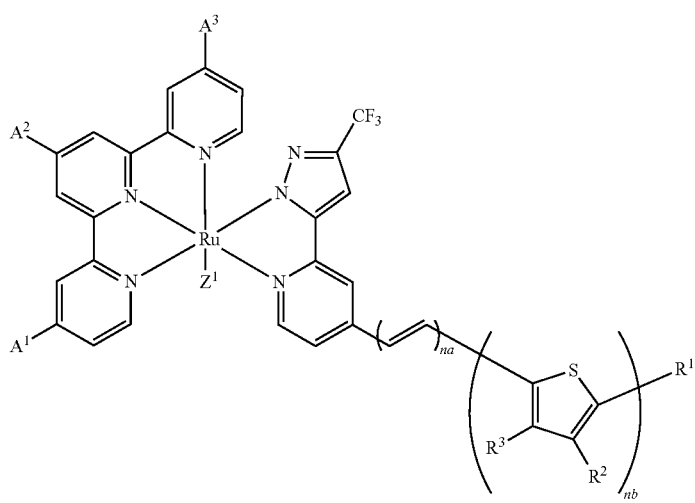

Formula (I-3C)

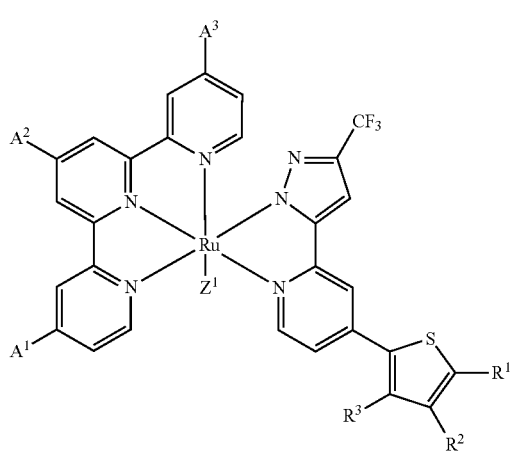

wherein, in Formulas (IA-3A) to (IA-3C), $Z^1$ has the same meaning as $Z^1$ in Formula (IA); $A^1$ to $A^3$ each independently represent a carboxyl group, or a potassium salt, a lithium salt or a cesium salt of a carboxyl group, provided that at least one of $A^1$ to $A^3$ represents a carboxyl group, and at least one of $A^1$ to $A^3$ represents a potassium salt, a lithium salt or a cesium salt of a carboxyl group; $R^0$ represents a hydrogen atom; $R^1$ represents a hydrogen atom, an alkyl group, an alkynyl group, an alkenyl group, an alkylthio group, an amino group or a heterocyclic group; $R^2$ and $R^3$ each independently represent a hydrogen atom, an alkyl group, an alkoxy group or a heterocyclic group; and na and nb each independently represent an integer of 0 or more, provided that the sum of na and nb is 2 or more.

(15) The photoelectric conversion element described in item (14), wherein, in Formula (I-3B), $R^1$ is an alkyl group, an alkynyl group, an amino group or an alkylthio group, and $R^2$ and $R^3$ each independently are a hydrogen atom or an alkoxy group.

(16) The photoelectric conversion element described in item (14), wherein, in Formula (I-3C), $R^1$ is an alkyl group, an alkynyl group or a heterocyclic group, and $R^2$ and $R^3$ are a hydrogen atom; or wherein, in Formula (I-3C), $R^1$ and $R^2$ are a hydrogen atom, and $R^3$ is an alkyl group.

(17) The photoelectric conversion element described in any one of items (13) to (16), wherein one of $A^1$ to $A^3$ is a carboxyl group, and the other two are a potassium salt, a lithium salt or a cesium salt of a carboxyl group.

(18) The photoelectric conversion element described in any one of items (1) to (17), wherein the semiconductor fine particles are titanium oxide.

(19) The photoelectric conversion element described in any one of items (1) to (18), wherein the salt of a carboxyl group is a potassium salt.

(20) A dye-sensitized solar cell, containing the photoelectric conversion element described in any one of items (1) to (19).

(21) A metal complex dye, which is represented by the following Formula (IA):

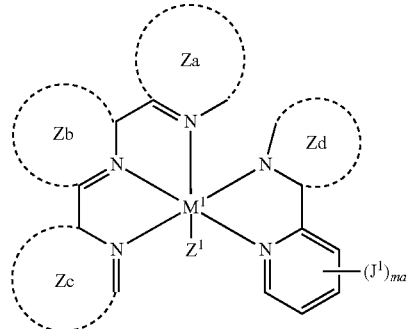

Formula (IA)

wherein $M^1$ represents a Ru atom or an Os atom; $Z^1$ represents a monodentate ligand; the rings Za, Zb and Zc each independently represent a group of nonmetallic atoms necessary for forming a nitrogen-containing 5- or 6-membered ring, provided that at least two of rings formed as the rings Za, Zb and Zc have a carboxyl group, or a potassium salt, a lithium salt or a cesium salt of the carboxyl group, at least one thereof being the carboxyl group, and at least one of the remainder being the potassium salt, the lithium salt or the cesium salt of the carboxyl group; the ring Zd represents a group represented by any one of the following Formulas (Zd-1) to (Zd-5); $J^1$ represents a substituent; and ma represents an integer of 0 to 2;

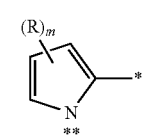

Formula (Zd-1)

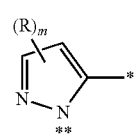

Formula (Zd-2)

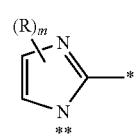

Formula (Zd-3)

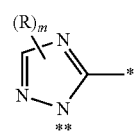

Formula (Zd-4)

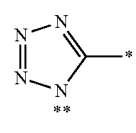

Formula (Zd-5)

wherein, in Formulas (Zd-1) to (Zd-5), R represents an alkyl group which may be substituted with a halogen atom, an aromatic group, or a heterocyclic group; m represents an integer of 0 or more; the symbol "*" represents a binding site with the pyridine ring having $J^1$; and the symbol "**" represents an atom or an atom anion coordinated with $M^1$.

(22) The metal complex dye described in item (21), wherein the salt of a carboxyl group is a potassium salt.

(23) A dye solution containing the metal complex dye described in item (21) or (22) dissolved therein.

In the present specification, unless otherwise specified, with respect to the carbon-carbon double bond, in a case where the E configuration or the Z configuration exists in the molecule, it may be either one of the two configurations or a mixture thereof. When there are two or more substituents, linking groups, ligands or the like (hereinafter referred to as substituents or the like) represented by a specific symbol, or when two or more substituents or the like are defined at the same time or alternatively, each of the substituents or the like may be the same or different from one another, unless otherwise specified. This also applies to definition of the number of substituents or the like. Further, when a plurality of substituents or the like are close to one another (particularly adjacent to each other), they may be linked to one another to form a ring, unless otherwise specified. Further, a ring, for example, an aliphatic ring, an aromatic ring, or a hetero ring, may be ring-fused to form a fused ring.

In the present invention, each substituent may be further substituted with another substituent, unless otherwise specified.

Advantageous Effects of Invention

According to the present invention, it is possible to provide a metal complex dye, a photoelectric conversion element, a dye-sensitized solar cell, and a dye solution containing the metal complex dye which simultaneously attain further improvement in durability and reduction in adsorption time.

Other and further features and advantages of the invention will appear more fully from the following description, appropriately referring to the accompanying drawings.

BRIEF DESCRIPTION OF DRAWINGS

FIG. 1 is a cross-sectional view schematically showing one embodiment of the photoelectric conversion element of the present invention, including an enlarged view of the circled portion in the layer thereof.

FIG. 2 is a cross-sectional view schematically showing the dye-sensitized solar cell produced in Example 1.

DESCRIPTION OF EMBODIMENTS

<<Photoelectric Conversion Element and Dye-Sensitized Solar Cell>>

In the photoelectric conversion element of the present invention, for example, as shown in FIG. 1, the photoelectric conversion element 10 is composed of: an electrically conductive support 1; a photoconductor layer 2 containing semiconductor fine particles 22 which has been sensitized by a dye (metal complex dye) 21; a charge transfer layer 3 which is a hole-transport layer, and a counter electrode 4. The electrically conductive support 1 in which the photoconductor layer 2 has been provided functions as a working electrode in the photoelectric conversion element 10. In this embodiment, the photoelectric conversion element 10 is shown as a system 100 utilizing a dye-sensitized solar cell, in which the photoelectric conversion element 10 is made to usable for a cell purpose which makes an operation means M to work via an external circuit 6.

In this embodiment, a light-receiving electrode 5 is formed of an electrically conductive support 1, and a photoconductor layer 2 containing semiconductor fine particles 22 to which the dye (metal complex dye) 21 has been adsorbed. The photoconductor layer 2 is designed according to the intended purpose, and it may have a single-layer structure or a multilayer structure. The dye (metal complex dye) 21 in one photoconductor layer may be a single species or a mixture, but as at least one of them, the following metal complex dye of the present invention is used. Light incident to the photoconductor layer 2 excites the dye (metal complex dye) 21. The excited dye has electrons having high energy, and these electrons are transferred from the dye (metal complex dye) 21 to a conduction band of the semiconductor fine particles 22, and further reach the electrically conductive support 1 by diffusion. At this time, the dye (metal complex dye) 21 is in an oxidized form. The electrons on the electrode, while working in an external circuit 6, return through the counter electrode 4 to the photoconductor layer 2 in which the oxidized form of the dye (metal complex dye) 21 and the electrolyte exist, to function as the solar cell.

In the present invention, regarding a method of producing materials and each member for use in the photoelectric conversion element or the dye-sensitized solar cell, ordinary ones in this kind may be adopted, and reference can be made to, for example, U.S. Pat. No. 4,927,721, U.S. Pat. No. 4,684,537, U.S. Pat. No. 5,084,365, U.S. Pat. No. 5,350,644, U.S. Pat. No. 5,463,057, U.S. Pat. No. 5,525,440, JP-A-7-249790, JP-A-2004-220974 or JP-A-2008-135197.

Hereinafter, an outline of main members will be described.

<Photoconductor Layer>

The photoconductor layer is a layer that contains an electrolyte described later and semiconductor fine-particles carrying a sensitizing dye including the following metal complex dye of the present invention.

In the photoconductor layer, semiconductor fine-particles carrying a metal complex dye having a particular chemical structure are contained.

In the present invention, further improvement in durability and reduction in adsorption time has simultaneously been realized by adjusting, in one molecule or one mole, a carboxyl group and a salt of the carboxyl group which the metal complex dye having this particular chemical structure possesses.

<<Metal Complex Dye>>

A metal complex dye according to the present invention is a metal complex dye represented by the following Formula (I).

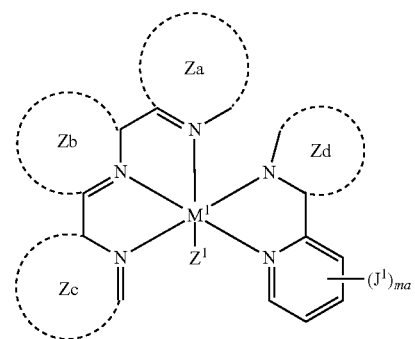

Formula (I)

In Formula (I), $M^1$ represents a Ru atom or an Os atom, and $Z^1$ represents a monodentate ligand. The rings Za, Zb and Zc each independently represent a group of nonmetallic atoms necessary for forming a nitrogen-containing 5- or 6-membered ring. Herein, at least two rings among the rings formed by the rings Za, Zb and Zc contain a carboxyl group, or a potassium salt, a lithium salt or a cesium salt of a carboxyl group. The ring Zd represents a group represented by any one of the following Formulas (Zd-1) to (Zd-5). $J^1$ represents a substituent. ma represents an integer of 0 to 2.

—$M^1$—

$M^1$ is a metal allowing 6-coordination, in the present invention, which is a Ru atom or an Os atom, preferably a Ru atom.

—$Z^1$—

$Z^1$ represents a monodentate ligand. As $Z^1$, for example, a monodentate ligand that coordinates at a group selected from the group consisting of an acyloxy group, an acylthio group, a thioacyloxy group, a thioacylthio group, an acylaminooxy group, a thiocarbamate group, a dithiocarbamate group, a thiocarbonate group, a dithiocarbonate group, a trithiocarbonate group, an acyl group, a thiocyanate group, an isothiocyanate group, a cyanate group, an isocyanate group, a selenate group, an isoselenate group, an isoselenocyanate group, a cyano group, an alkylthio group, an arylthio group, an alkoxy group and an aryloxy group; and a monodentate ligand selected from the group consisting of a halogen atom, a phosphine ligand, a carbonyl, a dialkylketone, a carbonamide, a thiocarbonamide, and thiourea, can be exemplified.

$Z^1$ is preferably an isothiocyanate group, an isoselenocyanate group, an isocyanate group, a halogen atom, or a cyano group. Note that when the ligand $Z^1$ contains an alkyl moiety, an alkenyl moiety, an alkynyl moiety, an alkylene moiety, or the like, these moieties may be linear or branched, and substituted or unsubstituted. Further, when the ligand $Z^1$ contains an aryl moiety, a heterocyclic moiety, a cycloalkyl moiety, or the like, these moieties may be substituted or unsubstituted and a single ring or a condensed ring.

—Rings Za to Zc—

The rings Za, Zb and Zc each independently represent a group of nonmetallic atoms necessary for forming a nitrogen-containing 5- or 6-membered ring. In the present invention, at least two rings among the rings formed by the rings Za, Zb and Zc contain a carboxyl group, or a potassium salt, a lithium salt or a cesium salt of a carboxyl group.

In the present invention, as to the nitrogen-containing heterocyclic ring which is formed by any of the rings Za to Zc, the kind thereof is not particularly limited, but a nitrogen-containing heteroaromatic ring is preferred.

In the present invention, it is preferable that all of the rings Za, Zb and Zc are for forming a 6-membered ring.

As to the nitrogen-containing 5-membered ring which is formed respectively by the rings Za to Zc, a heteroaromatic ring is preferred. The heteroaromatic ring has at least a nitrogen atom as a ring-constituting hetero atom and may contain an oxygen atom or a sulfur atom in addition to the nitrogen atom. The 5-membered ring to be formed includes: a hetero ring having only nitrogen atom as a hetero atom, such as a pyrrole ring, a pyrazole ring, an imidazole ring, a triazole ring, and a tetrazole ring; and a hetero ring having a nitrogen atom associated with atom(s) other than the nitrogen atom, such as an oxazole ring and a thiazole ring. Further, these rings may form a condensed ring with a benzene ring or a hetero ring (preferably aromatic hetero ring) as described above. Examples thereof include an indole ring, an isoindole ring, an indazole ring, a benzimidazole ring, a benzotriazole ring, a benzoxazole ring, and a benzothiazole ring.

The nitrogen-containing 6-membered ring which is formed respectively by the rings Za to Zc includes a 6-membered hetero ring. As to the 6-membered nitrogen-containing hetero ring, a heteroaromatic ring is preferred. Further, as the ring-constituting hetero atom, the ring has at least a nitrogen atom, in addition to it, and the ring may contain an oxygen atom, a sulfur atom. Examples of the 6-membered ring to be formed include a pyridine ring, a pyrimidine ring, a pyrazine ring, a pyridazine ring, and a triazine ring, each of which may be condensed with a benzene ring or a hetero ring. Examples of the condensed hetero ring include a quinoline ring, an isoquinoline ring, a quinoxazine ring, a quinazoline ring, and a cinnoline ring.

As to the 6-membered ring to be formed, a pyridine ring and a nitrogen-containing heteroaromatic ring having two nitrogen atoms as a ring-constituting atom are preferred, and a pyridine ring is preferred in particular.

The ring formed by Za to Zc may have a substituent. Examples of the substituent include the substituent T described below.

Further, the ring may have an acidic group other than a carboxyl group, or a potassium salt, a lithium salt or a cesium salt of the carboxyl group, including the substituent T. In the present invention, however, it is preferable that the acidic group is only a carboxyl group, or a potassium salt, a lithium salt or a cesium salt of the carboxyl group.

—Acidic Group—

In the present invention, the acidic group represents a substituent having a dissociative proton. Examples thereof include as a carboxyl group including a potassium salt, a lithium salt or a cesium salt of a carboxyl group, a phosphonyl group, a phosphoryl group, a sulfo group, and a boric acid group; or a group having any of these groups. Among these, a carboxyl group, a phosphonyl group, and a group having any of these groups are preferred. Further, the acidic group may be in a dissociation form due to release of a proton, or may be a salt thereof. When the acidic group is a salt, a counter ion upon forming the salt is not particularly limited, and specific examples include a positive ion in the below-mentioned counter ion CI. In the present invention, as described above, the acidic group may be a group which binds to the ring via a linking group. Examples thereof include a carboxyvinylene group, a dicarboxyvinylene group, a cyanocarboxyvinylene group and a carboxyphenyl group as a preferred one. Note that, the acidic group exemplified above and a preferable range thereof may be referred to as an acidic group Ac.

—Carboxyl Group, or Potassium Salt, Lithium Salt or Cesium Salt of Carboxyl Group—

In the present invention, at least two rings among the rings formed as the rings Za, Zb and Zc contain a carboxyl group, or a potassium salt, a lithium salt or a cesium salt of a carboxyl group. The ring having a carboxyl group, or a potassium salt, a lithium salt or a cesium salt of the carboxyl group is any of the rings Za, Zb and Zc, and at least two of the carboxyl group, or the potassium salt, the lithium salt or the cesium salt of the carboxyl group may be located at the same ring or different rings from one another. In the present invention, it is preferable that these groups are located at different rings from one another.

Further, in the present invention, the rings have at least two of a carboxyl group, or a potassium salt, a lithium salt or a cesium salt of the carboxyl group, and the number thereof is preferably 2 to 5, more preferably 2 to 4, still more preferably 2 or 3, and particularly preferably 3.

Further, not only a carboxyl group, or a potassium salt, a lithium salt or a cesium salt of the carboxyl group which directly binds to each ring, but also these groups may bind to the ring through a linking group.

For example, a group containing a carboxyl group may bind to each ring in such a way as shown by the following Formulas (Anc-1) to (Anc-4).

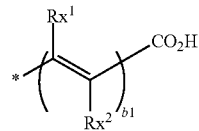

Formula (Anc-1)

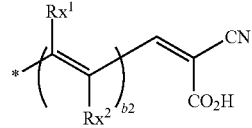

Formula (Anc-2)

-continued

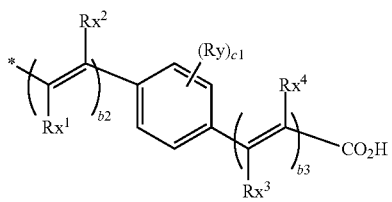

Formula (Anc-3)

Formula (Anc-4)

In Formulas (Anc-1) to (Anc-4), $Rx^1$ to $Rx^4$, $Ry^1$ and $Ry^2$ each independently represent a hydrogen atom or a substituent. Ry represents a substituent. b1 represents an integer of 1 to 3, and b2 and b3 each independently represent an integer of 0 to 2. c1 represents an integer of 0 to 4.

Note that although Formulas (Anc-1) to (Anc-4) each show —$CO_2H$ (a carboxyl group) as a representative thereof, the carboxyl group shown here means to include also a potassium salt, a lithium salt or a cesium salt of the carboxyl group.

Here, -$L^1$-$Ah^1$ to -$L^3$-$Ah^3$ described below are groups as described above, and $L^1$ to $L^3$ each include a divalent linking group located between * and —$CO_2H$ in the above Formulas (Anc-1) to (Anc-4).

Examples of the substituent represented by $Rx^1$ to $Rx^4$, Ry, $Ry^1$ and $Ry^2$ in Formulas (Anc-1) to (Anc-4) include the substituent T described below. b1 is preferably 1 or 2, more preferably 1. b2 or b3 is preferably 0 or 1. When b2 and b3 exist at the same time, the total of b2 and b3 (b2+b3) is preferably 1 or 2.

In the present invention, the salt of a carboxyl group is selected from the group consisting of a potassium salt, a lithium salt and a cesium salt. That is to say, in the present invention, a counter ion of the carboxyl ion is an ion selected from a potassium ion, a lithium ion and a cesium ion among the alkali metal ions. As for these ions, the salt of the carboxyl group may have at least two kinds of mix. However, a single kind of the ion is preferred.

The salt of a carboxyl group is preferably a potassium salt or a lithium salt, particularly preferably a potassium salt.

Note that, in the present specification, hereinafter a simple expression "the salt of the carboxyl group" means the above-mentioned salt.

In the present invention, the semiconductor fine particles used in the present invention interacts with a carboxyl group, or a potassium salt, a lithium salt or a cesium salt of the carboxyl group, of the metal complex dye on the surface of the semiconductor fine particles. This interaction is representatively adsorption.

The semiconductor fine particles used in the present invention include semiconductor fine particles carrying the metal complex dye in which the ratio (number of salt of carboxyl group/total number of carboxyl group and salt of carboxyl group) α of the number of the salt of the carboxyl group to the total number of the carboxyl group and the salt of the carboxyl group to be found in 1 mole of the metal complex dye, lies in the range of 0.1 to 0.9.

Here, when any two of the rings formed as the rings Za, Zb and Zc have a carboxyl group, or a potassium salt, a lithium salt or a cesium salt of the carboxyl group, the above ratio α is preferably 0.15 to 0.55. When all of the rings formed as the rings Za, Zb and Zc have a carboxyl group, or a potassium salt, a lithium salt or a cesium salt of the carboxyl group, the above ratio α is preferably 0.1 to 0.7.

In any of these cases, the above ratio α is preferably 0.2 to 0.5, and more preferably 0.25 to 0.4.

Further, as described above, even if the carboxyl group and the salt of the carboxyl group are not average of the whole metal complex dyes to be used, or even a metal complex dye having a carboxyl group and a salt of the carboxyl group in one molecule thereof, these metal complex dyes may be isolated to use.

In this case, when any two of rings formed as the rings Za, Zb and Zc have a carboxyl group, one of them is a carboxyl group, while the other is a salt of the carboxyl group, and the above ratio α is fixed to 0.5. Further, for example, when each of rings formed as the rings Za, Zb and Zc has a carboxyl group, the dye results in having three carboxyl groups in one molecule thereof, and in the present invention, one or two of three carboxyl groups make a salt of the carboxyl group. When only one thereof is a salt of the carboxyl group, the above ratio α is 1/3, while when two thereof are a carboxyl group, the above ratio α is 2/3. When the dye has three carboxyl groups, it is particularly preferable that a dye has one of a carboxyl group and the remaining two of a salt of the carboxyl group.

As just described, in order to adjust the above ratio α, it is the simplest way to make all of the carboxyl groups existing in the molecule to be a carboxyl group (—$CO_2H$) or to make all of the carboxyl groups to be a salt of the carboxyl group, and thereafter to add thereto an alkali compound or an acid so as to be the above ratio α.

Note that an effective development of the effects due to the above ratio α in the present invention is affected by a chemical structure other than a carboxyl group, or a potassium salt, a lithium salt, or a cesium salt of the metal complex dye used in the present invention, and the chemical structure represented by the above-described Formula (1) is effective and exhibits a structural specificity.

The foregoing structural specificity is peculiar to the case where, in the ligand which constitutes the metal complex dye, the ligand having a carboxyl group, or a potassium salt, a lithium salt, or a cesium salt of the carboxyl group is not a bidentate ligand but a terdentate ligand, and the remaining ligand to be combined with the terdentate ligand is a bidentate ligand, rather the remaining ligand combined with the ligand being bidentate ligand having a linkage of a cyclic structure including at least a nitrogen atom anion as a coordination atom. It is assumed that, in the case where the ligand having a carboxyl group, or a potassium salt, a lithium salt, or a cesium salt of the carboxyl group is a terdentate ligand, and the remaining ligand is a terdentate ligand, a steric strain increases upon coordination to a central metal of the octahedral coordination, so that stability of the metal complex dye itself becomes worse.

In the metal complex dye having the foregoing structure, it appears that by adjusting the numbers of a carboxyl group and a salt of the carboxyl group, a difference between a hydrophilic portion and a hydrophobic portion in the dye molecule of the hydrophobicity-enhanced ligand is increased through an interaction with the metal complex dye on the surface of the semiconductor fine particles, representatively through interaction due to adsorption, and by mixing the carboxyl group and the salt of the carboxyl group, including an intermolecular matter of the dye, due to a change of microscopic partial orientation, and due to a microscopic or macroscopic adjustment of orientation including orientation of the molecule at the time of adsorption of one molecule with the carboxyl group and the salt of the carboxyl group on the surface of the semiconductor particles, in particular, due to adjustment of orientation structure capable of suppressing access of water molecule, or adsorption•desorption property, or the like, an adsorption time of the dye has been reduced and durability has been largely improved.

Therefore, it is impossible to expect behavior of the metal complex represented by the Formula (I) of the present invention which is substantially different in its chemical structure and physical and chemical properties due to the chemical structure, from a metal complex dye which is extremely hydrophilic and has a small molecular volume, such as a combination of one terdentate ligand and three monodentate ligands or a combination of two bidentate ligands each having a carboxyl group and two monodentate ligands, like N719 and Black Dye.

Specifically, it is presumed that adsorption time is reduced due to such a mechanism of action that, in the metal complex dye having a hydrophilic portion (Za to Zc) and a hydrophobic portion (Zd and a pyridine ring), hydrophilicity is partially further improved by partially making the hydrophilic portion to a salt of the carboxylic group, so that the metal complex dye is drawn on the surface of the semiconductor fine particles through a hydrophilic interaction with a hydrophilic surface of the semiconductor fine particles and a carboxyl group which is not made yet to a salt adsorbs on the surface of the semiconductor fine particles. Further, as a mechanism of dye adsorption, a dye adsorbs by various interactions. As one of them, a path in which a subsequent dye adsorbs, while being drawn, on a previously adsorbed dye by an intermolecular action between dyes, is thought. In this case, the adsorption area of the dye is biased, so that a large adsorption amount area and a small adsorption amount area are unevenly distributed, which results in sparseness. From a small dye area, water begins to adsorb on the surface of the semiconductor fine particles. This becomes a cause of desorption of the dye. In the dye of the present invention, however, an absorption amount becomes more uniform regardless of the location because the effect that the dye is drawn by a hydrophilic interaction between a partially salt-made site of the dye and the semiconductor fine particles is produced as described above. As a result, durability is improved for the reason that the dye itself inhibits access of water to the surface of the semiconductor fine particles. Further, it is presumed that the structure of the dye of the present invention is also characterized in that access of water which causes desorption of the dye is inhibited by the hydrophobic portion which is located in the side opposite to an adsorption site of the hydrophilic portion.

—Ring Zd—

The ring Zd is represented by any one of Formulas (Zd-1) to (Zd-5).

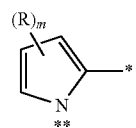

Formula (Zd-1)

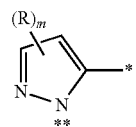

Formula (Zd-2)

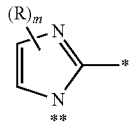

Formula (Zd-3)

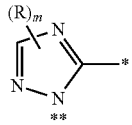

Formula (Zd-4)

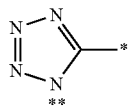

Formula (Zd-5)

In Formulas (Zd-1) to (Zd-5), R represents an alkyl group which may be substituted with a halogen atom, an aromatic group, or a heterocyclic group. m represents an integer of 0 or more. Herein, the symbol "*" represents a binding site with the pyridine ring having $J^1$. The symbol "**" represents an atom or an atom anion coordinated with $M^1$.

In the alkyl group represented by R which may be substituted with a halogen atom, the halogen atom is preferably a fluorine atom, a chlorine atom and a bromine atom; more preferably a fluorine atom and a chlorine atom; and further preferably a fluorine atom. The number of carbon atoms of the alkyl group is preferably 1 to 18, more preferably 1 to 8, and further preferably 1 to 4. The halogen-substituted alkyl group is preferably a perhalogenated alkyl group, more preferably a perfluorinated alkyl group, and particularly preferably a perfluorinated methyl group.

Examples of the aromatic group represented by R include phenyl and naphthyl. The heterocyclic group preferably has a ring-constituting atom selected from an oxygen atom, a sulfur atom and a nitrogen atom. A 5- or 6-membered ring is preferred.

These groups represented by R may be substituted with a substituent. Examples of the substituent include the substituent T described below.

m is preferably 0 or 1, more preferably 1.

Among Formulas (Zd-1) to (Zd-5), Formulas (Zd-1) to (Zd-4) are preferred, Formulas (Zd-1), (Zd-2) and (Zd-4) are more preferred, and Formula (Zd-2) is further preferred.

—$J^1$—

$J^1$ represents a substituent. Among these, $J^1$ is preferably an alkenyl group or a heteroaryl group. Examples of the alkenyl group and the heteroaryl group include groups corresponding to the substituent T described below.

Here, when $J^1$ is a heteroaryl group, the hetero atom of the ring-constituting atom is preferably a sulfur atom, an oxygen atom, a nitrogen atom or a selenium atom, and the heteroaryl ring is preferably a 5- or 6-membered ring and may be condensed with an aryl ring such as a benzene ring, a non-aromatic hetero ring such as an ethylenedioxy ring, or a heteroaryl ring. These rings may have a substituent. Such substituent includes, as described above, the substituent T described below.

The alkenyl group of $J^1$ is preferably an ethenyl group, and also preferably a group which an ethenyl group is combined with an ethynyl group whereby a conjugation has been extended. A group which an ethenyl group is combined with an heteroaryl group, and a group which heteroaryl groups are combined with each other are also preferred.

$J^1$ is preferably a group containing a heteroaryl ring. As the heteroaryl ring, a thiophene ring is preferable.

The group containing a thiophene ring as $J^1$ is preferably a group represented by any one of the following Formulas (J-1) to (J-5).

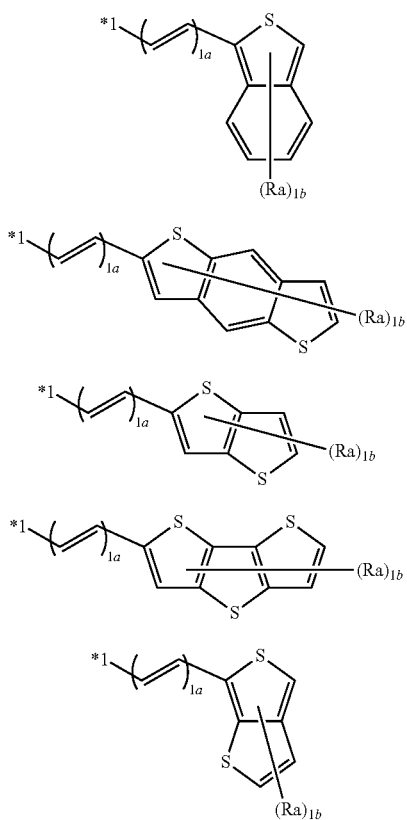

Formula (J-1)

Formula (J-2)

Formula (J-3)

Formula (J-4)

Formula (J-5)

In Formulas (J-1) to (J-5), Ra represents a substituent. Ia and Ib each independently represent an integer of 0 or more. The symbol "*1" represents a binding site with the pyridine ring.

Ra represents a substituent. Among these, Ra is preferably an alkyl group, an alkenyl group, an alkynyl group, an alkoxy group, an alkylthio group, or an amino group. Examples thereof include groups corresponding to the substituent T described below.

When Ra is an alkyl group, an alkoxy group or an alkylthio group, these groups may be a linear group or a branched group. However, a linear alkyl group, a linear alkoxy group and a linear alkylthio group are preferred. The number of carbon atoms of these groups is preferably 1 to 12, more preferably 2 to 8, further preferably 3 to 8, and particularly preferably 4 to 7.

When Ra is an alkenyl group or an alkynyl group, these groups may be a linear group or a branched group. However, a linear alkenyl group and a linear alkynyl group are preferred. The number of carbon atoms of these groups is preferably 2 to 12, more preferably 2 to 8, further preferably 3 to 8, and particularly preferably 4 to 7.

When Ra is an amino group, the amino group is preferably an alkylamino group or an arylamino group; more preferably a dialkylamino group, a N-alkyl-N-arylamino group, or a diarylamino group; and further preferably a dialkylamino group. The number of carbon atoms of these groups is preferably 2 to 24, more preferably 4 to 16, further preferably 6 to 16, and particularly preferably 8 to 14.

Ia represents an integer of 0 or more, preferably an integer of 0 to 2, more preferably 0 or 1, and further preferably 0.

Ib represents an integer of 0 or more, preferably an integer of 0 to 2, and more preferably 1 or 2.

—ma— ma represents an integer of 0 to 2, preferably 1.

—Chemical Structure of Metal Complex Dye—

In the present invention, the chemical structure of the metal complex dye represented by Formula (I) is preferably represented by the following Formula (I-1).

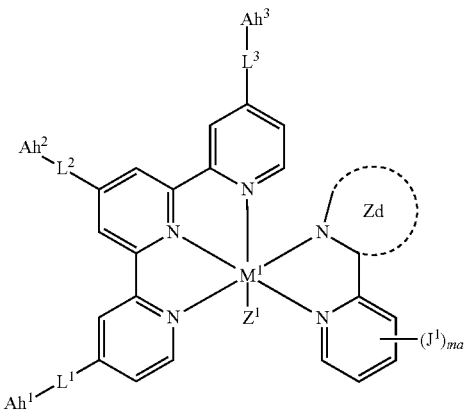

Formula (I-1)

In Formula (I-1), the ring Zd, $M^1$, $Z^1$, $J^1$ and ma have the same meaning as the ring Zd, $M^1$, $Z^1$, $J^1$ and ma in Formula (I), and preferable ranges thereof are also the same. $L^1$ to $L^3$ each independently represent a single bond or a divalent linking group. $Ah^1$ to $Ah^3$ each independently represent a hydrogen atom, a carboxyl group, or a potassium salt, a lithium salt or a cesium salt of a carboxyl group. Herein, at least two of $Ah^1$ to $Ah^3$ each are a carboxyl group, or a potassium salt, a lithium salt or a cesium salt of a carboxyl group.

$L^1$ to $L^3$ each independently represent a single bond or a divalent linking group. As to the divalent linking group, an ethynylene group, an ethenylene group, a phenylene group, a divalent heteroarylene group, or a combination thereof is preferred. That is, such a linking group so as to link a carboxyl group and rings Za to Zc with a π-conjugation is preferred.

In addition, the dye in which $L^1$ to $L^3$ are each a single bond is preferred. Depending on a purpose or a performance to be required, the case of a single bond is also preferable from the viewpoint that the metal complex dye can be produced at a low cost.

In the present invention, the chemical structure of the metal complex dye represented by the following Formula (I) is further preferably represented by Formula (I-2), particularly preferably any one of the following Formulas (I-3A) to (I-3C).

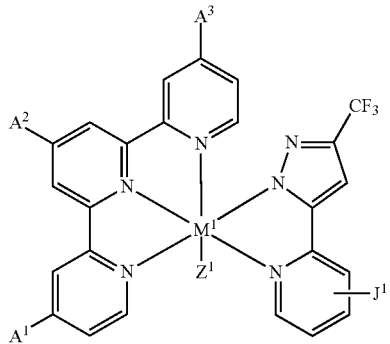

Formula (I-2)

In Formula (I-2), $M^1$, $Z^1$ and $J^1$ have the same meaning as $M^1$, $Z^1$ and $J^1$ in Formula (I-1), and preferable ranges thereof are also the same. $A^1$ to $A^3$ each independently represent a carboxyl group, or a potassium salt, a lithium salt or a cesium salt of a carboxyl group. Herein, at least two of $A^1$ to $A^3$ are a carboxyl group, or a potassium salt, a lithium salt or a cesium salt of a carboxyl group.

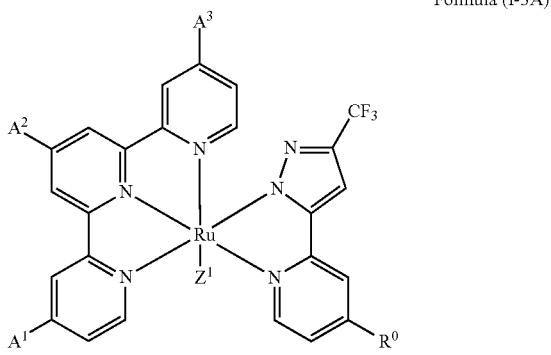

Formula (I-3A)

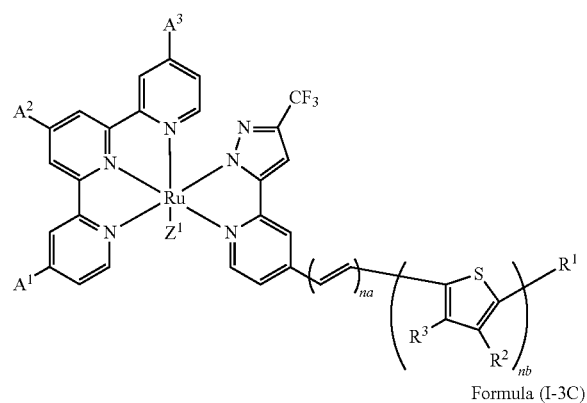

Formula (I-3B)

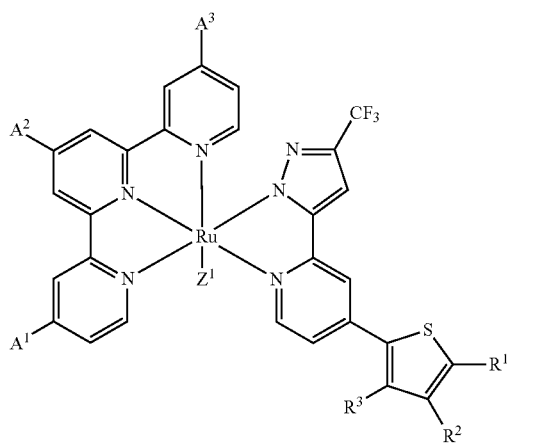

Formula (I-3C)

In Formulas (I-3A) to (I-3C), $Z^1$ has the same meaning as $Z^1$ in Formula (I), and a preferable range thereof is also the same. $A^1$ to $A^3$ each independently represent a carboxyl group, or a potassium salt, a lithium salt or a cesium salt of a carboxyl group. Herein, at least two of $A^1$ to $A^3$ are a carboxyl group, or a potassium salt, a lithium salt or a cesium salt of a carboxyl group. $R^0$ represents a hydrogen atom; $R^1$ represents a hydrogen atom, an alkyl group, an alkynyl group, an alkenyl group, an alkylthio group, an amino group or a heterocyclic group. $R^2$ and $R^3$ each independently represent a hydrogen atom, an alkyl group, an alkoxy group or a heterocyclic group. na and nb each independently represent an integer of 0 or more, with the proviso that the sum of na and nb (na+nb) is 2 or more.

Each of the groups represented by $R^1$ to $R^3$ is preferably a group corresponding to the substituent T described below. These groups may be substituted with a substituent. Examples of the substituent include the substituent T described below.

$R^1$ and $R^2$ may be bonded to each other to form a ring, and $R^2$ and $R^3$ may be bonded to each other to form a ring.

In the above, the amino group is preferably an alkylamino group or an arylamino group; more preferably a dialkylamino group, a N-alkyl-N-arylamino group, or a diarylamino group; and most preferably a dialkylamino group.

The alkyl group, the alkynyl group, the alkenyl group, the alkoxy group, the alkylthio group and the amino group have preferably 1 to 24 carbon atoms, more preferably 2 to 24 carbon atoms, further preferably 3 to 24 carbon atoms, particular preferably 4 to 24 carbon atoms, and most preferably 5 to 20 carbon atoms.

The heterocyclic group is preferably an aromatic heterocyclic group, preferably an heterocyclic group having a thiophene ring. The heterocyclic group may have a substituent. Examples of the substituent include the substituent T described below. Among these, a halogen atom, an alkyl group, an aryl group, a heterocyclic group, an alkoxy group, and an aryloxy group are preferred.

na and nb each independently represent an integer of 0 or more. From the viewpoint of improving c due to extension of conjugation, the sum of na and nb is at least 2, and the sum of na and nb is preferably 2 to 4, more preferably 2 or 3, and particularly preferably 2. For example, it is preferable that na is 0 and nb is 2; and that na is 1 or 2 and nb is 0 to 2.

na and nb each are preferably a number of 1 or more, and more preferably 1 or 2.

Among Formulas (I-3A) to (I-3C), Formula (I-3B) or (I-3C) is preferable.

In Formula (I-3B), it is preferable that $R^1$ is an alkyl group, an alkynyl group, an amino group or an alkylthio group, and $R^2$ and $R^3$ each independently are a hydrogen atom or an alkoxy group. The number of carbon atoms of the each group represented by $R^1$ is preferably 1 to 24, more preferably 2 to 24, further preferably 3 to 24, particularly preferably 4 to 24, and most preferably 5 to 20.

In Formula (I-3C), it is preferable that $R^1$ is a hydrogen atom, an alkyl group, an alkynyl group or a heterocyclic group, and $R^2$ and $R^3$ each independently are a hydrogen atom or an alkyl group. It is more preferable that $R^1$ is an alkyl group, an alkynyl group or a heterocyclic group, and $R^2$ and $R^3$ are a hydrogen atom. Alternatively, it is more preferable that $R^1$ and $R^2$ are a hydrogen atom, and $R^3$ is an alkyl group. The number of carbon atoms of each of the groups represented by $R^1$ to $R^3$ is preferably 3 to 24, more preferably 4 to 24, and further preferably 5 to 20.

$A^1$ to $A^3$ each independently, each independently, represent a carboxyl group, or a potassium salt, a lithium salt or a cesium salt of a carboxyl group. A metal complex dye in which $A^1$ to $A^3$ have been replaced with the groups represented by the above-described Formulas (Anc-1) to (Anc-4) is also preferred.

As to the semiconductor fine particles used in the present invention, semiconductor fine particles carrying a metal complex dye are used and in the metal complex dye, a ratio (number of salt of carboxyl group/total number of carboxyl group and salt of carboxyl group) α of the number of the salt of the carboxyl group to the total number of the carboxyl group and the salt of the carboxyl group to be found in 1 mole of the metal complex dye, lies in the range of 0.1 to 0.9.

However, in terms of a molecular level, a metal complex dye represented by the following Formula (IA) is preferred.

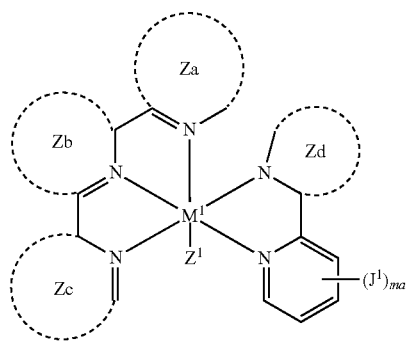

Formula (IA)

In Formula (IA), $M^1$ represents a Ru atom or an Os atom; $Z^1$ represents a monodentate ligand; the rings Za, Zb and Zc each independently represent a group of nonmetallic atoms necessary for forming a nitrogen-containing 5- or 6-membered ring, with the proviso that at least two of rings formed as the rings Za, Zb and Zc have a carboxyl group, or a potassium salt, a lithium salt or a cesium salt of the carboxyl group, at least one thereof being the carboxyl group, and at least one of the remainder being the potassium salt, the lithium salt or the cesium salt of the carboxyl group; the ring Zd is represented by any one of the following Formulas (Zd-1) to (Zd-5); $J^1$ represents a substituent; and ma represents an integer of 0 to 2.

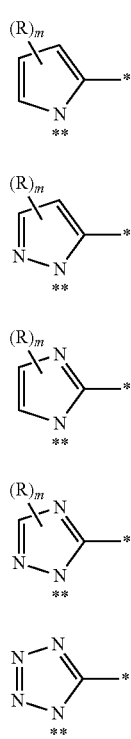

Formula (Zd-1)

Formula (Zd-2)

Formula (Zd-3)

Formula (Zd-4)

Formula (Zd-5)

In Formulas (Zd-1) to (Zd-5), R represents an alkyl group which may be substituted with a halogen atom, an aromatic group, or a heterocyclic group. m represents an integer of 0 or more. The symbol "*" represents a binding site with the pyridine ring having $J^1$, and the symbol "**" represents an atom or an atom anion coordinated with $M^1$.

Note that $M^1$, $Z^1$, rings Za to Zc, ring Zd, $J^1$ and ma in Formula (IA) each has the same definitions as $M^1$, $Z^1$, rings Za to Zc, ring Zd, $J^1$ and ma in Formula (I), except that, in at least 2 groups of the carboxyl group or the potassium salt, the lithium salt, or the cesium salt of the carboxyl group, which the rings Za to Zc in Formula (IA) have, at least one thereof is the potassium salt, the lithium salt, or the cesium salt of the carboxyl group, while at least one of the remainder is the carboxyl group.

In Formulas (Zd-1) to (Zd-5), R and m have the same meaning as R and m in Formulas (Zd-1) to (Zd-5) in Formula (I).

As described above, adjustment of the number of the carboxyl group and the number of the above salt of the carboxyl group in one molecule enables to improve workability at the process of dye adsorption in which the dye is adsorbed on the surface of the semiconductor fine particles, and at the same time, allows adjustment of the above-described ratio α with a certainty.

The metal complex dye represented by Formula (IA) is preferably represented by the following Formula (IA-1), more preferably represented by the following Formula (IA-2), and further preferably any one of the following Formulas (IA-3A) to (IA-3C).

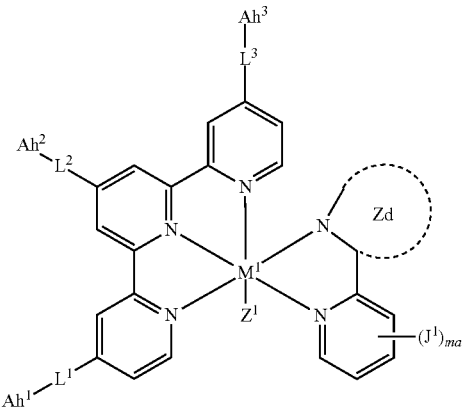

Formula (IA-1)

In Formula (IA-1), the ring Zd, $M^1$, $Z^1$, $J^1$ and ma have the same meaning as the ring Zd, $M^1$, $Z^1$, $J^1$ and ma in Formula (IA). $L^1$ to $L^3$ each independently represent a single bond or a divalent linking group. $Ah^1$ to $Ah^3$ each independently represent a hydrogen atom, a carboxyl group, or a potassium salt, a lithium salt or a cesium salt of a carboxyl group. Herein, at least two of $Ah^1$ to $Ah^3$ each are a carboxyl group, or a potassium salt, a lithium salt or a cesium salt of a carboxyl group.

As to the at least two of a carboxyl group or a potassium salt, a lithium salt, or a cesium salt of the carboxyl group in $Ah^1$ to $Ah^3$ in Formula (IA-1), the definitions of Formula (IA-1) are the same as Formula (I-1), except that at least one is a potassium salt, a lithium salt, or a cesium salt of the carboxyl group, while at least one of the remainder is a carboxyl group.

Formula (IA-2)

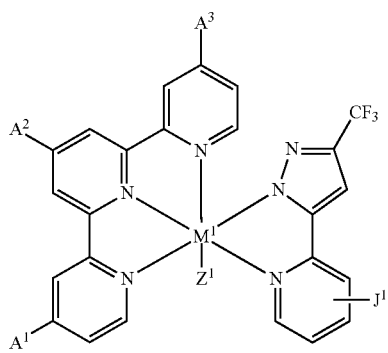

In Formula (IA-2), $M^1$, $Z^1$ and $J^1$ have the same meaning as $M^1$, $Z^1$ and $J^1$ in Formula (IA-1). $A^1$ to $A^3$ each independently represent a carboxyl group, or a potassium salt, a lithium salt or a cesium salt of a carboxyl group, with the proviso that at least one thereof represents a carboxyl group, and at least one thereof represents a potassium salt, a lithium salt or a cesium salt of a carboxyl group.

In Formula (IA-2), the definitions have the same meaning as those in Formula (I-2), except that $A^1$ to $A^3$ each independently represent a carboxyl group, or a potassium salt, a lithium salt or a cesium salt of a carboxyl group, with the proviso that at least one thereof represents a carboxyl group, and at least one thereof represents a potassium salt, a lithium salt or a cesium salt of a carboxyl group.

Formula (IA-3A)

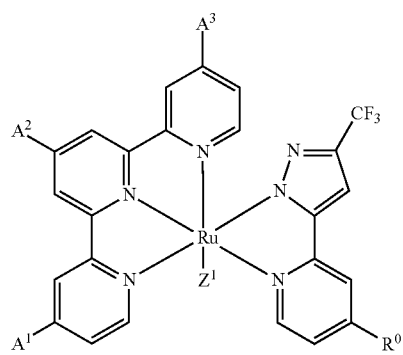

Formula (IA-3B)

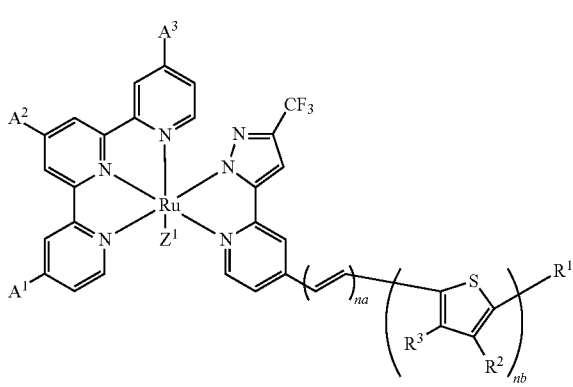

Formula (IA-3C)

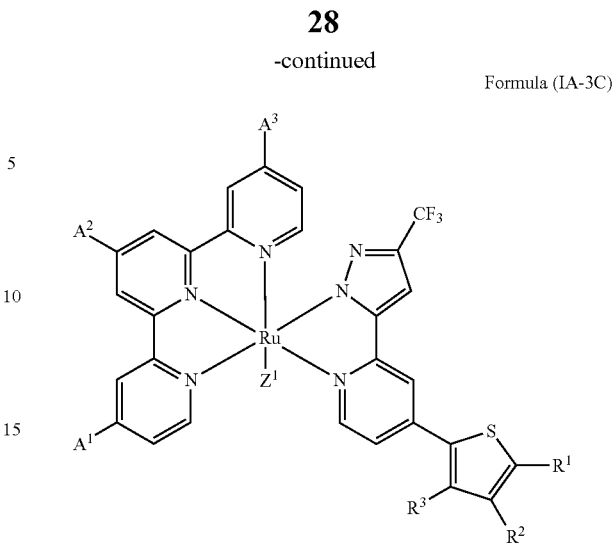

In Formulas (IA-3A) to (IA-3C), $Z^1$ has the same meaning as $Z^1$ in Formula (IA). $A^1$ to $A^3$ each independently represent a carboxyl group, or a potassium salt, a lithium salt or a cesium salt of a carboxyl group. Herein, at least one thereof represents a carboxyl group, and at least one thereof represents a potassium salt, a lithium salt or a cesium salt of a carboxyl group. $R^0$ represents a hydrogen atom; $R^1$ represents a hydrogen atom, an alkyl group, an alkynyl group, an alkenyl group, an alkylthio group, an amino group or a heterocyclic group. $R^2$ and $R^3$ each independently represent a hydrogen atom, an alkyl group, an alkoxy group or a heterocyclic group. na and nb each independently represent an integer of 0 or more, with the proviso that the sum of na and nb (na+nb) is 2 or more.

In Formulas (IA-3A) to (IA-3C), the definitions have the same meaning as those in Formulas (I-3A) to (I-3C), except that $A^1$ to $A^3$ each independently represent a carboxyl group, or a potassium salt, a lithium salt or a cesium salt of a carboxyl group, with the proviso that at least one thereof represents a carboxyl group, and at least one thereof represents a potassium salt, a lithium salt or a cesium salt of a carboxyl group.

Here, it is preferable that the number of a potassium salt, a lithium salt, or a cesium salt of the carboxyl group is lower than the number of a carboxyl group. For example, when the sum of the number of a carboxyl group and the number of a potassium salt, a lithium salt, or a cesium salt of the carboxyl group is 3, it is preferable that 2 of them are carboxyl groups and the remaining 1 is a potassium salt, a lithium salt, or a cesium salt of the carboxyl group. Specifically, it is particularly preferable that, of the above-described $A^1$ to $A^3$ and $Ah^1$ to $Ah^a$, 2 are carboxyl groups and the remaining 1 is a potassium salt, a lithium salt, or a cesium salt of the carboxyl group.

Specific examples of the bidentate ligand containing the ring Zd are shown below, but the present invention is not limited to these.

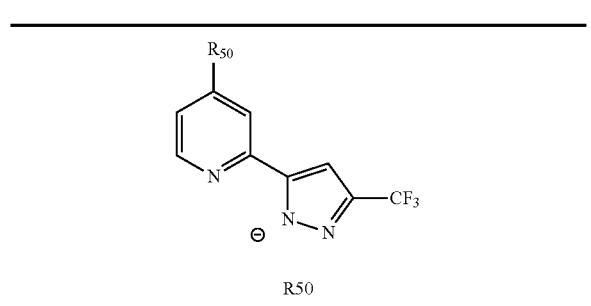
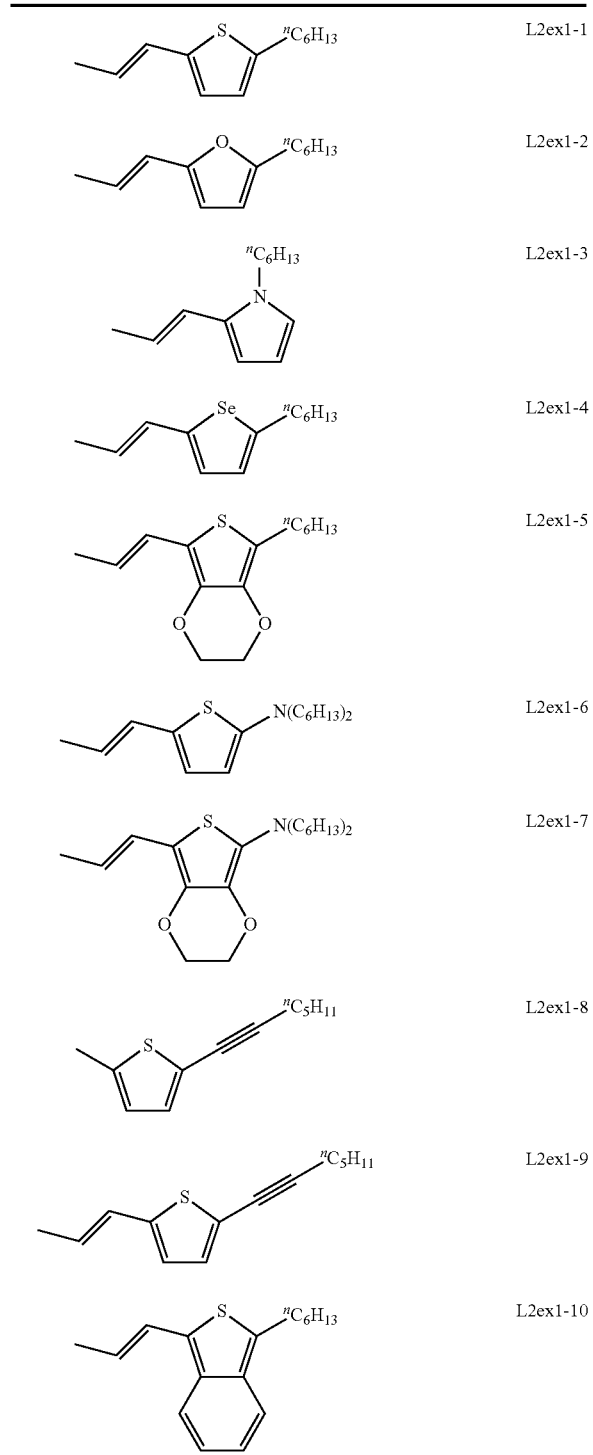
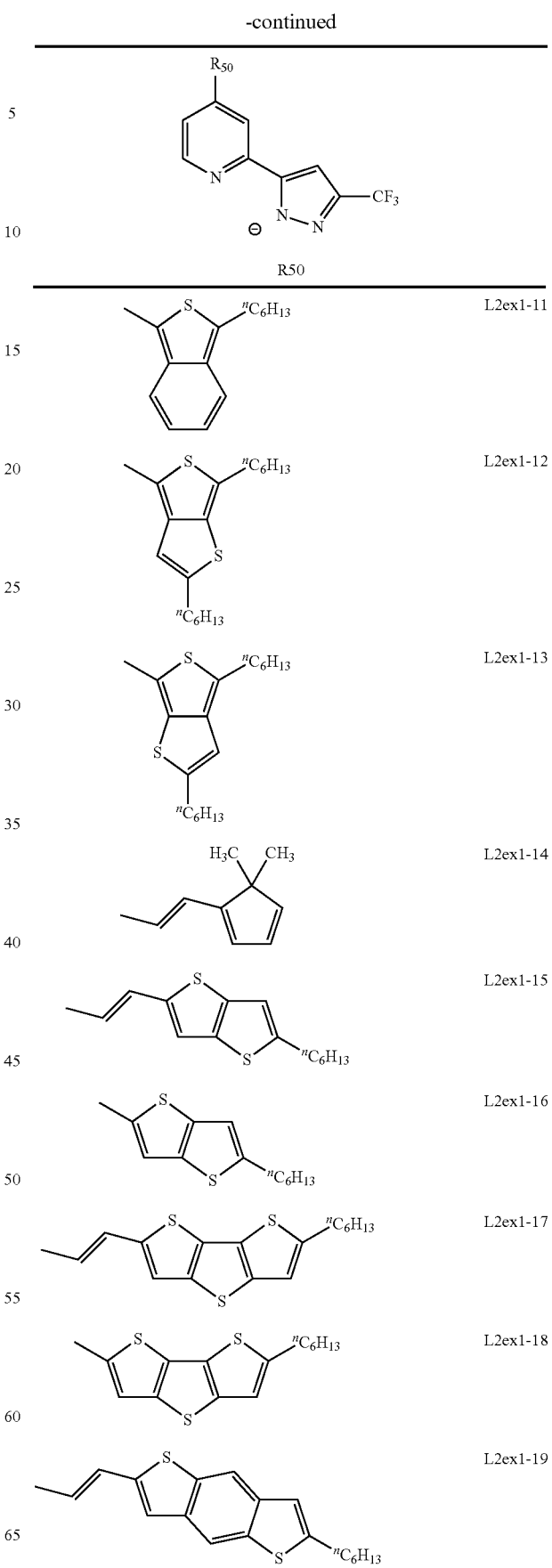

| | |
|---|---|
| ![R50-pyridine-pyrazole-CF3] | |
| R50 | |
| methylthieno-thiophene-nC6H13 | L2ex1-20 |
| methyl-bithiophene-nC6H13 | L2ex1-21 |
| methyl-thiophene-nC6H13 | L2ex1-22 |
| —H | L2ex1-23 |
| methylthiophene with C6H13n | L2ex1-24 |
| propenyl-thiophene-SnC6H13 | L2ex1-25 |
| methyl-thiophene-nC6H13 with C6H13n | L2ex1-26 |
| methylthiophene | L2ex1-27 |
| methyl-thiophene-SnC6H13 | L2ex1-28 |
| methyl-thiophene-phenyl-OnC6H13 | L2ex1-29 |
| methyl-terthiophene with nC6H13 groups | L2ex1-30 |

| | |
|---|---|
| ![R50-pyridine-pyrazole-CF3] | |
| R50 | |
| methyl-terthiophene | L2ex1-31 |
| propenyl-nC6H13 | L2ex1-32 |
| propenyl-phenyl | L2ex1-33 |

| | |
|---|---|
| ![R51-pyridine-pyrazole-CF3] | |
| R51 | |
| propenyl-thiophene-nC6H13 | L2ex2-1 |
| propenyl-EDOT-nC6H13 | L2ex2-2 |
| propenyl-EDOT-N(C6H13)2 | L2ex2-3 |
| propenyl-thiophene-SnC6H13 | L2ex2-4 |
| methyl-thiophene-ethynyl-nC5H11 | L2ex2-5 |

-continued
| | $R_{51}$ |
|---|---|
| L2ex2-6 | 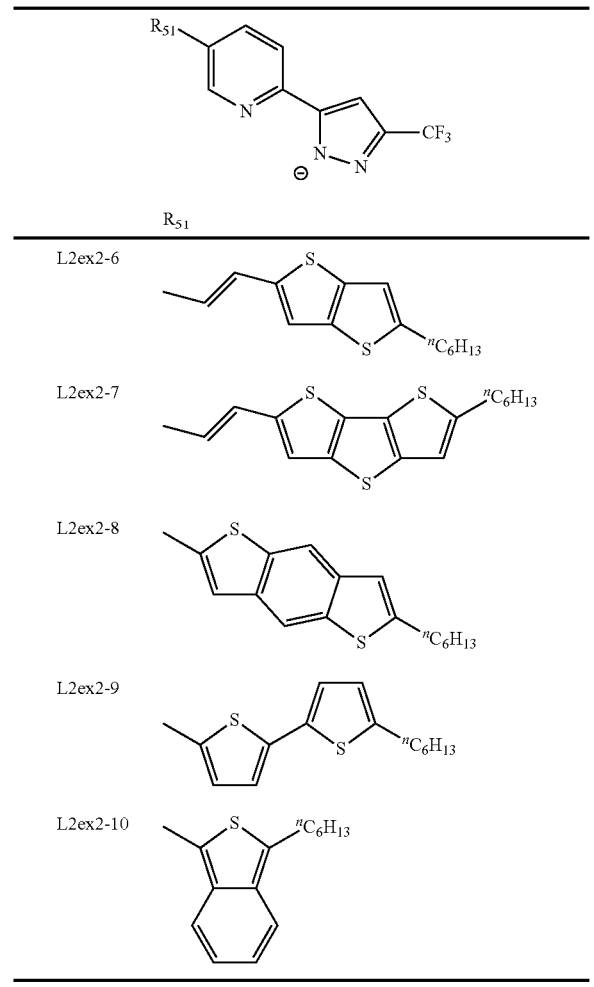 |
| L2ex2-7 | |
| L2ex2-8 | |
| L2ex2-9 | |
| L2ex2-10 | |
| | $R_{52}$ |
|---|---|
| L2ex3-1 | |
| L2ex3-2 | |
| L2ex3-3 | |
-continued
| | $R_{52}$ |
|---|---|
| L2ex3-4 | 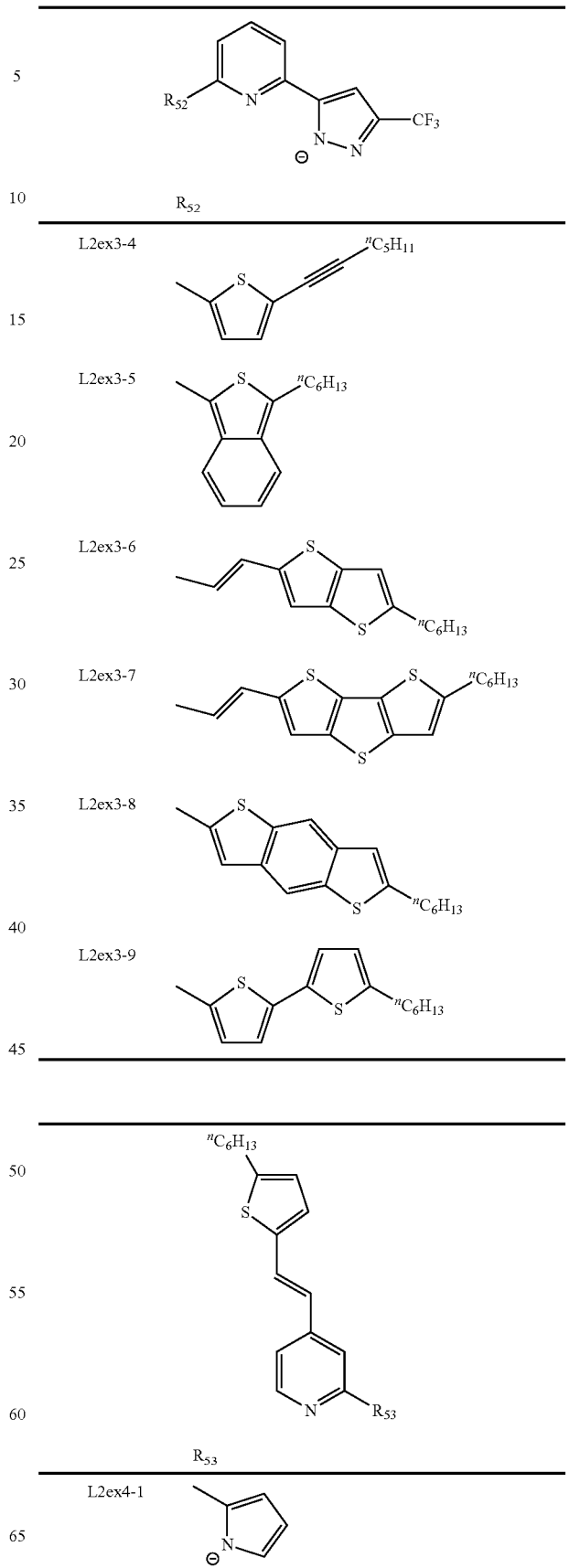 |
| L2ex3-5 | |
| L2ex3-6 | |
| L2ex3-7 | |
| L2ex3-8 | |
| L2ex3-9 | |
| | $R_{53}$ |
|---|---|
| L2ex4-1 | |

| | $R_{53}$ |
|---|---|
| L2ex4-2 | 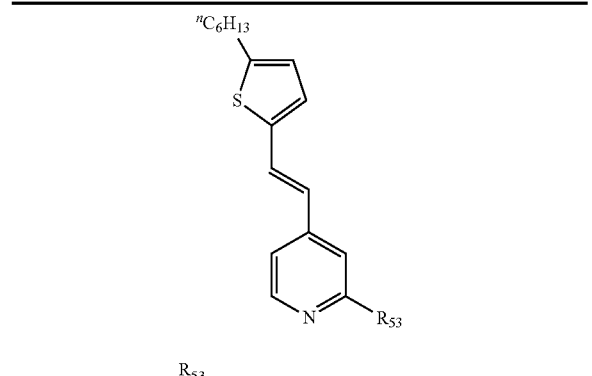 |
| L2ex4-3 | |
| L2ex4-4 | |
| L2ex4-5 | |
| L2ex4-6 | |
| | $R_{53}$ |
|---|---|
| L2ex4-7 | 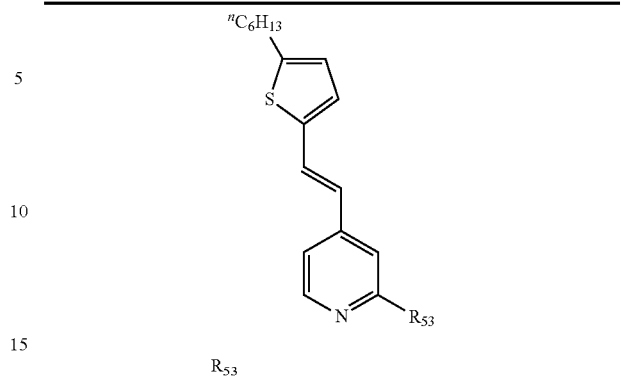 |
| L2ex4-8 | |
| L2ex4-9 | |
| L2ex4-10 | |
| L2ex4-11 | |
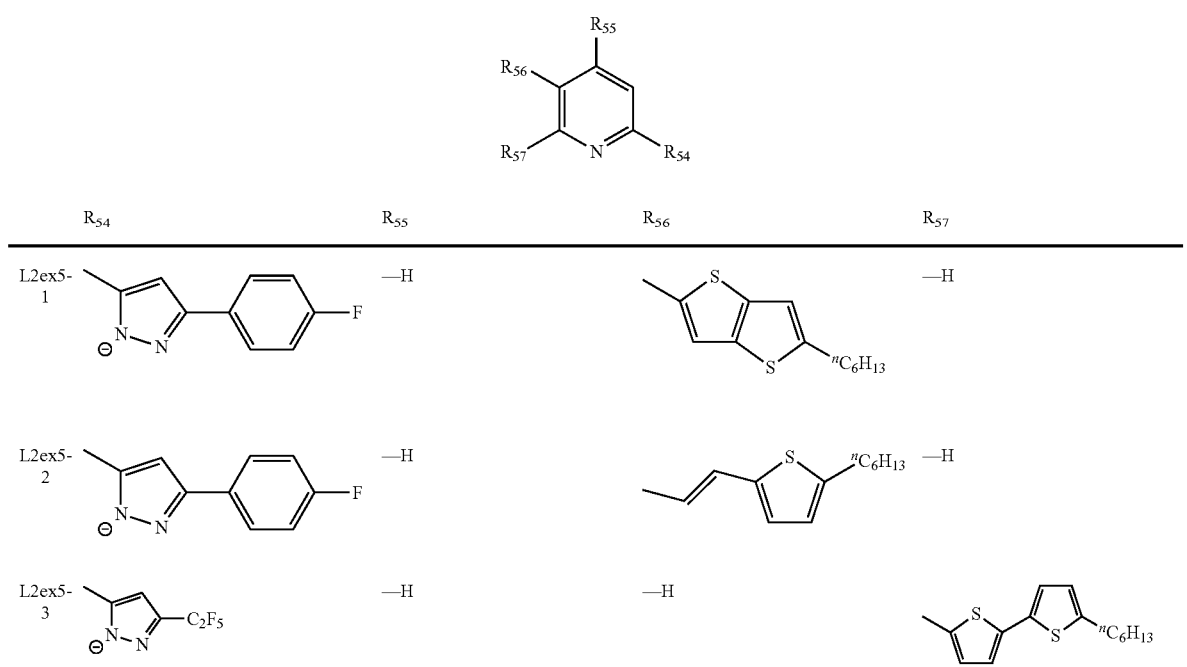
| | $R_{54}$ | $R_{55}$ | $R_{56}$ | $R_{57}$ |
|---|---|---|---|---|
| L2ex5-1 | | —H | | —H |
| L2ex5-2 | | —H | | —H |
| L2ex5-3 | | —H | —H | |

-continued
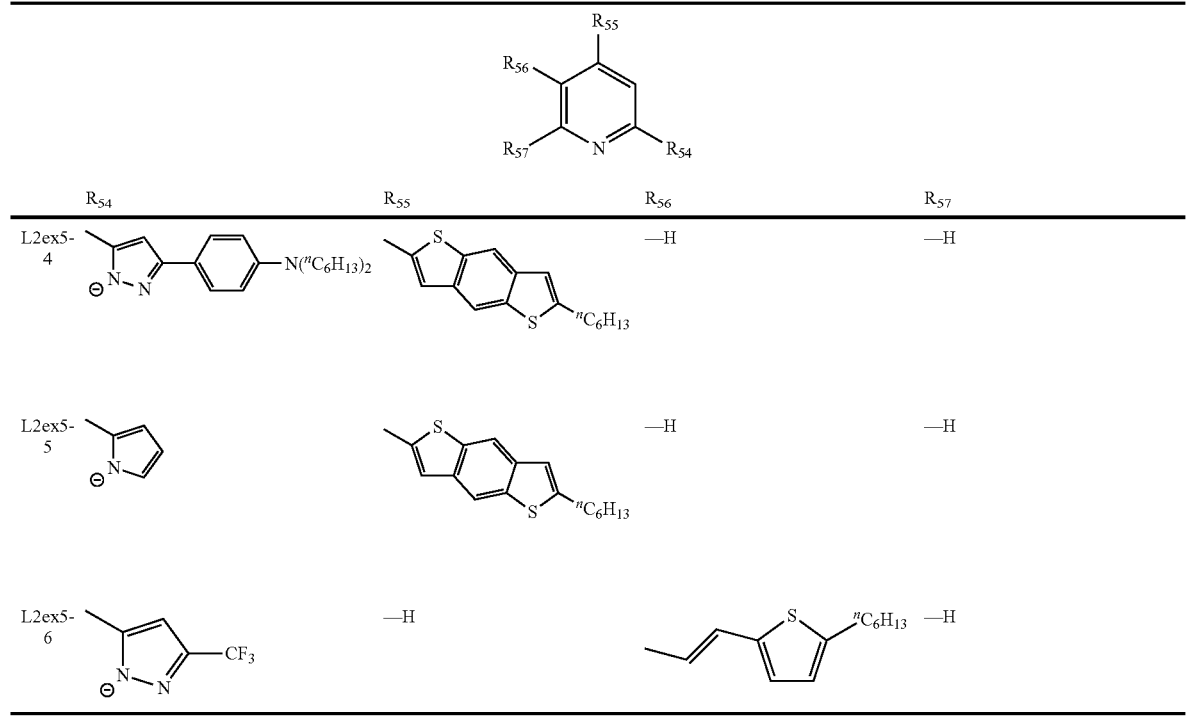
Specific examples of the terdentate ligand containing the rings Za, Zb and Zc are shown below, but the present invention is not limited to these.
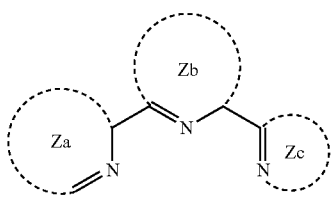
| Ligand | Za | Zb | Zc |
|---|---|---|---|
| B-2-1 | 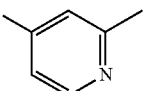 | 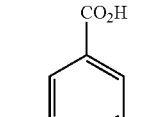 | 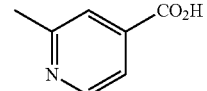 |
| B-2-2 | 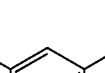 | 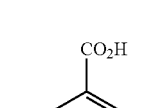 | 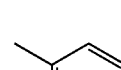 |
| B-2-3 |  |  |  |

-continued
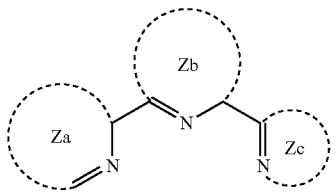
| Ligand | Za | Zb | Zc |
|---|---|---|---|
| B-2-4 | | | |
| B-2-5 | | | |
| B-2-6 | | | |
| B-2-7 | | | |
| B-2-8 | | | |
| B-2-9 | | | |
| B-2-10 | | | |

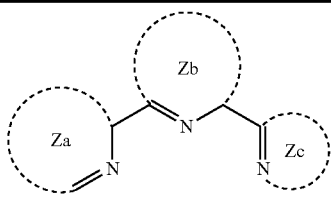

| Ligand | Za | Zb | Zc |
|---|---|---|---|
| B-2-11 | HO₂C-pyridine-Me | CO₂H-dimethylpyridine | Me-isoquinoline |
| B-2-12 | HO₂C-quinoline-Me | dimethylpyridine | Me-quinoline-CO₂H |
| B-2-13 | HO₂C-pyridine-Me | PO₃H₂-dimethylpyridine | Me-pyridine-CO₂H |
| B-2-14 | HO₂C-vinyl-pyridine-Me | CO₂H-dimethylpyridine | Me-pyridine-vinyl-CO₂H |
| B-2-15 | HO₂C-vinyl-pyridine-Me | dimethylpyridine | Me-pyridine-vinyl-CO₂H |
| B-2-16 | HO₂C-vinyl-pyridine-Me | CO₂H-vinyl-dimethylpyridine | Me-pyridine-vinyl-CO₂H |
| B-2-17 | HO₂C-thiophene-pyridine-Me | dimethylpyridine | Me-pyridine-thiophene-CO₂H |
| B-2-18 | HO₂C-pyrimidine-Me | dimethylpyridine | Me-pyrimidine-CO₂H |
| B-2-19 | HO₂C-vinyl-pyrimidine-Me | dimethylpyridine | Me-pyrimidine-vinyl-CO₂H |

-continued

| Ligand | Za | Zb | Zc |
|---|---|---|---|
| B-2-20 | HO2C-pyridine-methyl | triazine dimethyl | methyl-pyridine-CO2H |
| B-2-21 | HO2C-thiophene-pyridine-methyl | HO2C-thiophene-dimethylpyridine | methyl-pyridine-thiophene-CO2H |
| B-2-22 | HO2C-C(CN)=CH-methylpyridine | HO2C-C(CN)=CH-dimethylpyridine | methyl-pyridine |

Specific examples of the metal complex dye represented by Formula (I) according to the present invention are shown below, but the present invention is not limited to these.

Note that the specific examples of the metal complex dye represented by Formula (IA) are also shown below.

The structures of the monodentate ligands were shown at the end thereof.

| Dye No. | Zd—Ze | $Z^1$ | CI |
|---|---|---|---|
| D-1-1a | L2ex1-1 | Zex7 | $(H^+)_3$ |
| D-1-1h | L2ex1-1 | Zex7 | $(H^+)_2(K^+)$ |
| D-1-1i | L2ex1-1 | Zex7 | $(H^+)(K^+)_2$ |
| D-1-1j | L2ex1-1 | Zex7 | $(K^+)_3$ |
| D-1-1k | L2ex1-1 | Zex7 | $(H^+)_2(Cs^+)$ |
| D-1-1l | L2ex1-1 | Zex7 | $(H^+)(Cs^+)_2$ |

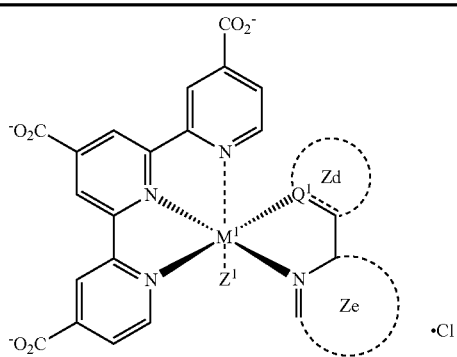

| Dye No. | Zd—Ze | $Z^1$ | CI |
|---|---|---|---|
| D-1-1m | L2ex1-1 | Zex7 | $(Cs^+)_3$ |
| D-1-1n | L2ex1-1 | Zex7 | $(H^+)_2(Li^+)$ |
| D-1-1o | L2ex1-1 | Zex7 | $(H^+)(Li^+)_2$ |
| D-1-2a | L2ex1-2 | Zex7 | $(H^+)_3$ |
| D-1-2e | L2ex1-2 | Zex7 | $(H^+)_2(Li^+)$ |
| D-1-2g | L2ex1-2 | Zex7 | $(H^+)_2(K^+)$ |
| D-1-2h | L2ex1-2 | Zex7 | $(H^+)_2(Cs^+)$ |
| D-1-3a | L2ex1-3 | Zex7 | $(H^+)_2(K^+)$ |
| D-1-4a | L2ex1-4 | Zex7 | $(H^+)_2(K^+)$ |
| D-1-5a | L2ex1-5 | Zex7 | $(H^+)_3$ |
| D-1-5e | L2ex1-5 | Zex7 | $(H^+)_2(Li^+)$ |
| D-1-5f | L2ex1-5 | Zex7 | $(H^+)(Li^+)_2$ |
| D-1-5j | L2ex1-5 | Zex7 | $(H^+)_2(K^+)$ |
| D-1-5k | L2ex1-5 | Zex7 | $(H^+)(K^+)_2$ |

-continued

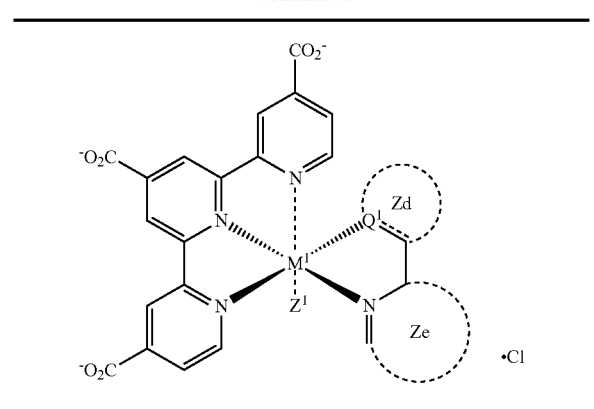

| Dye No. | Zd—Ze | $Z^1$ | Cl |
|---|---|---|---|
| D-1-5l | L2ex1-5 | Zex7 | $(K^+)_3$ |
| D-1-5m | L2ex1-5 | Zex7 | $(H^+)_2(Cs^+)$ |
| D-1-5n | L2ex1-5 | Zex7 | $(H^+)(Cs^+)_2$ |
| D-1-5o | L2ex1-5 | Zex7 | $(Cs^+)_3$ |

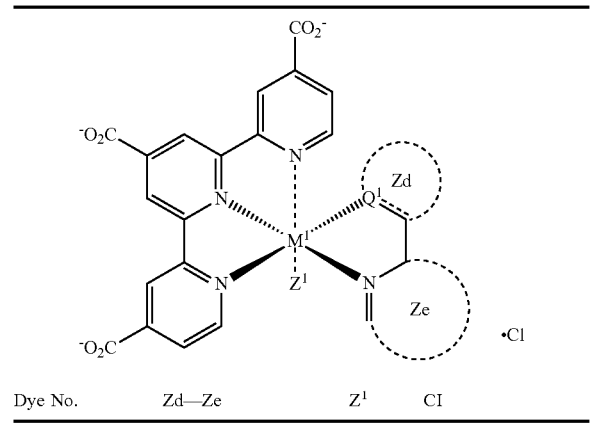

| Dye No. | Zd—Ze | $Z^1$ | Cl |
|---|---|---|---|
| D-1-6a | L2ex1-6 | Zex7 | $(H^+)_3$ |
| D-1-6e | L2ex1-6 | Zex7 | $(H^+)_2(Li^+)$ |
| D-1-6g | L2ex1-6 | Zex7 | $(H^+)_2(K^+)$ |
| D-1-6h | L2ex1-6 | Zex7 | $(H^+)_2(Cs^+)$ |
| D-1-7a | L2ex1-8 | Zex7 | $(H^+)_3$ |
| D-1-7e | L2ex1-8 | Zex7 | $(H^+)_2(Li^+)$ |
| D-1-7f | L2ex1-8 | Zex7 | $(H^+)(Li^+)_2$ |
| D-1-7i | L2ex1-8 | Zex7 | $(H^+)_2(K^+)$ |
| D-1-7j | L2ex1-8 | Zex7 | $(H^+)(K^+)_2$ |
| D-1-7k | L2ex1-8 | Zex7 | $(H^+)_2(Cs^+)$ |
| D-1-7l | L2ex1-8 | Zex7 | $(H^+)(Cs^+)_2$ |
| D-1-8a | L2ex1-9 | Zex7 | $(H^+)_3$ |
| D-1-8e | L2ex1-9 | Zex7 | $(H^+)_2(Li^+)$ |
| D-1-8f | L2ex1-9 | Zex7 | $(H^+)(Li^+)_2$ |
| D-1-8i | L2ex1-9 | Zex7 | $(H^+)_2(K^+)$ |
| D-1-8j | L2ex1-9 | Zex7 | $(H^+)(K^+)_2$ |
| D-1-8k | L2ex1-9 | Zex7 | $(H^+)_2(Cs^+)$ |
| D-1-8l | L2ex1-9 | Zex7 | $(H^+)(Cs^+)_2$ |
| D-1-9a | L2ex1-11 | Zex7 | $(H^+)_3$ |
| D-1-9f | L2ex1-11 | Zex7 | $(H^+)_2(K^+)$ |
| D-1-9g | L2ex1-11 | Zex7 | $(H^+)(K^+)_2$ |
| D-1-9h | L2ex1-11 | Zex7 | $(H^+)_2(Cs^+)$ |
| D-1-9i | L2ex1-11 | Zex7 | $(H^+)(Cs^+)_2$ |
| D-1-9j | L2ex1-11 | Zex7 | $(H^+)_2(Li^+)$ |
| D-1-9k | L2ex1-11 | Zex7 | $(H^+)(Li^+)_2$ |

| Dye No. | Zd—Ze | $Z^1$ | Cl |
|---|---|---|---|
| D-1-10d | L2ex1-12 | Zex7 | $(H^+)_2(K^+)$ |
| D-1-11a | L2ex1-13 | Zex7 | $(H^+)_2(K^+)$ |
| D-1-11d | L2ex1-13 | Zex7 | $(H^+)(K^+)_2$ |
| D-1-12a | L2ex1-16 | Zex7 | $(H^+)_3$ |
| D-1-12g | L2ex1-16 | Zex7 | $(H^+)_2(K^+)$ |
| D-1-12h | L2ex1-16 | Zex7 | $(H^+)(K^+)_2$ |
| D-1-12i | L2ex1-16 | Zex7 | $(H^+)_2(Cs^+)$ |
| D-1-12j | L2ex1-16 | Zex7 | $(H^+)(Cs^+)_2$ |
| D-1-12k | L2ex1-16 | Zex7 | $(H^+)_2(Li^+)$ |
| D-1-12l | L2ex1-16 | Zex7 | $(H^+)(Li^+)_2$ |
| D-1-13a | L2ex1-18 | Zex7 | $(H^+)_3$ |
| D-1-13b | L2ex1-18 | Zex7 | $(H^+)_2(K^+)$ |
| D-1-13c | L2ex1-18 | Zex7 | $(H^+)(K^+)_2$ |
| D-1-13d | L2ex1-18 | Zex7 | $(K^+)_3$ |
| D-1-13f | L2ex1-18 | Zex7 | $(H^+)_2(Cs^+)$ |
| D-1-13g | L2ex1-18 | Zex7 | $(H^+)(Cs^+)_2$ |
| D-1-13h | L2ex1-18 | Zex7 | $(H^+)_2(Li^+)$ |
| D-1-13i | L2ex1-18 | Zex7 | $(H^+)(Li^+)_2$ |
| D-1-14a | L2ex1-20 | Zex7 | $(H^+)_3$ |
| D-1-14h | L2ex1-20 | Zex7 | $(H^+)_2(K^+)$ |
| D-1-14i | L2ex1-20 | Zex7 | $(H^+)(K^+)_2$ |
| D-1-14j | L2ex1-20 | Zex7 | $(H^+)_2(Cs^+)$ |
| D-1-14k | L2ex1-20 | Zex7 | $(H^+)(Cs^+)_2$ |
| D-1-14l | L2ex1-20 | Zex7 | $(H^+)_2(Li^+)$ |
| D-1-14m | L2ex1-20 | Zex7 | $(H^+)(Li^+)_2$ |

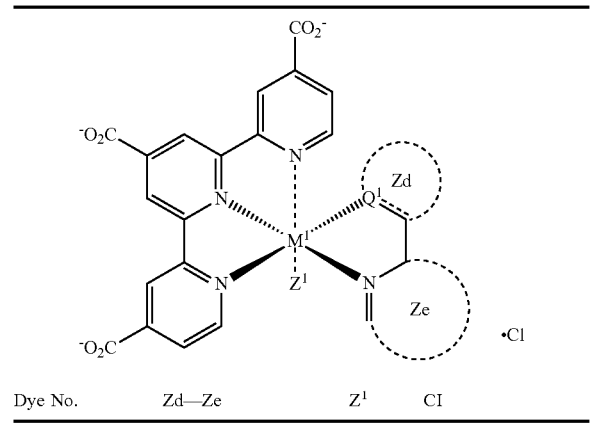

| Dye No. | Zd—Ze | $Z^1$ | Cl |
|---|---|---|---|
| D-1-15a | L2ex1-21 | Zex7 | $(H^+)_3$ |
| D-1-15b | L2ex1-21 | Zex7 | $(H^+)_2(Li^+)$ |
| D-1-15c | L2ex1-21 | Zex7 | $(H^+)(Li^+)_2$ |
| D-1-15f | L2ex1-21 | Zex7 | $(H^+)_2(K^+)$ |
| D-1-15g | L2ex1-21 | Zex7 | $(H^+)(K^+)_2$ |
| D-1-15h | L2ex1-21 | Zex7 | $(H^+)_2(Cs^+)$ |
| D-1-15i | L2ex1-21 | Zex7 | $(H^+)(Cs^+)_2$ |
| D-1-16a | L2ex2-1 | Zex7 | $(H^+)_3$ |
| D-1-16g | L2ex2-1 | Zex7 | $(H^+)_2(K^+)$ |
| D-1-16h | L2ex2-1 | Zex7 | $(H^+)(K^+)_2$ |
| D-1-16i | L2ex2-1 | Zex7 | $(H^+)_2(Cs^+)$ |
| D-1-16j | L2ex2-1 | Zex7 | $(H^+)(Cs^+)_2$ |
| D-1-16k | L2ex2-1 | Zex7 | $(H^+)_2(Li^+)$ |

-continued

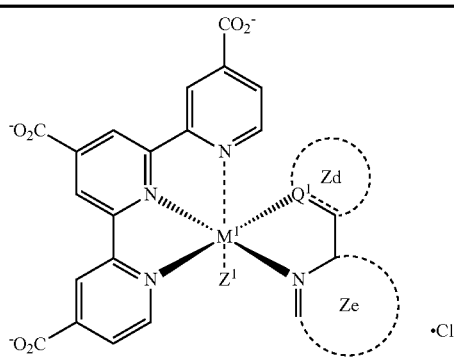

| Dye No. | Zd—Ze | Z¹ | Cl |
|---|---|---|---|
| D-1-16l | L2ex2-1 | Zex7 | $(H^+)(Li^+)_2$ |
| D-1-18a | L2ex3-1 | Zex7 | $(H^+)_3$ |
| D-1-18b | L2ex3-1 | Zex7 | $(H^+)_2(K^+)$ |
| D-1-18c | L2ex3-1 | Zex7 | $(H^+)(K^+)_2$ |
| D-1-18d | L2ex3-1 | Zex7 | $(K^+)_3$ |
| D-1-18f | L2ex3-1 | Zex7 | $(H^+)_2(Cs^+)$ |
| D-1-19a | L2ex4-1 | Zex7 | $(H^+)(Li^+)_2$ |
| D-1-21a | L2ex4-3 | Zex7 | $(H^+)_2(K^+)$ |
| D-1-22a | L2ex4-6 | Zex7 | $(H^+)_2(K^+)$ |
| D-1-23a | L2ex4-7 | Zex7 | $(H^+)_3$ |
| D-1-23b | L2ex4-7 | Zex7 | $(H^+)(K^+)_2$ |
| D-1-23e | L2ex4-7 | Zex7 | $(H^+)_2(Li^+)$ |
| D-1-23g | L2ex4-7 | Zex7 | $(H^+)_2(K^+)$ |
| D-1-23h | L2ex4-7 | Zex7 | $(H^+)_2(Cs^+)$ |
| D-1-24a | L2ex4-8 | Zex7 | $(H^+)_3$ |
| D-1-25a | L2ex4-10 | Zex7 | $(H^+)(Li^+)_2$ |

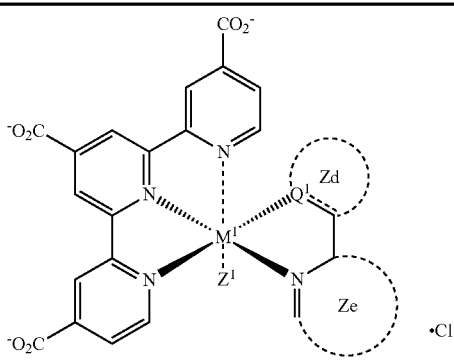

| Dye No. | Zd—Ze | Z¹ | Cl |
|---|---|---|---|
| D-1-26a | L2ex4-11 | Zex7 | $(H^+)_3$ |
| D-1-26h | L2ex4-11 | Zex7 | $(H^+)_2(K^+)$ |
| D-1-26i | L2ex4-11 | Zex7 | $(H^+)(K^+)_2$ |
| D-1-26j | L2ex4-11 | Zex7 | $(K^+)_3$ |
| D-1-26k | L2ex4-11 | Zex7 | $(H^+)_2(Cs^+)$ |
| D-1-26l | L2ex4-11 | Zex7 | $(H^+)(Cs^+)_2$ |
| D-1-26m | L2ex4-11 | Zex7 | $(Cs^+)_3$ |
| D-1-26n | L2ex4-11 | Zex7 | $(H^+)_2(Li^+)$ |
| D-1-26o | L2ex4-11 | Zex7 | $(H^+)(Li^+)_2$ |
| D-1-27a | L2ex4-4 | Zex7 | $(H^+)_3$ |
| D-1-28a | L2ex1-1 | Zex1 | $(H^+)_2(K^+)$ |
| D-1-29a | L2ex1-1 | Zex8 | $(H^+)_2(K^+)$ |
| D-1-30a | L2ex1-1 | Zex9 | $(H^+)_2(K^+)$ |
| D-1-32a | L2ex1-1 | Zex5 | $(H^+)_3$ |
| D-1-32b | L2ex1-1 | Zex5 | $(H^+)_2(Li^+)$ |
| D-1-32d | L2ex1-1 | Zex5 | $(H^+)_2(K^+)$ |
| D-1-32e | L2ex1-1 | Zex5 | $(H^+)(K^+)_2$ |
| D-1-32f | L2ex1-1 | Zex5 | $(H^+)_2(Cs^+)$ |
| D-1-33a | L2ex1-1 | Zex10 | $(H^+)_2(K^+)$ |
| D-1-34a | L2ex1-1 | Zex4 | $(H^+)_2(K^+)$ |
| D-1-35a | L2ex4-1 | Zex7 | $(H^+)_3$ |

-continued

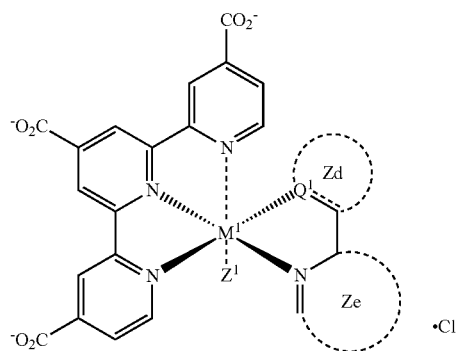

| Dye No. | Zd—Ze | Z¹ | Cl |
|---|---|---|---|
| D-1-35b | L2ex4-1 | Zex7 | $(H^+)_2(Li^+)$ |
| D-1-35d | L2ex4-1 | Zex7 | $(H^+)_2(K^+)$ |
| D-1-35e | L2ex4-1 | Zex7 | $(H^+)(K^+)_2$ |
| D-1-35f | L2ex4-1 | Zex7 | $(H^+)_2(Cs^+)$ |

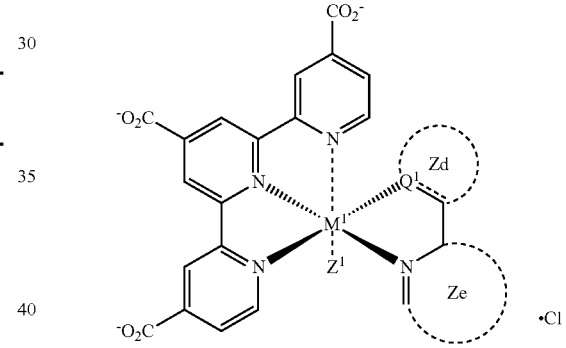

| Dye No. | Zd—Ze | Z¹ | Cl |
|---|---|---|---|
| D-1-36a | L2ex4-9 | Zex7 | $(H^+)_3$ |
| D-1-36b | L2ex4-9 | Zex7 | $(H^+)_2(Li^+)$ |
| D-1-36d | L2ex4-9 | Zex7 | $(H^+)_2(K^+)$ |
| D-1-36e | L2ex4-9 | Zex7 | $(H^+)(K^+)_2$ |
| D-1-36f | L2ex4-9 | Zex7 | $(H^+)_2(Cs^+)$ |
| D-1-37a | L2ex4-10 | Zex7 | $(H^+)_3$ |
| D-1-37b | L2ex4-10 | Zex7 | $(H^+)_2(Li^+)$ |
| D-1-37d | L2ex4-10 | Zex7 | $(H^+)_2(K^+)$ |
| D-1-37e | L2ex4-10 | Zex7 | $(H^+)(K^+)_2$ |
| D-1-37f | L2ex4-10 | Zex7 | $(H^+)_2(Cs^+)$ |
| D-1-38a | L2ex1-22 | Zex7 | $(H^+)_3$ |
| D-1-38h | L2ex1-22 | Zex7 | $(H^+)_2(K^+)$ |
| D-1-38i | L2ex1-22 | Zex7 | $(H^+)(K^+)_2$ |
| D-1-38j | L2ex1-22 | Zex7 | $(K^+)_3$ |
| D-1-38k | L2ex1-22 | Zex7 | $(H^+)_2(Cs^+)$ |
| D-1-38l | L2ex1-22 | Zex7 | $(H^+)(Cs^+)_2$ |
| D-1-38m | L2ex1-22 | Zex7 | $(Cs^+)_3$ |
| D-1-38n | L2ex1-22 | Zex7 | $(H^+)_2(Li^+)$ |
| D-1-38o | L2ex1-22 | Zex7 | $(H^+)(Li^+)$ |
| D-1-43b | L2ex1-28 | Zex7 | $(H^+)_2(K^+)$ |

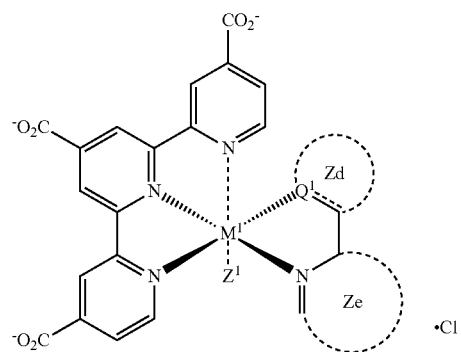

| Dye No | Zd—Ze | $Z^1$ | Cl |
|---|---|---|---|
| D-1-44b | L2ex1-30 | Zex7 | $(H^+)_2(K^+)$ |
| D-1-45a | L2ex1-24 | Zex7 | $(H^+)_3$ |
| D-1-45h | L2ex1-24 | Zex7 | $(H^+)_2(K^+)$ |
| D-1-45i | L2ex1-24 | Zex7 | $(H^+)(K^+)_2$ |
| D-1-45j | L2ex1-24 | Zex7 | $(K^+)_3$ |
| D-1-45k | L2ex1-24 | Zex7 | $(H^+)_2(Cs^+)$ |
| D-1-45l | L2ex1-24 | Zex7 | $(H^+)(Cs^+)_2$ |
| D-1-45m | L2ex1-24 | Zex7 | $(Cs^+)_3$ |
| D-1-45n | L2ex1-24 | Zex7 | $(H^+)_2(Li^+)$ |
| D-1-45o | L2ex1-24 | Zex7 | $(H^+)(Li^+)_2$ |
| D-1-46a | L2ex1-25 | Zex7 | $(H^+)_3$ |
| D-1-46c | L2ex1-25 | Zex7 | $(H^+)_2(Li^+)$ |
| D-1-46e | L2ex1-25 | Zex7 | $(H^+)_2(K^+)$ |
| D-1-46f | L2ex1-25 | Zex7 | $(H^+)(K^+)_2$ |
| D-1-46g | L2ex1-25 | Zex7 | $(H^+)_2(Cs^+)$ |

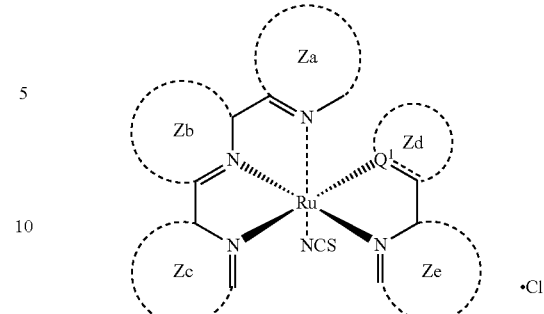

| Dye No. | Za—Zb—Zc | Zd—Ze | Cl |
|---|---|---|---|
| D-2-1a | Bex5 | L2ex1-1 | $(H^+)_3$ |
| D-2-1e | Bex5 | L2ex1-1 | $(H^+)_2(Li^+)$ |
| D-2-1g | Bex5 | L2ex1-1 | $(H^+)_2(K^+)$ |
| D-2-1h | Bex5 | L2ex1-1 | $(H^+)(K^+)_2$ |
| D-2-1i | Bex5 | L2ex1-1 | $(H^+)_2(Cs^+)$ |
| D-2-2a | Bex1 | L2ex1-8 | $(H^+)(K^+)$ |
| D-2-3a | Bex3 | L2ex1-15 | $(H^+)(K^+)$ |
| D-2-6a | Bex3 | L2ex3-9 | $(H^+)(K^+)$ |
| D-2-7a | Bex6 | L2ex1-21 | $(H^+)_2(K^+)$ |
| D-2-8a | Bex6 | L2ex1-22 | $(H^+)_3$ |
| D-2-8c | Bex6 | L2ex1-22 | $(H^+)_2(Li^+)$ |
| D-2-8e | Bex6 | L2ex1-22 | $(H^+)_2(K^+)$ |
| D-2-8f | Bex6 | L2ex1-22 | $(H^+)(K^+)_2$ |
| D-2-8g | Bex6 | L2ex1-22 | $(H^+)_2(Cs^+)$ |
| D-2-9a | Bex5 | L2ex1-22 | $(H^+)_3$ |
| D-2-9c | Bex5 | L2ex1-22 | $(H^+)_2(Li^+)$ |
| D-2-9e | Bex5 | L2ex1-22 | $(H^+)_2(K1)$ |
| D-2-9f | Bex5 | L2ex1-22 | $(H^+)(K^+)_2$ |
| D-2-9g | Bex5 | L2ex1-22 | $(H^+)_2(Cs^+)$ |
| D-2-10a | Bex1 | L2ex1-1 | $(H^+)_2$ |
| D-2-10c | Bex1 | L2ex1-1 | $(H^+)(Li^+)$ |
| D-2-10e | Bex1 | L2ex1-1 | $(H^+)(K^+)$ |
| D-2-10f | Bex1 | L2ex1-1 | $(K^+)_2$ |
| D-2-10g | Bex1 | L2ex1-1 | $(H^+)(Cs^+)$ |

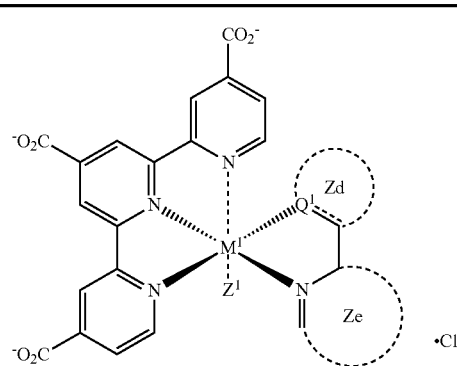

| Dye No. | Zd—Ze | $Z^1$ | Cl |
|---|---|---|---|
| D-1-53a | L2ex1-23 | Zex7 | $(H^+)_3$ |
| D-1-53b | L2ex1-23 | Zex7 | $(H^+)_2(Li^+)$ |
| D-1-53d | L2ex1-23 | Zex7 | $(H^+)_2(K^+)$ |
| D-1-53e | L2ex1-23 | Zex7 | $(H^+)(K^+)_2$ |
| D-1-53f | L2ex1-23 | Zex7 | $(H^+)_2(Cs^+)$ |
| D-1-54a | L2ex1-33 | Zex7 | $(H^+)_3$ |

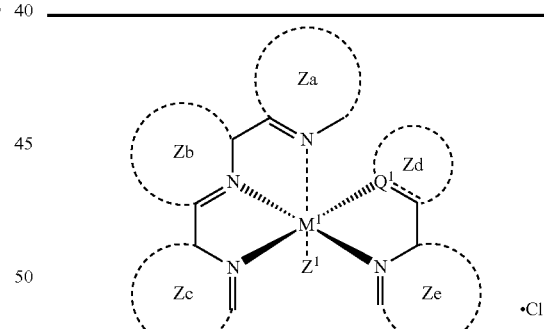

| Dye No. | Za—Zb—Zc | Zd—Ze | $Z^1$ | $M^1$ | Cl |
|---|---|---|---|---|---|
| D-3-1a | Bex2 | L2ex1-1 | Zex7 | Os | $(H^+)_3$ |
| D-3-1g | Bex2 | L2ex1-1 | Zex7 | Os | $(H^+)_2(K^+)$ |
| D-3-1h | Bex2 | L2ex1-1 | Zex7 | Os | $(H^+)(K^+)_2$ |
| D-3-1i | Bex2 | L2ex1-1 | Zex7 | Os | $(H^+)_2(Cs^+)$ |
| D-3-1j | Bex2 | L2ex1-1 | Zex7 | Os | $(H^+)(Cs^+)_2$ |
| D-3-1k | Bex2 | L2ex1-1 | Zex7 | Os | $(H^+)_2(Li^+)$ |
| D-3-1l | Bex2 | L2ex1-1 | Zex7 | Os | $(H^+)(Li^+)_2$ |
| D-3-3a | Bex6 | L2ex1-16 | Zex3 | Os | $(H^+)(Li^+)_2$ |
| D-3-5a | Bex2 | L2ex1-1 | Zex2 | Ru | $(H^+)_2$ |
| D-3-5b | Bex2 | L2ex1-1 | Zex2 | Ru | $(H^+)_2(Li^+)$ |
| D-3-5d | Bex2 | L2ex1-1 | Zex2 | Ru | $(H^+)_2(K^+)$ |
| D-3-5e | Bex2 | L2ex1-1 | Zex2 | Ru | $(H^+)_2(Cs^+)$ |
| D-3-6a | Bex2 | L2ex1-1 | Zex6 | Ru | $(H^+)_2(K^+)$ |

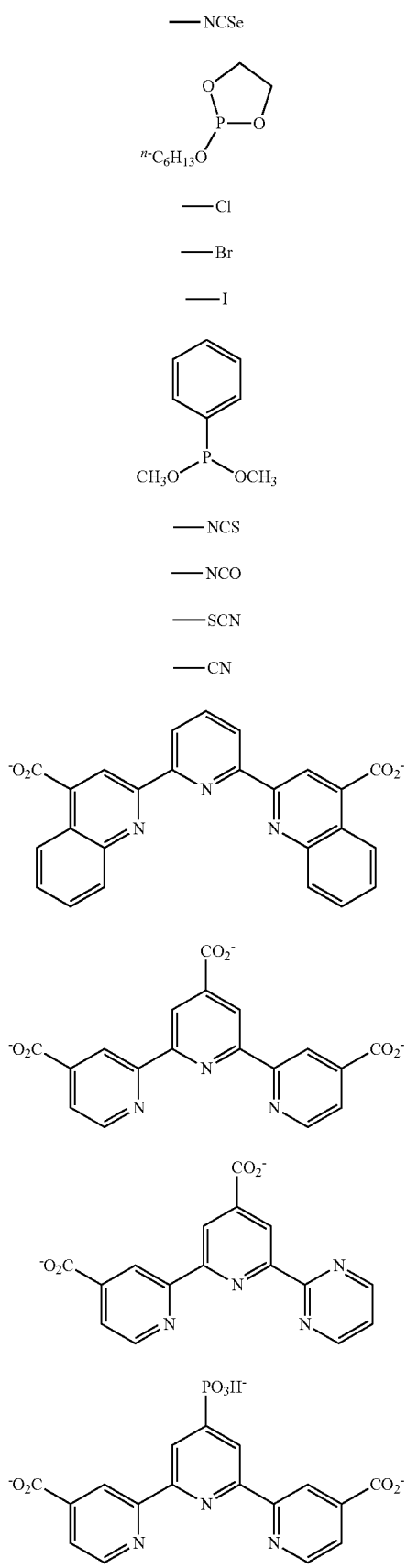
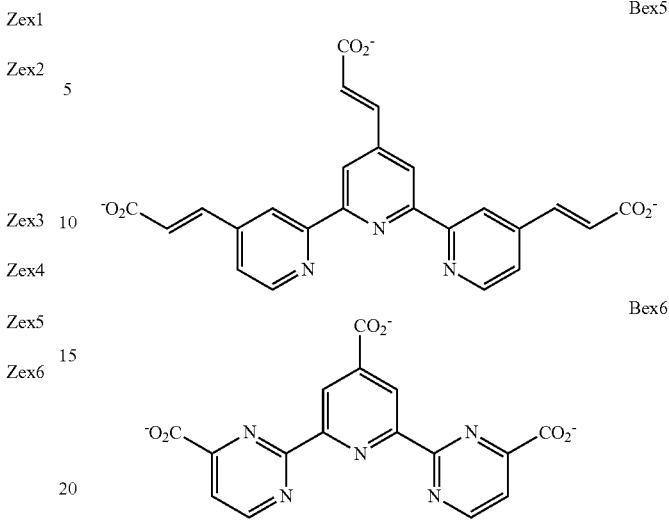

The metal complex dye represented by Formula (I) according to the present invention can be synthesized by methods described in US 2010/0258175 A1, Japanese Patent No. 4298799, and Angew. Chem. Int. Ed., 2011, 50, 2054-2058, methods described in references cited in the literatures, or methods according to these methods.

The metal complex dye of present invention has a maximum absorption wavelength in a solution in a range of preferably from 300 to 1,000 nm, more preferably from 350 to 950 nm, and especially preferably from 370 to 900 nm.

In the present invention, the metal complex dye of the present invention and another dye may be used in combination.

The dye to be used in combination includes: a Ru complex dye described in JP-T-7-500630 (in particular, dyes synthesized in Examples 1 to 19 described in from line 5 on left lower column on page 5 to line 7 on right upper column on page 7) (the term "JP-T" means a published Japanese translation of a PCT patent application), a Ru complex dye described in JP-T-2002-512729 (in particular, dyes synthesized in Examples 1 to 16 described in line 3 from the bottom of page 20 to line 23 on page 29), a Ru complex dye described in JP-A-2001-59062 (in particular, dyes described in paragraph Nos. 0087 to 0104), a Ru complex dye described in JP-A-2001-6760 (in particular, dyes described in paragraph Nos. 0093 to 0102), a Ru complex dye described in JP-A-2001-253894 (in particular, dyes described in paragraph Nos. 0009 to 0010), a Ru complex dye described in JP-A-2003-212851 (in particular, dyes described in paragraph No. 0005), a Ru complex dye described in WO 2007/91525 pamphlet (in particular, dyes described in paragraph No. [0067]), a Ru complex dye described in JP-A-2001-291534 (in particular, dyes described in paragraph Nos. 0120 to 0144), a Ru complex dye described in JP-A-2012-012570 (in particular, dyes described in paragraph Nos. 0095 to 0103), a Ru complex dye described in WO 2013/47615 pamphlet (in particular, dyes described in paragraph Nos. [0078] to [0082]), a squarylium cyanine dye described in JP-A-11-214730 (in particular, dyes described in paragraph Nos. 0036 to 0047), a squarylium cyanine dye described in JP-A-2012-144688 (in particular, dyes described in paragraph Nos. 0039 to 0046 and 0054 to 0060), a squarylium cyanine dye described in JP-A-2012-84503 (in particular, dyes described in paragraph Nos. 0066 to 0076 and the like), an organic dye described in JP-A-2004-063274 (in particular, dyes described in paragraph Nos. 0017 to 0021), an organic dye described in JP-A-2005-123033 (in particular, dyes described in paragraph Nos. 0021 to 0028), an organic dye described in JP-A-2007-287694 (in particular, dyes described in paragraph Nos. 0091 to 0096), an organic dye described in JP-A-2008-71648 (in particular, dyes described in paragraph Nos. 0030 to 0034), an organic dye described in WO 2007/119525 pamphlet (in particular, dyes described in paragraph No. [0024]), a porphyrine dye described in Angew. Chem. Int. Ed., 49, 1 to 5 (2010), and a phthalocyanine dye described in Angew. Chem. Int. Ed., 46, 8358 (2007), or the like.

Preferable dyes to be used in combination include Ru complex dyes, squarylium cyanine dyes, or organic dyes.

In the case where the metal complex dye of the present invention and another dye are used in combination, a ratio of mass of the metal complex dye of the present invention/mass of another dye is preferably from 95/5 to 10/90, more preferably from 95/5 to 50/50, still more preferably from 95/5 to 60/40, particularly preferably from 95/5 to 65/35, and most preferably from 95/5 to 70/30.

—Electrically Conductive Support—

The electrically conductive support is preferably a support having electroconductivity by itself, such as a metal, or a glass or plastic support having an electrically-conductive film layer on the surface. As the plastic support, a transparent polymer film described in paragraph No. 0153 of JP-A-2001-291534 can be mentioned. As the support, in addition to the glass and plastic, ceramic (JP-A-2005-135902), an electrically-conductive resin (JP-A-2001-160425), or the like may be used. The electrically-conductive support may be provided with a light management function at the surface, and for example, the anti-reflective film in which a high refractive index film and a low refractive index oxide film are alternately laminated, as described in JP-A-2003-123859, and with a light guide function as described in JP-A-2002-260746.

The thickness of the electrically-conductive film layer is preferably 0.01 to 30 μm, more preferably 0.03 to 25 μm, and particularly preferably 0.05 to 20 μm.

It is preferable that the electrically conductive support is substantially transparent. The term "substantially transparent" means that the transmittance of light is 10% or more, preferably 50% or more, and particularly preferably 80% or more. As the transparent electrically conductive support, a support formed from glass or plastic and coated with an electrically conductive metal oxide is preferable. As the metal oxide, tin oxide is preferable, and indium-tin oxide and fluorine-doped oxide are particularly preferable. In this case, the coating amount of the electrically-conductive metal oxide is preferably 0.1 to 100 g, per square meter of the support made of glass or plastic. In the case of using a transparent electrically conductive support, it is preferable that light is incident from the support side.

—Semiconductor Fine Particles—

Regarding the semiconductor fine particles, fine particles of chalcogenides of metals (for example, oxides, sulfides and selenides), or fine-particles of perovskites may be used with preference. Preferred examples of the chalcogenides of metals include oxides of titanium, tin, zinc, tungsten, zirconium, hafnium, strontium, indium, cerium, yttrium, lanthanum, vanadium, niobium or tantalum, cadmium sulfide, and cadmium selenide. Preferred examples of the perovskites include strontium titanate, and calcium titanate. Among these, titanium oxide (titania), zinc oxide, tin oxide, and tungsten oxide are particularly preferred.

Examples of the crystal structure of titania include structures of anatase type, brookite type and rutile type, and anatase type and brookite type structures are preferred. A titania nanotube, nanowire, or nanorod may be mixed with titania fine-particles or may be used as a semiconductor electrode.

A particle size of the semiconductor fine-particles is expressed in terms of an average particle size using a diameter when a projected area is converted into a circle, and is preferably 0.001 to 1 μm as primary particles, and 0.01 to 100 μm as an average particle size of dispersions. Examples of the method for coating the semiconductor fine-particles on the electrically conductive support include a wet method, a dry method or other methods.

It is preferable to form a short circuit-preventing layer between the transparent electrically conductive film and the semiconductor layer (photoconductor layer), so as to prevent reverse current due to a direct contact between the electrolyte and the electrode. It is preferable to employ a spacer or a separator, so as to prevent contact between the photoelectrode and the counter electrode. It is preferable for the semiconductor fine-particles to have a large surface area, so that a large amount of dye can adsorb to the surface. For example, in a state of the semiconductor fine-particles being coated on the support, the surface area is preferably 10 times or more, and more preferably 100 times or more, relative to the projected surface area. The upper limit of this value is not particularly limited, and the upper limit is generally about 5,000 times. In general, as the thickness of the layer containing semiconductor fine particles increases, the amount of dye that can be carried per unit area increases, and therefore, the light absorption efficiency is increased. However, since the diffusion distance of generated electrons increases along, the loss due to charge recombination is also increased. Although a preferred thickness of the photoconductor layer being a semiconductor layer may vary with the utility of the element, the thickness is typically 0.1 to 100 μm. In the case of using the photoelectric conversion element for a dye-sensitized solar cell, the thickness of the semiconductor layer is preferably 1 to 50 μm, and more preferably 3 to 30 μm. The semiconductor fine-particles may be calcined after being applied on the support, at a temperature of 100 to 800° C. for 10 minutes to 10 hours, so as to bring about cohesion of the particles. When a glass support is used, the film-forming temperature is preferably 60 to 400° C.

The amount of coating of the semiconductor fine-particles per square meter of the support is preferably 0.5 to 500 g, and more preferably 5 to 100 g. The overall amount of use of the dye is preferably 0.01 to 100 millimoles, more preferably 0.1 to 50 millimoles, and particularly preferably 0.1 to 10 millimoles, per square meter of the support. In this case, the amount of use of the metal complex dye of the present invention is preferably set to 5% by mole or more. The amount of the dye adsorbed to the semiconductor fine-particles is preferably 0.001 to 1 millimole, and more preferably 0.1 to 0.5 millimoles, based on 1 g of the semiconductor fine-particles. When the amount of the dye is set to such a range, the sensitization effect in the semiconductor fine particles can be sufficiently obtained.

When the above dye is a salt, a counter ion of the above specific metal complex dye is not particularly limited. Examples thereof include an alkali metal ion and a quaternary ammonium ion.

After the dye has been adsorbed, the surface of the semiconductor fine-particles may be treated using amines. Preferred examples of the amines include pyridines (e.g., 4-tert-butylpyridine, and polyvinylpyridine). These may be used directly when the compounds are liquids, or may be used in a state of being dissolved in an organic solvent.

In the photoelectric conversion element (for example, a photoelectric conversion element 10) and the dye-sensitized solar cell (for example, dye-sensitized solar cell 20) according to the present invention, at least the metal complex dye of the present invention is used.

—Charge-Transfer Layer—

The charge transfer layer for use in the photoelectric conversion element of the present invention is a layer having a function to replenish electrons to the oxidized form of the dye, and it is provided between the light-receiving electrode and the counter electrode (an opposite electrode). The charge-transfer layer contains an electrolyte. Examples of the electrolyte include a liquid electrolyte having a redox pair dissolved in an organic solvent, a so-called gel electrolyte in which a liquid having a redox pair dissolved in an organic solvent is impregnated in a polymer matrix, and a molten salt containing a redox pair. In order to enhance photoelectric conversion efficiency, a liquid electrolyte is preferred. As a solvent of the liquid electrolyte, a nitrile compound, an ether compound, an ester compound, or the like, is used, and a nitrile compound is preferred, and acetonitrile and methoxypropionitrile are particularly preferred.

Examples of the redox pair include a combination of iodine and an iodide (preferably an iodide salt, or an iodide ionic liquid; more preferably lithium iodide, tetrabutylammonium iodide, tetrapropylammonium iodide, or methylpropylimidazolium iodide), a combination of an alkylviologen (for example, methylviologen chloride, hexylviologen bromide, or benzylviologen tetrafluoroborate) and a reductant thereof, a combination of a polyhydroxybenzene (for example, hydroquinone, naphthohydroquinone, or the like) and an oxidized form thereof, a combination of a divalent iron complex and a trivalent iron complex (for example, a combination of potassium ferricyanide and potassium ferrocyanide), and a combination of a divalent cobalt complex and a trivalent cobalt complex. Among these, a combination of iodine and an iodide, and a combination of a divalent cobalt complex and a trivalent cobalt complex, are preferred.

The cobalt complex is preferably a complex represented by the following Formula (CC).

Co(LL)ma(X)mb•CI  Formula (CC)

In Formula (CC), LL represents a bidentate or terdentate ligand. X represents a monodentate ligand. ma represents an integer of 0 to 3. mb represents an integer of 0 to 6. CI represents a counter ion in the case where the counter ion is necessary to neutralize an electric charge.

Examples of CI include those of CI in Formula (I).

LL is preferably a ligand represented by the following Formula (LC).

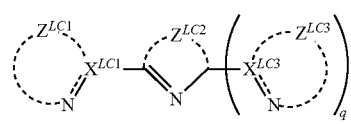

Formula (LC)

In Formula (LC), $X^{LC1}$ and $X^{LC3}$ each independently represent a carbon atom or a nitrogen atom. Herein, when $X^{LC1}$ is a carbon atom, the bond between $X^{LC1}$ and the N atom is a double bond ($X^{LC1}$=N). When $X^{LC3}$ is a carbon atom, the bond between $X^{LC3}$ and the N atom is a double bond ($X^{LC3}$=N). When $X^{LC1}$ is a nitrogen atom, the bond between $X^{LC1}$ and the N atom is a single bond ($X^{LC1}$—N). When $X^{LC3}$ is a nitrogen atom, the bond between $X^{LC3}$ and the N atom is a single bond ($X^{LC3}$—N).

$Z^{LC1}$, $Z^{LC2}$, and $Z^{LC3}$ each independently represent a group of nonmetallic atoms necessary to form a 5- or 6-membered ring. Each of $Z^{LC1}$, $Z^{LC2}$, and $Z^{LC3}$ may have a substituent, and may form a ring-closure together with an adjacent ring through a substituent. q represents 0 or 1. Examples of the substituent include the substituent T described later. Further, when q is 0, the carbon atom on a position at which $X^{LC3}$ bonds to a 5-membered ring or 6-membered ring formed by $Z^{LC2}$ bonds with a hydrogen atom or a substituent other than heterocyclic group formed by $Z^{LC3}$.

X is preferably a halogen ion.

The ligand represented by Formula (LC) is preferably a ligand represented by any one of the following Formulas (LC-1) to (LC-4).

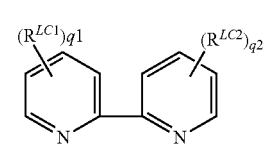

Formula (LC-1)

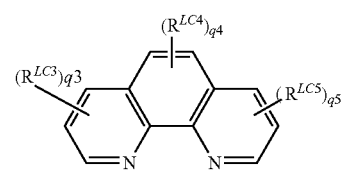

Formula (LC-2)

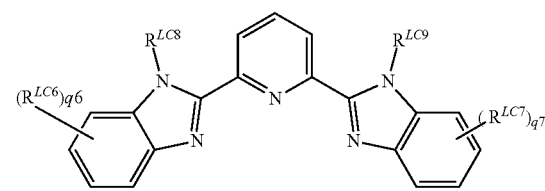

Formula (LC-3)

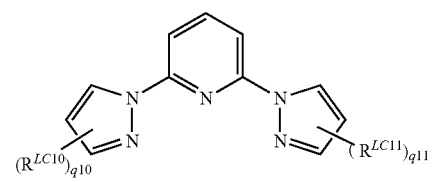

Formula (LC-4)

$R^{LC1}$ to $R^{LC11}$ each independently represent a substituent. q1, q2, q6, and q7 each independently represent an integer of 0 to 4. q3, q5, q10, and q11 each independently represent an integer of 0 to 3. q4 represents an integer of 0 to 2.

In Formulas (LC-1) to (LC-4), examples of the substituent $R^{LC1}$ to $R^{LC11}$ include an aliphatic group, an aromatic group, a heterocyclic group or the like. Specific examples of the substituent include an alkyl group, an alkoxy group, an alkylthio group, an aryl group, an aryloxy group, an arylthio group, and a heterocycle. Preferred examples include an alkyl group (for example, methyl, ethyl, n-butyl, n-hexyl, isobutyl, sec-butyl, t-butyl, n-dodecyl, cyclohexyl, or benzyl), an aryl group (for example, phenyl, tolyl, or naphthyl), an alkoxy group (for example, methoxy, ethoxy, isopropoxy, or butoxy), an alkylthio group (for example, methylthio, n-butylthio, n-hexylthio, or 2-ethylhexylthio), an aryloxy group (for example, phenoxy, or naphthoxy), an arylthio group (for example, phenylthio, or naphthylthio), and a heterocyclic group (for example, 2-thienyl, or 2-furyl).

Specific examples of the cobalt complex represented by Formula (LC) include the following complexes.

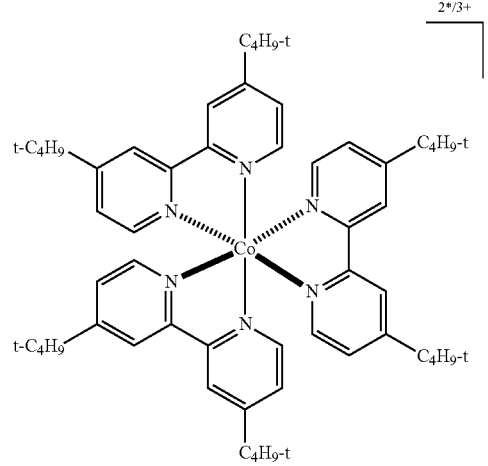

LL-1

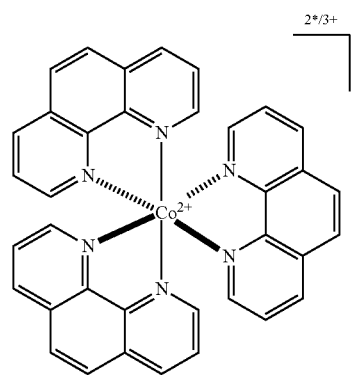

LL-2

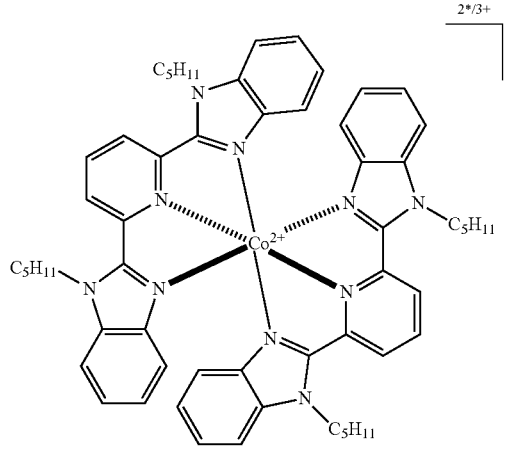

LL-3

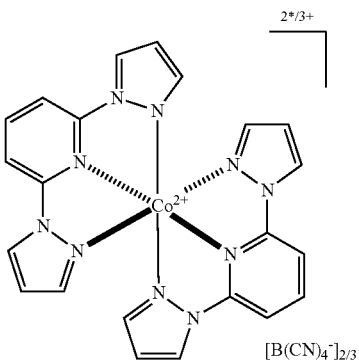

LL-4

In the case where iodine and an iodide are used in combination, as an electrolyte, it is preferred that a 5- or 6-membered-ring nitrogen-containing aromatic cation iodide salt is additionally used in combination with them.

Preferred examples of the organic solvent that dissolves these redox pairs include aprotic polar solvents (for example, acetonitrile, propylene carbonate, ethylene carbonate, dimethylformamide, dimethylsulfoxide, sulfolane, 1,3-dimethylimidazolinone, and 3-methyloxazolidinone). Examples of the polymer used for a matrix of a gel electrolyte include polyacrylonitrile, polyvinylidene fluoride, and the like. Examples of the molten salts include, for example, a molten salt to which fluidity at room temperature has been imparted by mixing lithium iodide and at least one kind of other lithium salt (for example, lithium acetate or lithium perchlorate) with polyethylene oxide. The amount of addition of the polymer in this case is 1 to 50% by mass. Furthermore, the electrolyte liquid may contain γ-butyrolactone, and this increases the diffusion efficiency of iodide ions, and thereby the conversion efficiency is enhanced.

Examples of the additives to the electrolyte include 4-tert-butylpyridine mentioned above, as well as aminopyridine-based compounds, benzimidazole-based compounds, aminotriazole-based compounds, aminothiazole-based compounds, imidazole-based compounds, aminotriazine-based compounds, urea derivatives, amide compounds, pyrimidine-based compounds, and heterocycles that do not contain nitrogen.

It is also preferable to employ a method of controlling the water content of the electrolyte liquid, in order to enhance the photoelectric conversion efficiency. Preferred examples of the method of controlling the water content include a method of controlling the concentration, and a method of adding a dehydrating agent. In order to reduce the toxicity of iodine, a clathrate compound of iodine with cyclodextrin may be used. Alternatively, a method of supplying moisture on a steady basis may be used. Furthermore, a cyclic amidine may be used; or an oxidation inhibitor, a hydrolysis inhibitor, a decomposition inhibitor or zinc iodide may be added.

A molten salt may also be used as the electrolyte, and preferred examples of the molten salt include an ionic liquid containing an imidazolium or triazolium type cation, an oxazolium-based salt, a pyridinium-based salt, a guanidium-based salt, and combinations of these. These cations may be used in combination with particular anions. Additives may be added to these molten salts. The molten salt may have a substituent having liquid crystalline properties. Furthermore, the quaternary ammonium salt-based molten salt may also be used.

Molten salts other than those described above include, for example, a molten salt to which fluidity at room temperature has been imparted by mixing lithium iodide and at least one kind of other lithium salt (for example, lithium acetate or lithium perchlorate) with polyethylene oxide.

The electrolyte may be quasi-solidified by adding a gelling agent to an electrolyte liquid including an electrolyte and a solvent, and gelling the electrolyte liquid thereby. Examples of the gelling agent include an organic compound having a molecular weight of 1000 or less, a Si-containing compound having a molecular weight in the range of 500 to 5000, an organic salt obtained from a particular acidic compound and a particular basic compound, a sorbitol derivative, and polyvinylpyridine.

Furthermore, a method of confining a matrix polymer, a crosslinking type polymer compound or monomer, a crosslinking agent, an electrolyte, and a solvent, in a polymer may be used.

Preferred examples of the matrix polymer include a polymer having a nitrogen-containing heterocyclic ring in a repeating unit in the main chain or in a side chain, and a crosslinked structure formed by reacting the polymer with an electrophilic compound; a polymer having a triazine structure, a polymer having a ureide structure, a polymer containing a liquid crystalline compound, a polymer having an ether bond, a polyvinylidene fluoride-based polymer, a methacrylate or acrylate-based polymer, a thermosetting resin, crosslinked polysiloxane, polyvinyl alcohol (PVA), a clathrate compound of polyalkylene glycol and dextrin, a system incorporated with an oxygen-containing or sulfur-containing polymer, and a naturally occurring polymer. An alkali-swellable polymer, a polymer having a cation moiety and a component capable of forming a charge transfer complex with iodine within one polymer molecule, or the like may be added to those matrix polymers.

A system containing, as a matrix polymer, a crosslinked polymer formed by reacting a bifunctional or higher-functional isocyanate as one component with a functional group such as a hydroxyl group, an amino group or a carboxyl group, may also be used. Furthermore, a crosslinked polymer by a hydrosilyl group and a double-bonded compound, a crosslinking method involving reacting polysulfonic acid, polycarboxylic acid or the like with a divalent or higher-valent metal ion compound, and the like may also be used.

Examples of the solvent that can be used with preference in combination with the quasi-solid electrolyte described above, include particular phosphates, a mixed solvent containing ethylene carbonate, a solvent having a particular relative permittivity, and the like. A liquid electrolyte solution may be retained in a solid electrolyte membrane or in pores, and preferred examples of the method include the usage of an electrically conductive polymer membrane, a fibrous solid, and a fabric-like solid such as filter.

A solid-state charge-transport layer, such as a p-type semiconductor or a hole-transporting material, for example, CuI or CuNCS, may also be used in place of a liquid electrolyte and a quasi-solid-state electrolyte as described above. Moreover, electrolytes described in Nature, vol. 486, p. 487 (2012) and the like may be used. For a solid charge-transport layer, an organic hole-transporting material may be used. Preferred examples of the hole-transport layer include electrically conductive polymers such as polythiophene, polyaniline, polypyrrole, and polysilane; a spiro compound in which two rings share a central element adopting a tetrahedral structure, such as C and Si; aromatic amine derivatives such as triarylamine; triphenylene derivatives; nitrogen-containing heterocycle derivatives; and liquid crystalline cyano derivatives.

The redox pair serves as an electron carrier, and thus it is required to have a certain concentration. The concentration is preferably 0.01 mol/L or more, more preferably 0.1 mol/L or more, and particularly preferably 0.3 mol/L or more, in total. The upper limit in this case is not particularly limited but is usually about 5 mol/L.

—Co-Adsorbent—

In the photoelectric conversion element of the present invention, a co-adsorbent is preferably used in combination with the metal complex dye of the present invention or another dye to be used if necessary. As such a co-adsorbent, a co-adsorbent having at least one acidic group (preferably a carboxyl group, or a potassium salt, a lithium salt or a cesium of a carboxyl group) is preferable, and examples of the co-adsorbent include a fatty acid and a compound having a steroid skeleton. The fatty acid may be a saturated fatty acid or an unsaturated fatty acid. Examples thereof include a butanoic acid, a hexanoic acid, an octanoic acid, a decanoic acid, a hexadecanoic acid, a dodecanoic acid, a palmitic acid, a stearic acid, an oleic acid, a linoleic acid, and a linolenic acid.

Examples of the compound having a steroid skeleton include a cholic acid, a glycocholic acid, a chenodeoxycholic acid, a hyocholic acid, a deoxycholic acid, a lithocholic acid, and ursodeoxycholic acid. Among these, a cholic acid, a deoxycholic acid, and a chenodeoxycholic acid are preferable; and a chenodeoxycholic acid is more preferable.

A preferred co-adsorbent is a compound represented by the following Formula (CA).

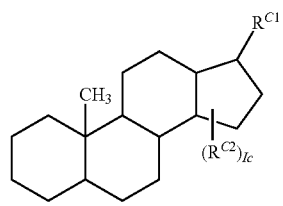

Formula (CA)

In the Formula (CA), $R^{C1}$ represents a substituent having an acidic group. $R^{C2}$ represents a substituent. Ic represents an integer of 0 or more.

The acidic group has the same meaning as described above, and the preferable range is also the same.

Of these, $R^{C1}$ is preferably an alkyl group substituted with any one of a carboxyl group, a sulfo group, and a salt thereof; and further preferably —CH(CH$_3$)CH$_2$CH$_2$CO$_2$H, or —CH(CH$_3$)CH$_2$CH$_2$CONHCH$_2$CH$_2$SO$_3$H.

Examples of $R^{C2}$ include those exemplified as the substituent T described later. Of these, an alkyl group, a hydroxyl group, an acyloxy group, an alkylaminocarbonyloxy group, and an arylaminocarbonyloxy group are preferable; and an alkyl group, a hydroxyl group, and an acyloxy group are more preferable.

Ic is preferably from 2 to 4.

Examples of the specific compounds include the compounds mentioned as the compound having a steroid skeleton.

By adsorbing on the semiconductor fine-particles, the co-adsorbent that can be used in the present invention exhibits an effect on suppressing the inefficient association of the dye, and preventing reverse electron transfer from the semiconductor fine-particle surface to the redox system in the electrolyte. An amount to be used of the co-adsorbent is not particularly limited, and it is preferred, from the viewpoint of exhibiting effectively the effects, that the amount is preferably from 1 to 200 moles, more preferably from 10 to 150 moles, and particularly preferably from 20 to 50 moles, with respect to 1 mole of the dyes.

<Substituent T>

The specification uses an expression "compound" (including complex and dye) to mean, in addition to the compound itself, its salts, its complex and its ion. Further, a substituent with which substitution or non-substitution is not explicitly described in the present specification (the same applies to a linking group and a ligand), means that the substituent may have an arbitrary substituent. The same is also true on a compound with which substitution or non-substitution is not explicitly described. Preferable examples of the substituent include the following substituent T.

In the present specification, the simple description only as a "substituent" means to refer to this substituent T. Further, in the case where each of the substituents, for example, like an alkyl group, is described in a simplistic form, both a preferable range and specific examples for the corresponding group of the substituent T are applied to.

The substituent T includes the following:

an alkyl group (preferably an alkyl group having 1 to 20 carbon atoms, e.g. methyl, ethyl, isopropyl, t-butyl, pentyl, heptyl, 1-ethylpentyl, benzyl, 2-ethoxyethyl, 1-carboxymethyl, or trifluoromethyl), an alkenyl group (preferably an alkenyl group having 2 to 20 carbon atoms, e.g. vinyl, allyl, or oleyl), an alkynyl group (preferably an alkynyl group having 2 to 20 carbon atoms, e.g. ethynyl, 2-propynyl, 2-butynyl, or phenylethynyl), a cycloalkyl group (preferably a cycloalkyl group having 3 to 20 carbon atoms, e.g. cyclopropyl, cyclopentyl, cyclohexyl, or 4-methylcyclohexyl), an cycloalkenyl group (preferably a cycloalkenyl group having 5 to 20 carbon atoms, e.g. cyclopentenyl, or cyclohexenyl), an aryl group (preferably an aryl group having 6 to 26 carbon atoms, e.g. phenyl, 1-naphthyl, 4-methoxyphenyl, 2-chlorophenyl, or 3-methylphenyl), a heterocyclic group (preferably a 5- or 6-membered heterocyclic group having 2 to 20 carbon atoms and at least one oxygen atom, sulfur atom, or nitrogen atom, e.g. 2-pyridyl, 4-pyridyl, 2-imidazolyl, 2-benzimidazolyl, 2-thiazolyl, or 2-oxazolyl), an alkoxy group (preferably an alkoxy group having 1 to 20 carbon atoms, e.g. methoxy, ethoxy, isopropyloxy, or benzyloxy), an alkenyloxy group (preferably an alkenyloxy group having 2 to 20 carbon atoms, e.g. vinyloxy or allyloxy), an alkynyloxy group (preferably an alkynyloxy group having 2 to 20 carbon atoms, e.g. 2-propynyloxy or 4-butynyloxy), a cycloalkyloxy group (preferably an cycloalkyloxy group having 3 to 20 carbon atoms, e.g. cyclopropyloxy, cyclopentyloxy, cyclohexyloxy, or 4-methylcyclohexyloxy), an aryloxy group (preferably an aryloxy group having 6 to 26 carbon atoms, e.g. phenoxy, 1-naphthyloxy, 3-methylphenoxy, or 4-methoxyphenoxy), a heterocyclic oxy group (e.g. imidazolyloxy, benzoimidazolyloxy, thiazolyloxy, benzothiazolyloxy, triazinyloxy, or purinyloxy);

an alkoxycarbonyl group (preferably an alkoxycarbonyl group having 2 to 20 carbon atoms, e.g. ethoxycarbonyl, or 2-ethylhexyloxycarbonyl), a cycloalkoxycarbonyl group (preferably a cycloalkoxycarbonyl group having 4 to 20 carbon atoms, e.g. cyclopropyloxycarbonyl, cyclopentyloxycarbonyl, cyclohexyloxycarbonyl), an aryloxycarbonyl group (preferably an aryloxycarbonyl group having 6 to 20 carbon atoms, e.g. phenyloxycarbonyl, or naphthyloxycarbonyl), an amino group (preferably an amino group having 0 to 20 carbon atoms including an alkylamino group, an alkenylamino group, an alkynylamino group, a cycloalkylamino group, a cycloalkenylamino group, an arylamino group, and a heterocyclic amino group, e.g. amino, N,N-dimethylamino, N,N-diethylamino, N-ethylamino, N-allylamino, N-(2-propinyl)amino, N-cyclohexylamino, N-cyclohexenylamino, anilino, pyridylamino, imidazolylamino, benzimidazolylamino, thiazolylamino, benzothiazolylamino, or triazinylamino), a sulfamoyl group (preferably a sulfamoyl group having 0 to 20 carbon atoms, preferably an alkyl-, cycloalkyl- or aryl-sulfamoyl group, e.g. N,N-dimethylsulfamoyl, N-cyclohexylsulfamoyl or N-phenylsulfamoyl), an acyl group (preferably an acyl group having 1 to 20 carbon atoms, e.g. acetyl, cyclohexylcarbonyl or benzoyl), an acyloxy group (preferably an acyloxy group having 1 to 20 carbon atoms, e.g. acetyloxy, cyclohexylcarbonyloxy, or benzoyloxy), a carbamoyl group (preferably a carbamoyl group having 1 to 20 carbon atoms, preferably an alkyl-, cycloalkyl- or aryl-carbamoyl group, e.g. N,N-dimethylcarbamoyl, N-cyclohexylcarbamoyl, or N-phenylcarbamoyl), an acylamino group (preferably an acylamino group having 1 to 20 carbon atoms, e.g. acetylamino, cyclohexylcarbonylamino or benzoylamino), a sulfonamide group (preferably a sulfonamide group having 0 to 20 carbon atoms, preferably an alkyl-, cycloalkyl- or aryl-sulfonamide group, e.g. methane sulfonamide, benzene sulfonamide, N-methyl methane sulfonamide, N-cyclohexyl sulfonamide or N-ethyl benzene sulfonamide), an alkylthio group (preferably an alkylthio group having 1 to 20 carbon atoms, e.g. methylthio, ethylthio, isopropylthio, or benzylthio), a cycloalkylthio group (preferably a cycloalkylthio group having 3 to 20 carbon atoms, e.g. cyclopropylthio, cyclopentylthio, cyclohexylthio, 4-methyl cyclohexylthio), an arylthio group (preferably an arylthio group having 6 to 26 carbon atoms, e.g. phenylthio, 1-naphthylthio, 3-methylphenylthio, or 4-methoxyphenylthio), an alkyl-, cycloalkyl- or aryl-sulfonyl group (preferably a sulfonyl group having 1 to 20 carbon atoms, e.g. methylsulfonyl, ethylsulfonyl, cyclohexyl sulfonyl or benzene sulfonyl), a silyl group (preferably a silyl group having 1 to 20 carbon atoms, preferably an alkyl-, aryl-, alkoxy-, or aryloxy-substituted silyl group, e.g. triethylsilyl, triphenylsilyl, diethylbenzylsilyl, or dimethylphenylsilyl), a silyloxy group (preferably a silyloxy group having 1 to 20 carbon atoms, preferably an alkyl-, aryl-, alkoxy-, or aryloxy-substituted silyloxy group, e.g. triethylsilyloxy, triphenylsilyloxy, diethylbenzylsilyloxy, or dimethylphenylsilyloxy), a hydroxyl group, a cyano group, a nitro group, a halogen atom (e.g. fluorine atom, chlorine atom, bromine atom, or iodine atom), a carboxyl group, a sulfo group, a phosphonyl group, a phosphoryl group, and a boric-acid group; more preferably an alkyl group, an alkenyl group, a cycloalkyl group, an aryl group, a heterocyclic group, an alkoxy group, a cycloalkoxy group, an aryloxy group, an alkoxycarbonyl group, an cycloalkoxycarbonyl group, the above-mentioned amino group, an acylamino group, a cyano group, or a halogen atom; and particularly preferably an alkyl group, an alkenyl group, a heterocyclic group, an alkoxy group, an alkoxycarbonyl group, an amino group, an acylamino group, or a cyano group.

When the compound or the substituent or the like contains an alkyl group, an alkenyl group, or the like, these may be a straight chain or a branched chain, and these may be substituted or unsubstituted. Further, in the case of containing an aryl group, a heterocyclic group or the like, these may be a single ring or a fused ring, and may be substituted or unsubstituted.

<Counter Electrode (Opposite Electrode)>

The counter electrode is preferably an electrode working as a positive electrode in the dye-sensitized solar cell (photoelectrochemical cell). The counter electrode usually has the same meaning as the electrically-conductive support described above, but in a construction which is likely to maintain a sufficient strength, a support is not necessarily required. A preferred structure of the counter electrode is a structure having a high charge collecting effect. At least one of the electrically-conductive support and the counter electrode as mentioned above should be substantially transparent, in order for light to reach the photoconductor layer. In the dye-sensitized solar cell of the present invention, the electrically-conductive support is preferably transparent to allow sunlight to inject from the support side. In this case, the counter electrode further preferably has properties of reflecting light. As the counter electrode of the dye-sensitized solar cell, a glass or plastic plate on which a metal or an electrically-conductive oxide is deposited is preferable, and a glass plate on which platinum is deposited is particularly preferable. In the dye-sensitized solar cell, a lateral side of the cell is preferably sealed with a polymer, an adhesive, or the like, in order to prevent evaporation of the component.

The present invention can be applied to the photoelectric conversion elements and the dye-sensitized solar cells described, for example, in Japanese Patent No. 4260494, JP-A-2004-146425, JP-A-2000-340269, JP-A-2002-289274, JP-A-2004-152613, JP-A-9-27352. In addition, the present invention can be applied to the photoelectric conversion elements and the dye-sensitized solar cells described, for example, in JP-A-2004-152613, JP-A-2000-90989, JP-A-2003-217688, JP-A-2002-367686, JP-A-2003-323818, JP-A-2001-43907, JP-A-2000-340269, JP-A-2005-85500, JP-A-2004-273272, JP-A-2000-323190, JP-A-2000-228234, JP-A-2001-266963, JP-A-2001-185244, JP-T-2001-525108, JP-A-2001-203377, JP-A-2000-100483, JP-A-2001-210390, JP-A-2002-280587, JP-A-2001-273937, JP-A-2000-285977, JP-A-2001-320068.

<<Dye Solution, Dye-Adsorbed Electrode Using the Same, and Production Method of Dye-Sensitized Solar Cell>>

In the present invention, a dye-adsorbed electrode is preferably produced using a dye solution containing the metal complex dye of the present invention.

The foregoing dye solution contains the metal complex dye of the present invention dissolved in a solvent, and may comprise a co-adsorbent and other ingredients as needed.

Examples of the solvent to be used include solvents described in JP-A-2001-291534, but the solvent is not particularly limited thereto. In the present invention, organic solvents are preferred. More preferred are alcohols, amides, nitriles, hydrocarbons, and a mixed solvent of two or more kinds of these solvents. As the mixed solvent, preferred are mixed solvents of alcohols and a solvent selected from amides, nitriles, and hydrocarbons. More preferred are mixed solvents of alcohols and amides and mixed solvents of alcohols and hydrocarbons, and particularly preferred are mixed solvents of alcohols and amides. Specifically, methanol, ethanol, propanol, butanol, dimethylformamide, and dimethylacetamide are preferred.

The dye solution preferably contains a co-adsorbent, and the co-adsorbent is preferably the aforementioned ones. Among them, the compound represented by Formula (CA) is preferred.

The dye solution of the present invention is preferably one in which the concentrations of the metal complex dye and the co-adsorbent have been adjusted so that the dye solution can be used as it is at the time of preparation of a photoelectric conversion element or a dye-sensitized solar cell. In the present invention, the metal complex dye of the present invention is preferably contained in an amount of from 0.001 to 0.1% by mass.

In the dye solution, it is particularly preferable to adjust the water content, and thus in the present invention, it is preferred that the content (content rate) of water is adjusted to the range of from 0 to 0.1% by mass.

Similarly, it is also preferable to adjust the water content in the electrolyte in a photoelectric conversion element and a dye-sensitized solar cell, in order to achieve the effects of the present invention effectively. Thus, it is preferred that the content (content rate) of water in the electrolyte solution is adjusted to the range of from 0 to 0.1% by mass. The foregoing adjustment of the electrolyte is particularly preferably carried out with the dye solution.

In the present invention, a dye-adsorbed electrode is preferably a semiconductor electrode for dye-sensitized solar cell, which is prepared by allowing the surface of the semiconductor fine particles provided on the semiconductor electrode, to carry the metal complex dye, with using the above dye solution.

In other words, the dye-adsorbed electrode for dye-sensitized solar cell preferably has a photoconductor layer which is obtained by coating a composition obtained from the aforementioned dye solution, on an electrically-conductive support provided with semiconductor fine particles, and curing the composition after coating.

In the present invention, it is preferable that a dye-sensitized solar cell be produced by using the dye-adsorbed electrode for dye-sensitized solar cell, preparing an electrolyte and a counter electrode, and performing an assembly with using them.

EXAMPLES

The present invention will be described in more detail based on examples given below, but the invention is not meant to be limited by these.

Example 1

<Synthesis of Metal Complex Dye>

Hereinafter, the synthetic method of the metal complex dye of the present invention will be described in detail, but starting substances, dye intermediates and synthetic routes are not limited to these.

(Synthesis of Exemplified Dye D-1-1a)

Exemplified dye D-1-1a was synthesized according to the following reaction scheme.

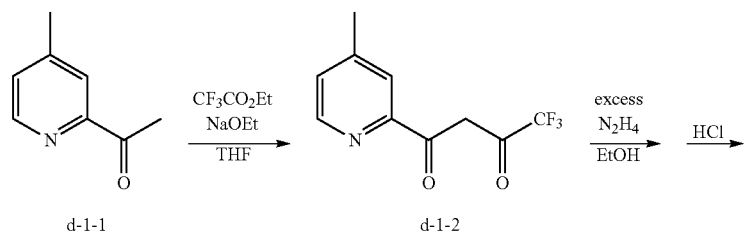

-continued
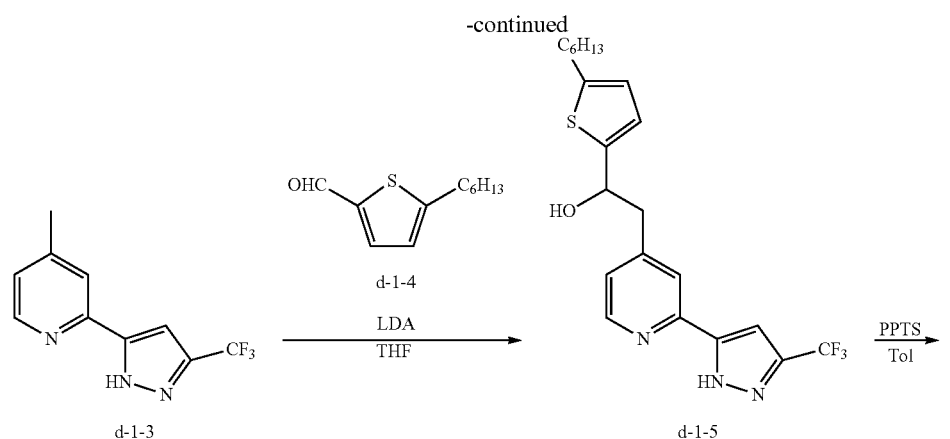
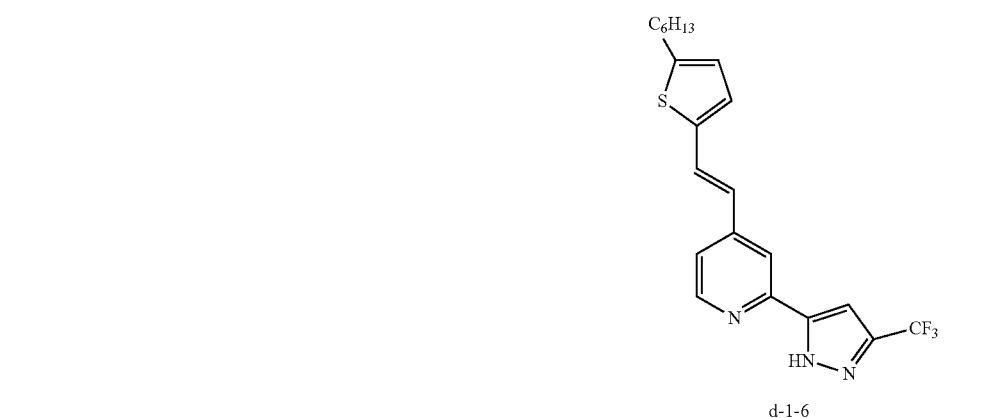
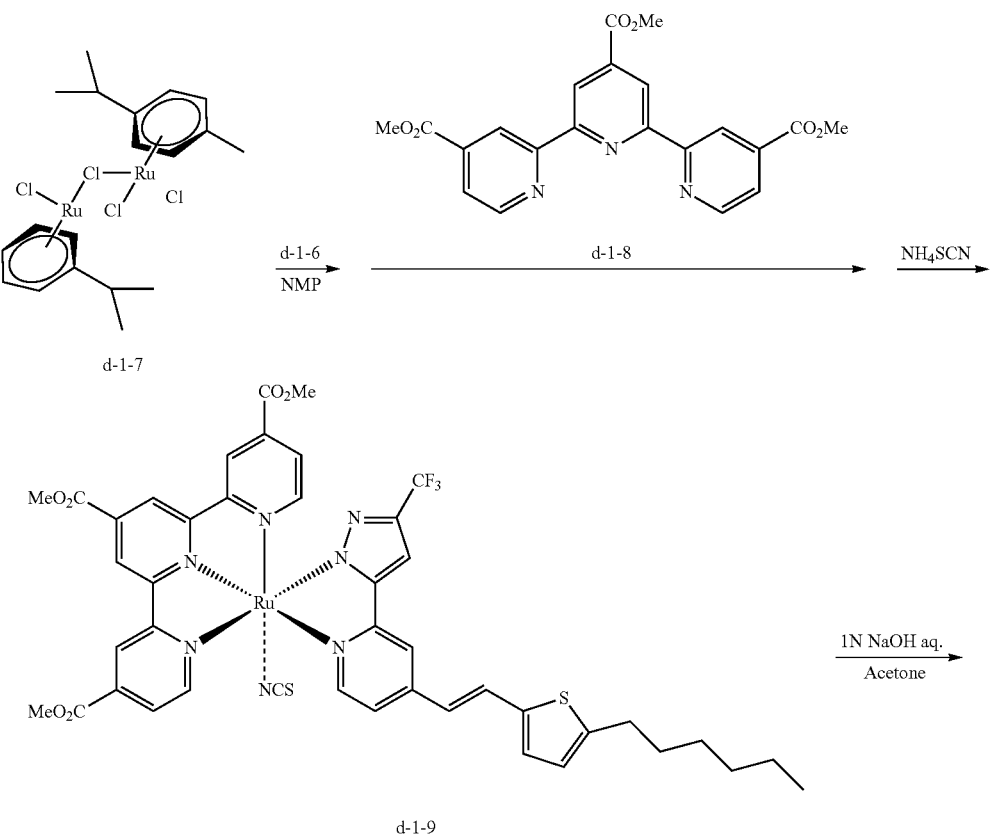

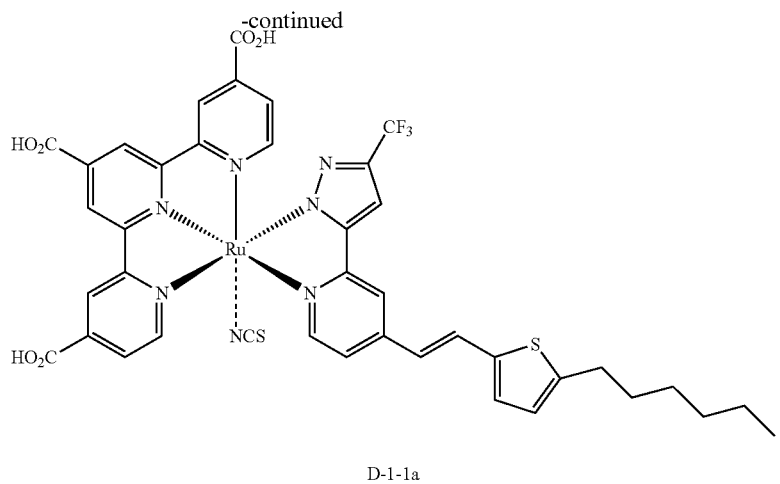

D-1-1a (i) Synthesis of Compound d-1-2

In 200 mL of THF (tetrahydrofuran), 25 g of compound d-1-1 (2-acetyl-4-methylpyridine) was dissolved, and 18.9 g of sodium ethoxide was added thereto, while stirring at 0° C., under a nitrogen atmosphere, followed by stirring for 15 minutes. Then, 28.9 g of ethyl trifluoroacetate was added dropwise thereto, followed by stirring for 20 hours at external temperature of 70° C. After bringing the temperature to room temperature, an ammonium chloride aqueous solution was added dropwise thereto, followed by separation of the liquid, and concentration of the thus-separated organic layer. Thus, 72.6 g of the crude product d-1-2 was obtained.

(ii) Synthesis of Compound d-1-3

In 220 mL of ethanol, 72.6 g of compound d-1-2 was dissolved, and 5.6 mL of hydrazine monohydrate was added thereto, while stirring at room temperature, under a nitrogen atmosphere, followed by heating for 12 hours at external temperature of 90° C. After that, 5 mL of concentrated hydrochloric acid was added thereto, followed by stirring for 1 hour. After concentration, extraction and separation was conducted with 150 mL of sodium bicarbonate water and 150 mL of ethyl acetate, and then the thus-obtained organic layer was concentrated. After recrystallization from acetonitrile, 31.5 g of compound d-1-3 was obtained.

(iii) Synthesis of Compound d-1-5

While stirring 4.1 g of diisopropylamine and 30 mL of tetrahydrofurane at −40° C. under a nitrogen atmosphere, 23.1 mL of a 1.6 M n-butyl lithium hexane solution was added dropwise thereto, followed by stirring for 2 hours. After that, 4.0 g of compound d-1-3 was added thereto, followed by stirring at 0° C. for 80 minutes. Then, a solution containing 3.45 g of the compound d-1-4 dissolved in 15 mL of tetrahydrofurane was added dropwise thereto. After that, the resultant mixture was stirred at 0° C. for 80 minutes, and then stirred at room temperature for 5 hours. Then, an ammonium chloride solution was added thereto, followed by extraction and separation with ethyl acetate. Then, the thus-obtained organic layer was concentrated. After purification using a silica gel column chromatography, 5.7 g of the compound d-1-5 was obtained.

(iv) Synthesis of Compound d-1-6

To 50 mL of toluene, 5.0 g of the compound d-1-5 and 5.9 g of PPTS (pyridinium para-toluenesulfonate) were added, and the resultant mixture was heated under reflux for 5 hours under a nitrogen atmosphere. After concentration, the resultant liquid was separated with a saturated aqueous solution of sodium bicarbonate and methylene chloride, and the resultant organic layer was concentrated. The crystal obtained was recrystallized from methanol and methylene chloride, to give 4.3 g of compound d-1-6.

The structure of compound d-1-6 obtained was confirmed by MS (mass spectrum) measurement.

MS-ESI m/z=404.2 (M-H)$^+$ (v) Synthesis of Exemplified Dye D-1-1a

To 150 mL of NMP (N-methylpyrrolidone), 1.22 g of compound d-1-7 and 1.62 g of compound d-1-6 were added, followed by stirring at 70° C. for 3 hours under a nitrogen atmosphere. Then, 1.63 g of compound d-1-8 was added thereto, followed by stirring under heating at 160° C. for 8 hours. Then, 10.7 g of ammonium thiocyanate was added thereto, followed by stirring at 160° C. for 8 hours. After concentration, water was added, followed by filtration. The filtrate was purified by a silica gel column chromatography to obtain compound d-1-9, followed by adding the obtained compound to a mixed solvent of 30 mL of acetone and 40 mL of a 1N sodium hydroxide aqueous solution, and stirring for 24 hours at external temperature of 65° C. After bringing the temperature to room temperature, the pH was adjusted to 1.5 with hydrochloric acid, and the precipitate was filtrated, to give 3.3 g of crude product D-1-1a.

This was dissolved in a methanol solution together with TBAOH (tetrabutylammonium hydroxide), and purified by SephadexLH-20 column. The fraction of the main layer was collected and concentrated, and then a solution of 0.1M trifluoromethanesulfonic acid was added thereto so as to adjust the pH thereof to 3, and the precipitate was filtered, thereby obtaining 2.4 g of exemplified dye D-1-1a.

The structure of exemplified dye D-1-1a obtained was confirmed by MS measurement.

MS-ESI m/z=928.1 (M-H)$^+$ (Synthesis of Exemplified Dye D-1-5a)

Compound d-2-2 was synthesized according to the following reaction scheme. Then, exemplified dye D-1-5a was synthesized in the same manner as exemplified dye D-1-1a, except that compound d-1-4 for exemplified dye D-1-1a was changed to compound d-2-2.

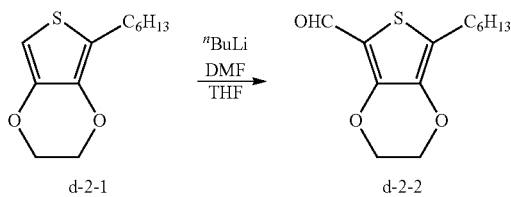

(Synthesis of Exemplified Dye D-1-6a)

Compound d-3-3 was synthesized according to the following reaction scheme. Then, exemplified dye D-1-6a was synthesized in the same manner as exemplified dye D-1-1a, except that compound d-1-4 for exemplified dye D-1-1a was changed to compound d-3-3.

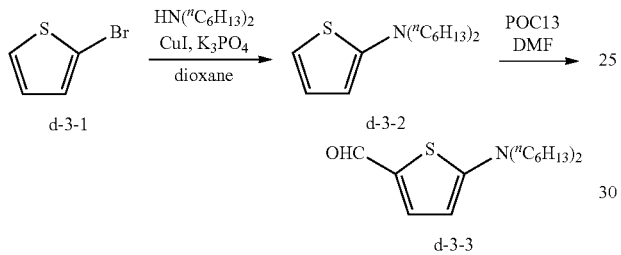

(Synthesis of Exemplified Dye D-1-8a)

Compound d-4-2 was synthesized according to the following reaction scheme. Then, exemplified dye D-1-8a was synthesized in the same manner as exemplified dye D-1-1a, except that compound d-1-4 for exemplified dye D-1-1a was changed to compound d-4-2.

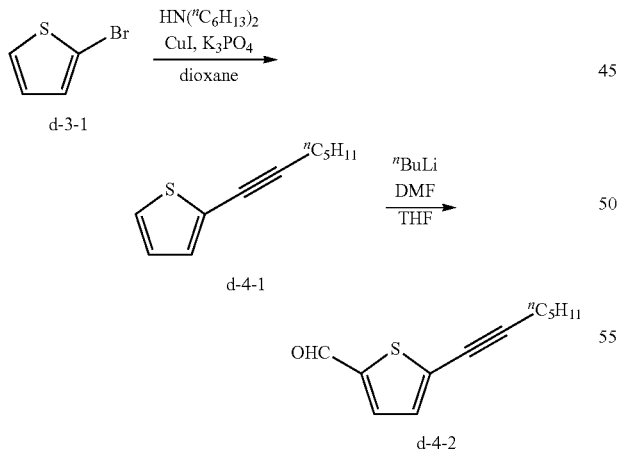

(Synthesis of Exemplified Dye D-1-9a)

Compound d-5-8 was synthesized according to the following reaction scheme. Then, exemplified dye D-1-9a was synthesized in the same manner as exemplified dye D-1-1a, except that compound d-1-6 for exemplified dye D-1-1a was changed to compound d-5-8.

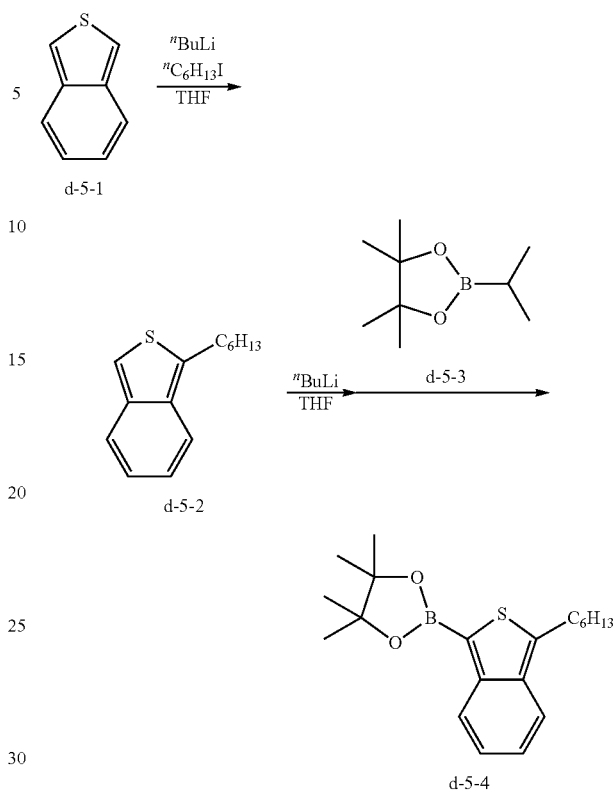

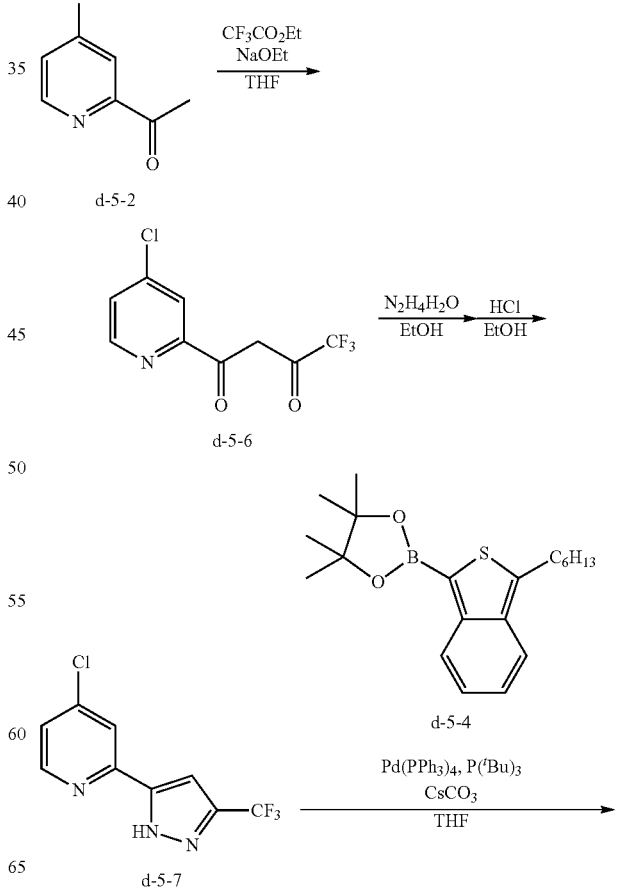

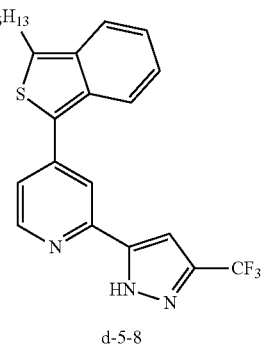

d-5-8

(Synthesis of Exemplified Dye D-1-14a)

Exemplified dye D-1-14a was synthesized in the same manner as exemplified dye D-1-9a, except that compound d-5-1 for exemplified dye D-1-9a was changed to compound d-6-1.

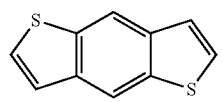

d-6-1

(Synthesis of Exemplified Dye D-1-13a)

Exemplified dye D-1-13a was synthesized in the same manner as exemplified dye D-1-9a, except that compound d-5-1 for exemplified dye D-1-9a was changed to compound d-7-1.

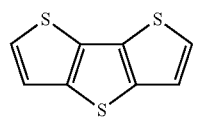

d-7-1

(Synthesis of Exemplified Dye D-1-12a)

Exemplified dye D-1-12a was synthesized in the same manner as exemplified dye D-1-9a, except that compound d-5-1 for exemplified dye D-1-9a was changed to compound d-7-2.

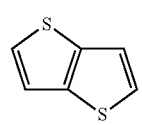

d-7-2

(Synthesis of Exemplified Dye D-1-2a)

Compound d-8-2 was synthesized according to the following reaction scheme. Then, exemplified dye D-1-2a was synthesized in the same manner as exemplified dye D-1-1a, except that compound d-1-4 for exemplified dye D-1-1a was changed to compound d-8-2.

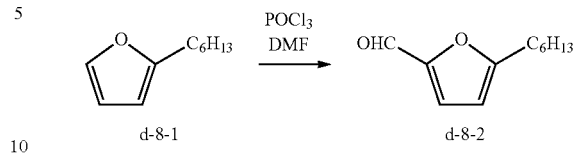

(Synthesis of Exemplified Dye D-1-23a)

Exemplified dye D-1-23a was synthesized in the same manner as exemplified dye D-1-1a, except that ethyl trifluoroacetate for exemplified dye D-1-1a was changed to compound d-9-1.

d-9-1

(Synthesis of Exemplified Dye D-1-27a)

Exemplified dye D-1-27a was synthesized in the same manner as exemplified dye D-1-1a, except that ethyl trifluoroacetate for exemplified dye D-1-1a was changed to compound d-10-1.

d-10-1

(Synthesis of Exemplified Dye D-1-7a)

Compound d-11-1 was synthesized according to the following reaction scheme. Then, exemplified dye D-1-7a was synthesized in the same manner as exemplified dye D-1-9a, except that compound d-5-4 was changed to compound d-11-1.

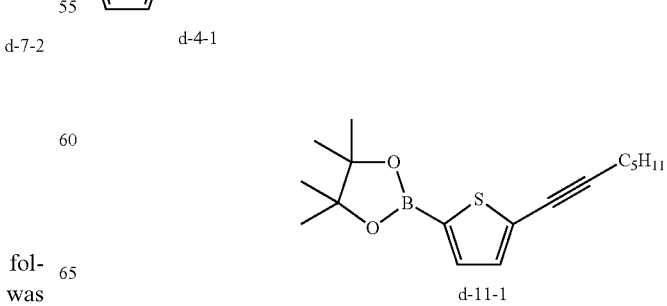

(Synthesis of Exemplified Dye D-1-16a)

Exemplified dye D-1-16a was synthesized in the same manner as exemplified dye D-1-1a, except that compound d-1-1 for exemplified dye D-1-1a was changed to compound d-14-1.

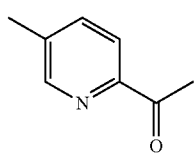

d-14-1

(Synthesis of Exemplified Dye D-1-26a)

Compound d-13-3 was synthesized according to the following reaction scheme. Then, exemplified dye D-1-26a was synthesized in the same manner as exemplified dye D-1-1a, except that compound d-1-3 was changed to compound d-13-3.

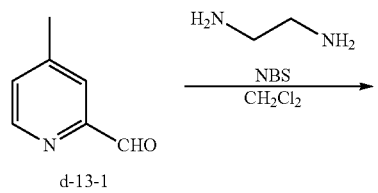

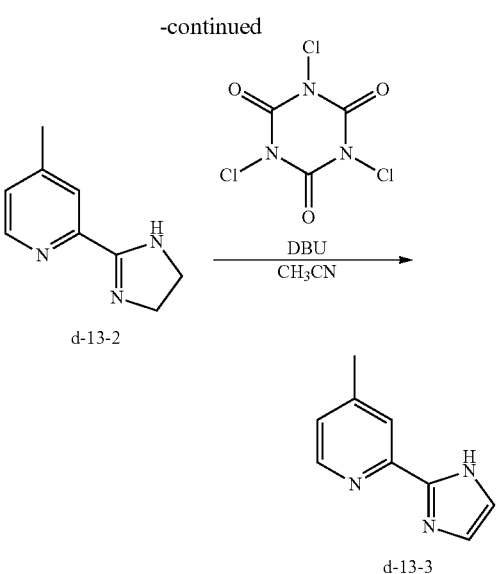

(Synthesis of Exemplified Dye D-1-18a)

Exemplified dye D-1-18a was synthesized in the same manner as exemplified dye D-1-1a, except that compound d-1-1 was changed to compound d-20-1.

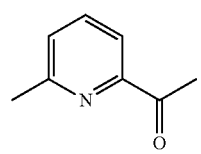

d-20-1

(Synthesis of Exemplified Dye D-3-1a)

Exemplified dye D-3-1a was synthesized in the same manner as exemplified dye D-1-1a, according to the method shown in the following scheme, except that compound d-1-7 for exemplified dye D-1-1a was changed to compound d-15-1.

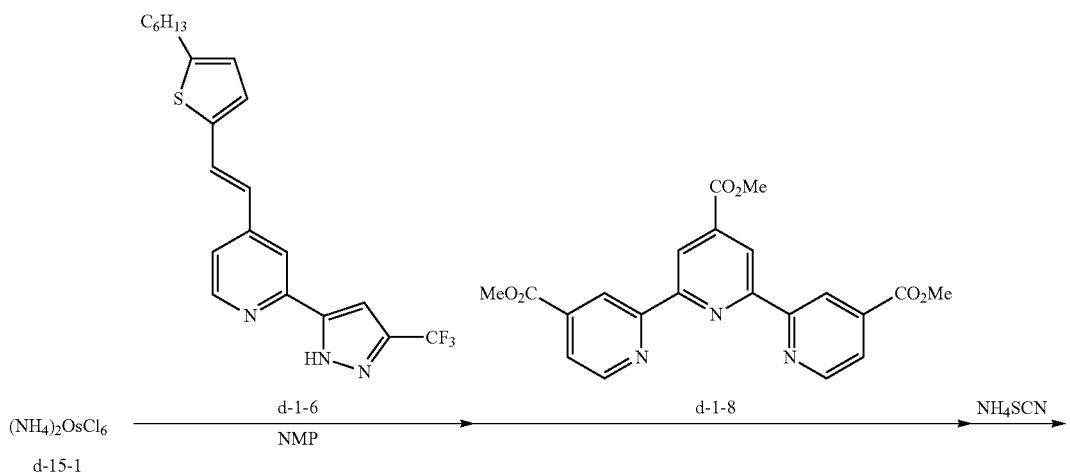

-continued

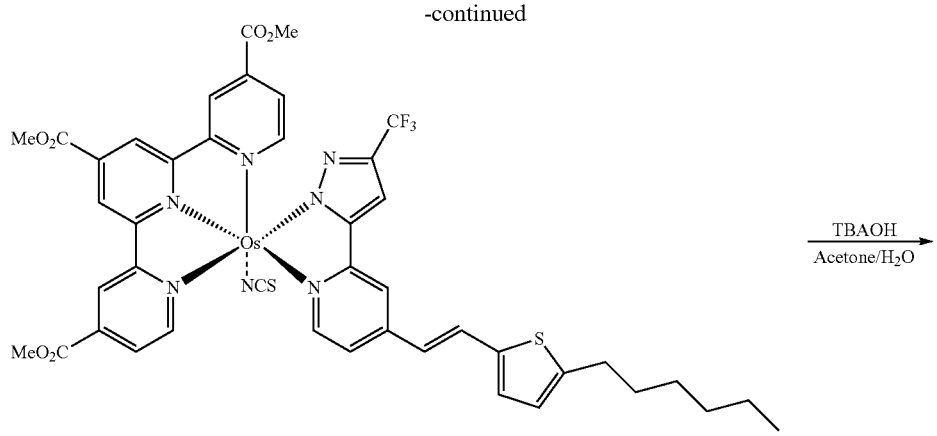

d-15-2

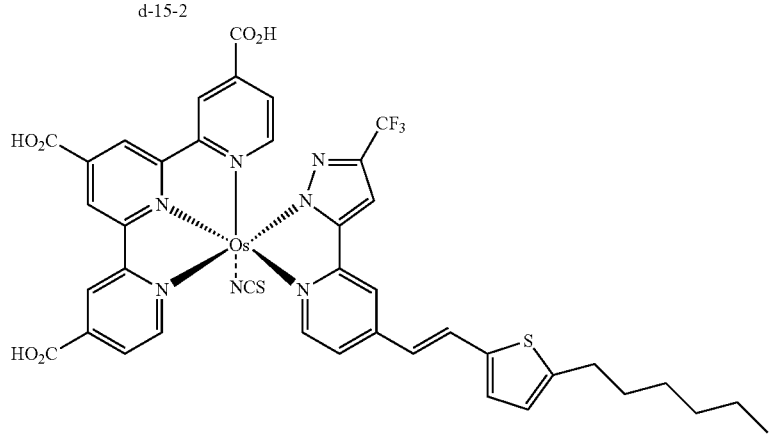

D-3-1a (Synthesis of Exemplified Dye D-1-35a)

Compound d-16-2 was synthesized according to the following reaction scheme. Then, exemplified dye D-1-35a was synthesized in the same manner as exemplified dye D-1-1a, except that compound d-1-3 was changed to compound d-16-2.

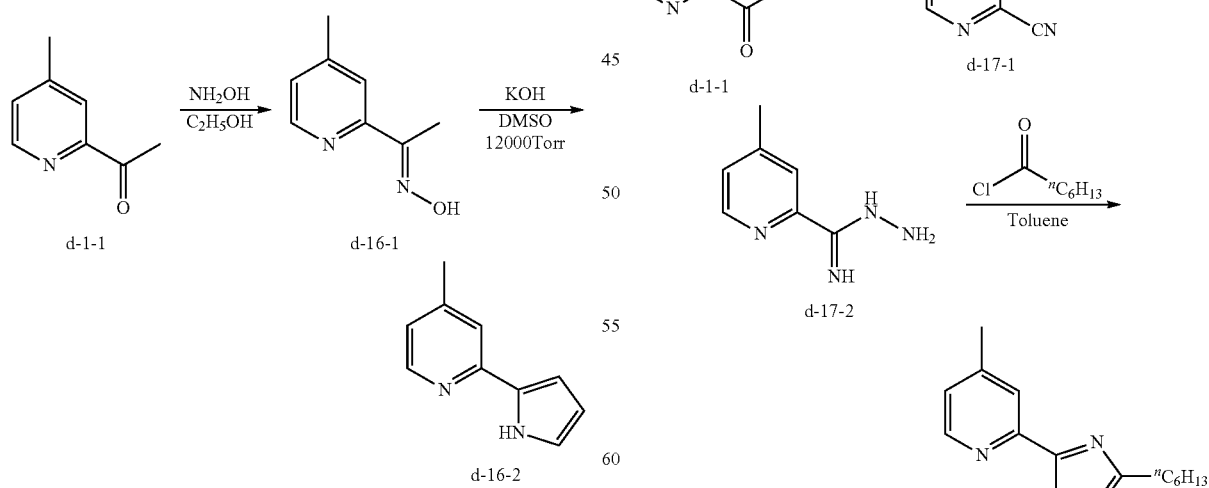

(Synthesis of Exemplified Dye D-1-36a)

Compound d-17-3 was synthesized according to the following reaction scheme. Then, exemplified dye D-1-36a was synthesized in the same manner as exemplified dye D-1-1a, except that compound d-1-3 was changed to compound d-17-3.

(Synthesis of Exemplified Dye D-1-37a)

Compound d-18-1 was synthesized according to the following reaction scheme. Then, exemplified dye D-1-37a was synthesized in the same manner as exemplified dye D-1-1a, except that compound d-1-3 was changed to compound d-18-1.

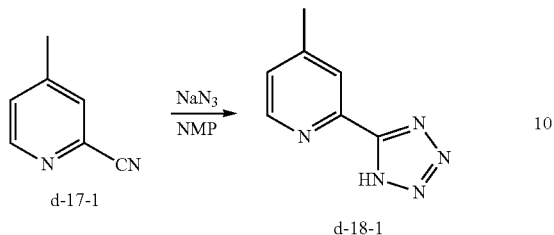

(Synthesis of Exemplified Dye D-3-5a)

Exemplified dye D-3-5a was synthesized in the same manner as exemplified dye D-1-1a, except that ammonium thiocyanate was changed to compound d-19-1.

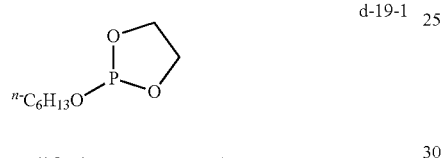

(Synthesis of Exemplified Dye D-1-15a)

Exemplified dye D-1-15a was synthesized in the same manner as exemplified dye D-1-9a, except that compound d-5-1 for exemplified dye D-1-9a was changed to compound d-24-1.

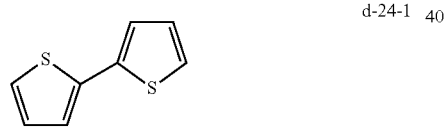

(Synthesis of Exemplified Dye D-1-38a)

Exemplified dye D-1-38a was synthesized in the same manner as exemplified dye D-1-9a, except that compound d-5-4 for exemplified dye D-1-9a was changed to compound d-25-1.

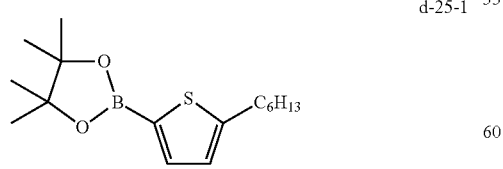

(Synthesis of Exemplified Dye D-1-46a)

Exemplified dye D-1-46a was synthesized in the same manner as exemplified dye D-1-1a, except that compound d-1-4 for exemplified dye D-1-1a was changed to compound d-26-1. Herein, compound d-26-1 was synthesized by the method described in Monatsberichte der Deutschen Akademie der Wissenschaften zu Berlin, 1959, vol. 1, p. 180.

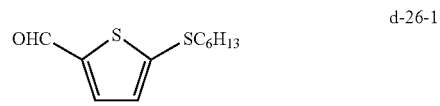

(Synthesis of Exemplified Dye D-1-45a)

Exemplified dye D-1-45a was synthesized in the same manner as exemplified dye D-1-9a, except that compound d-5-4 for exemplified dye D-1-9a was changed to compound d-27-1.

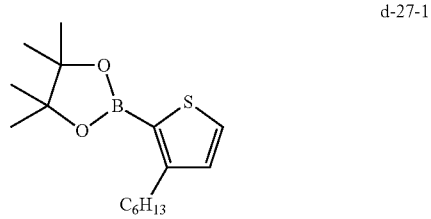

(Synthesis of Exemplified Dye D-1-32a)

Exemplified dye D-1-32a was synthesized in the same manner as exemplified dye D-1-1a, except that ammonium thiocyanate was changed to potassium iodide.

(Synthesis of Exemplified Dye D-2-10a)

Exemplified dye D-2-10a was synthesized in the same manner as exemplified dye D-1-1a, except that compound d-1-8 was changed to compound d-28-2. Herein, compound d-28-1 was synthesized by the method described in Solar Energy Materials & Solar Cells, 95, 2011, p. 310-314.

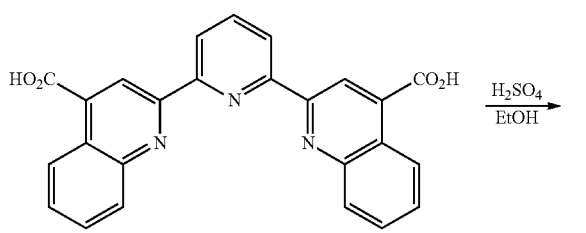

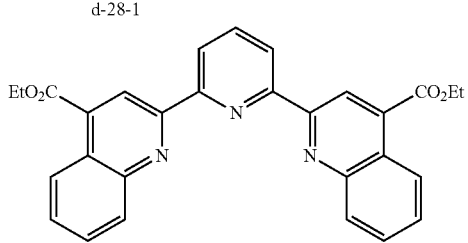

(Synthesis of Exemplified Dye D-1-53a)

Exemplified dye D-1-53a was synthesized in the same manner as exemplified dye D-1-1a, except that compound d-1-6 for exemplified dye D-1-1a was changed to compound d-32-1.

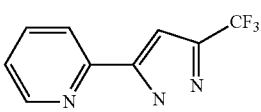

d-32-1

(Synthesis of Exemplified Dye D-2-8a)

Exemplified dye D-2-8a was synthesized in the same manner as exemplified dye D-1-1a, except that compound d-1-8 for exemplified dye D-1-1a was changed to compound d-37-4.

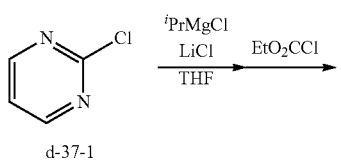

d-37-1

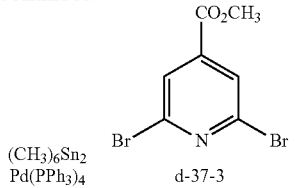

d-37-2

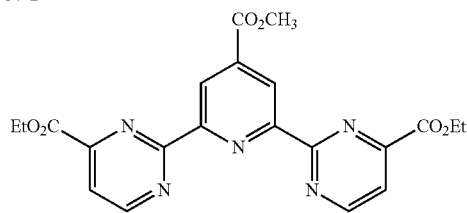

d-37-4

(Synthesis of Exemplified Dye D-2-9a)

Exemplified dye D-2-9a was synthesized in the same manner as exemplified dye D-1-1a, except that compound d-1-8 for exemplified dye D-1-1a was changed to compound d-39-1.

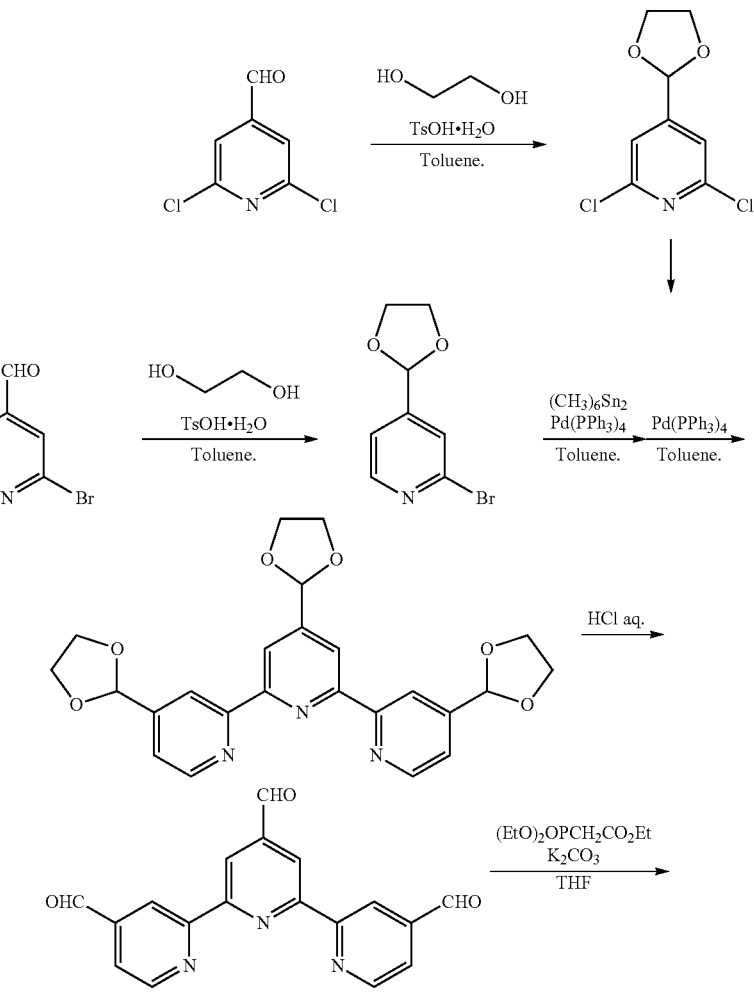

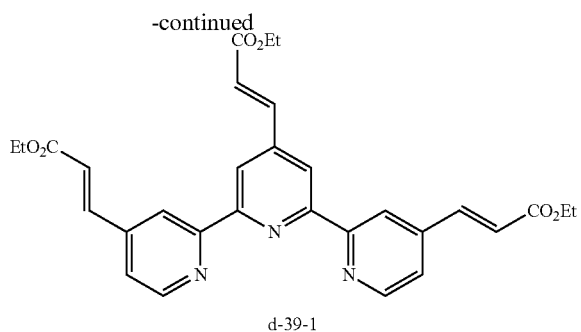

d-39-1

(Synthesis of Exemplified Dye D-1-54a)

Exemplified dye D-1-54a was synthesized in the same manner as exemplified dye D-1-1a, except that compound d-1-4 for exemplified dye D-1-1a was changed to compound d-40-1.

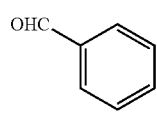

d-40-1

In the same manner as shown above, the remaining metal complex dyes below were synthesized.

The MS measurement results of the metal complex dyes are presented in the following Table 1.

TABLE 1

| Metal complex dye | MS-ESI |
|---|---|
| D-1-1a | MS-ESI m/z = 930.1(M + H)$^+$ |
| D-1-2a | MS-ESI m/z = 914.1(M + H)$^+$ |
| D-1-5a | MS-ESI m/z = 988.1(M + H)$^+$ |
| D-1-6a | MS-ESI m/z = 1029.2(M + H)$^+$ |
| D-1-7a | MS-ESI m/z = 934.1(M + H)$^+$ |
| D-1-8a | MS-ESI m/z = 940.1(M + H)$^+$ |
| D-1-9a | MS-ESI m/z = 954.1(M + H)$^+$ |
| D-1-12a | MS-ESI m/z = 960.0(M + H)$^+$ |
| D-1-13a | MS-ESI m/z = 1016.0(M + H)$^+$ |
| D-1-14a | MS-ESI m/z = 1010.1(M + H)$^+$ |
| D-1-15a | MS-ESI m/z = 986.1(M + H)$^+$ |
| D-1-16a | MS-ESI m/z = 930.1(M + H)$^+$ |
| D-1-18a | MS-ESI m/z = 930.1(M + H)$^+$ |
| D-1-23a | MS-ESI m/z = 1028.2(M + H)$^+$ |
| D-1-26a | MS-ESI m/z = 862.1(M + H)$^+$ |
| D-1-27a | MS-ESI m/z = 956.1(M + H)$^+$ |
| D-1-32a | MS-ESI m/z = 999.0(M + H)$^+$ |
| D-1-35a | MS-ESI m/z = 861.1(M + H)$^+$ |
| D-1-36a | MS-ESI m/z = 947.2(M + H)$^+$ |
| D-1-37a | MS-ESI m/z = 864.1(M + H)$^+$ |
| D-1-38a | MS-ESI m/z = 904.1(M + H)$^+$ |
| D-1-45a | MS-ESI m/z = 904.1(M + H)$^+$ |
| D-1-46a | MS-ESI m/z = 962.1(M + H)$^+$ |
| D-1-53a | MS-ESI m/z = 738.0(M + H)$^+$ |
| D-1-54a | MS-ESI m/z = 840.0(M + H)$^+$ |
| D-2-8a | MS-ESI m/z = 906.1(M + H)$^+$ |
| D-2-9a | MS-ESI m/z = 982.1(M + H)$^+$ |
| D-2-10a | MS-ESI m/z = 986.1(M + H)$^+$ |
| D-3-1a | MS-ESI m/z = 1019.1(M + H)$^+$ |
| D-3-5a | MS-ESI m/z = 1064.2(M + H)$^+$ |

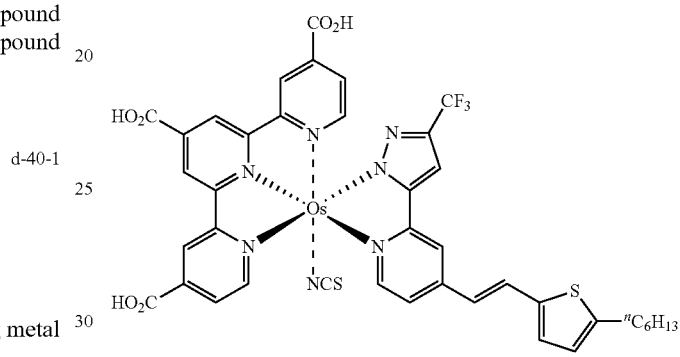

D-3-1a

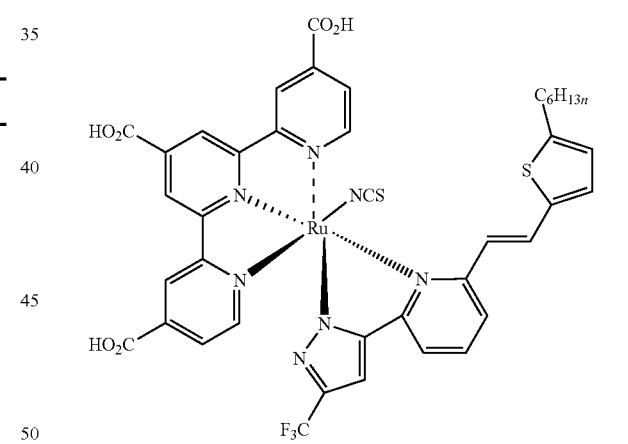

D-1-18a

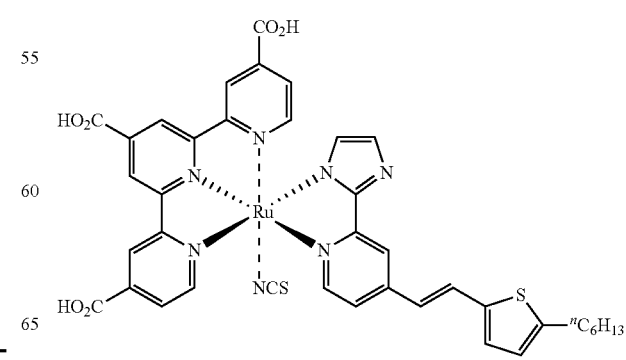

D-1-26a

D-1-16a
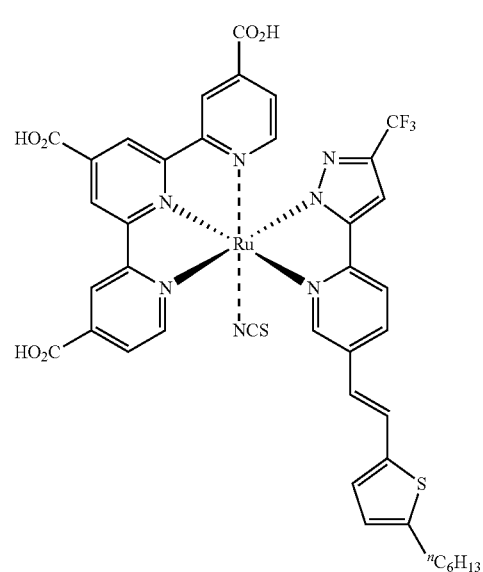
D-1-8a
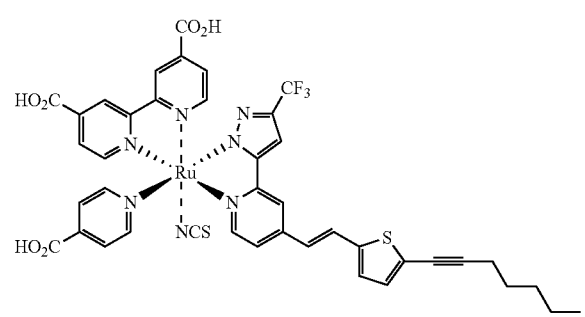
D-1-9a
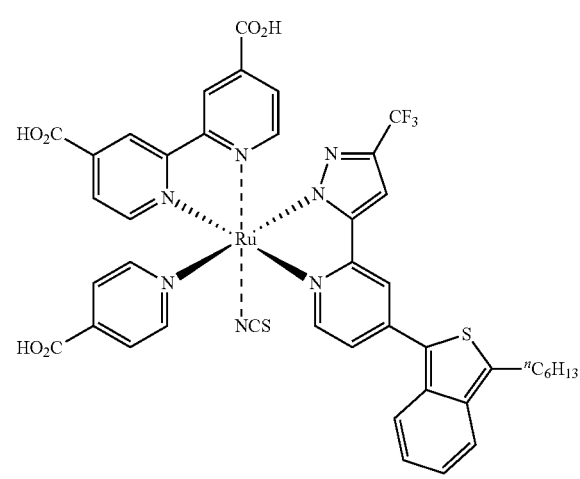
D-1-14a
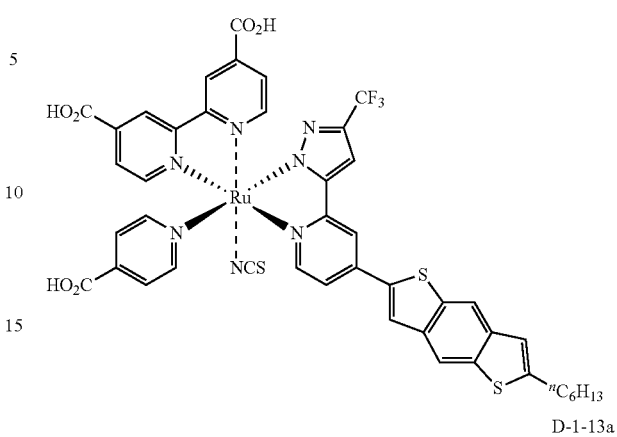
D-1-13a
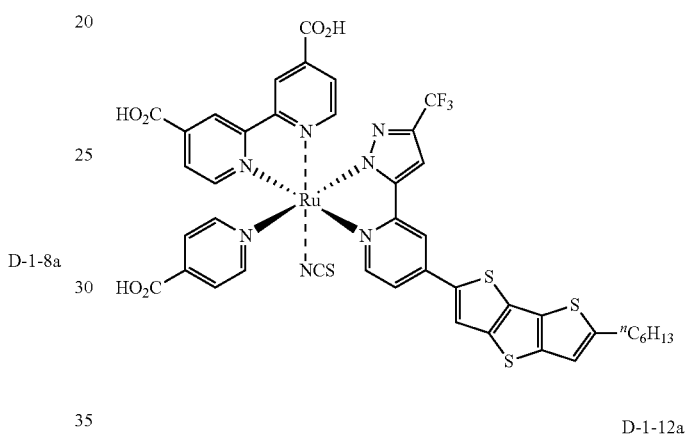
D-1-12a
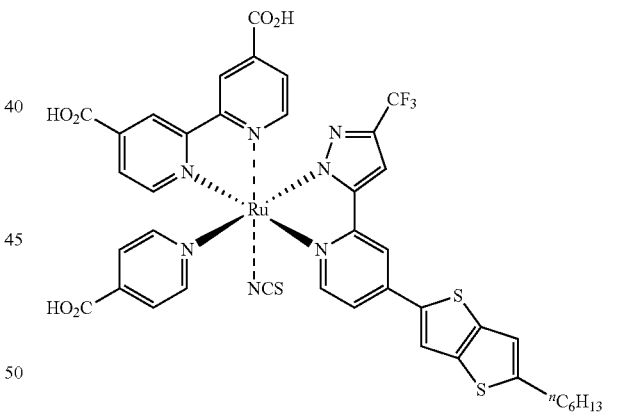
D-1-2a -continued
D-1-23a
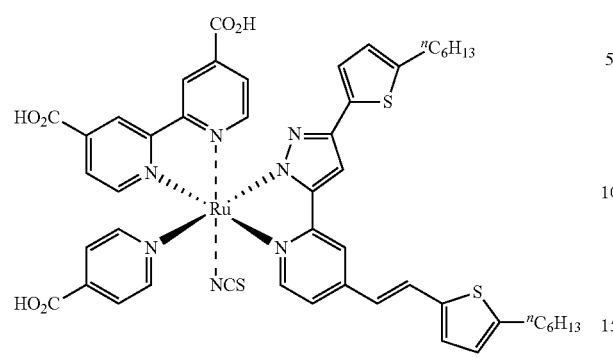
D-1-27a
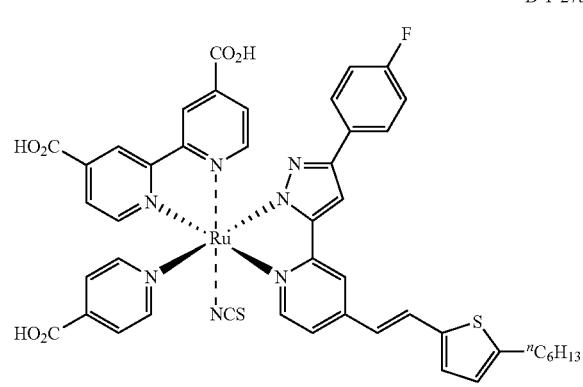
D-1-7a
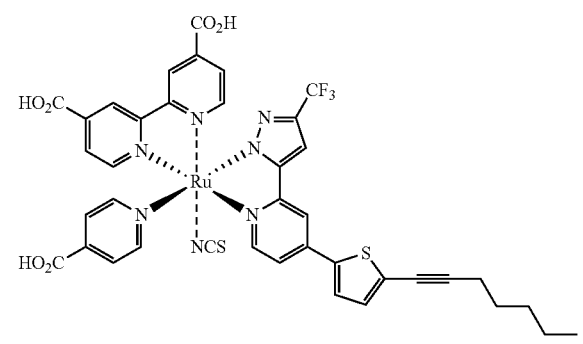
D-1-1a
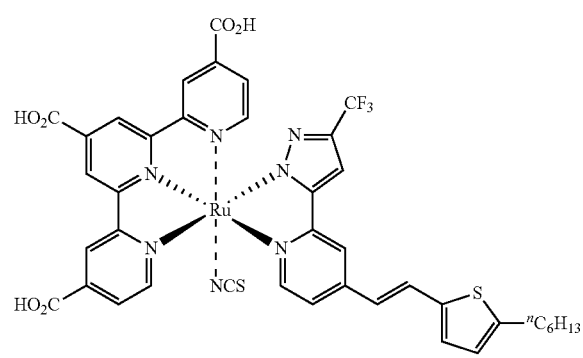
-continued
D-1-5a
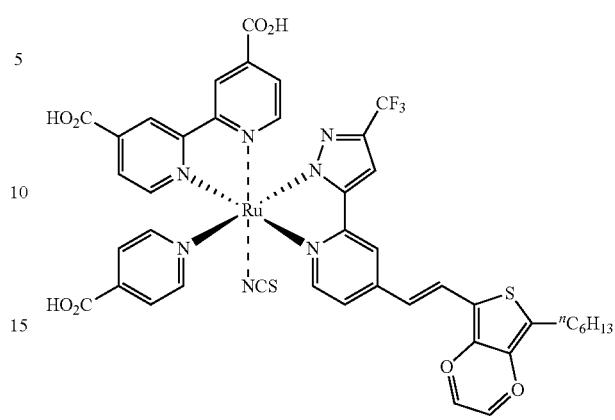
D-1-6a
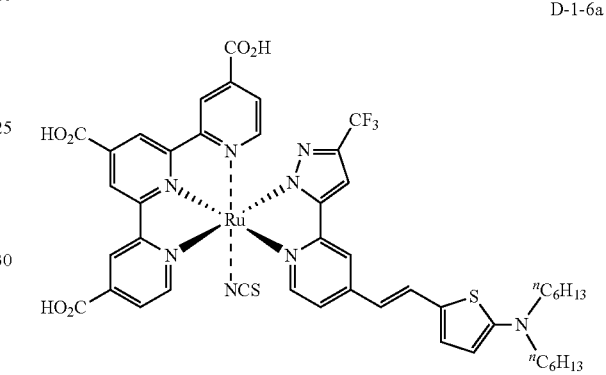
D-3-5a
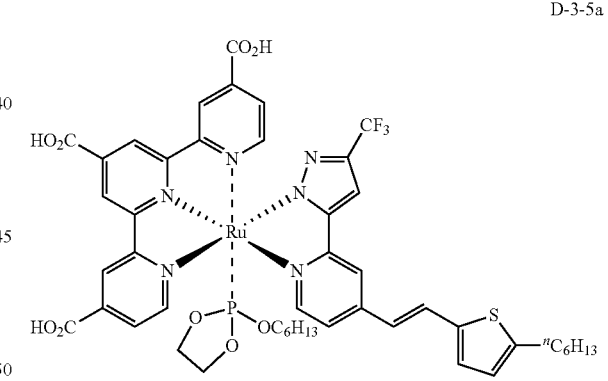
D-1-32a
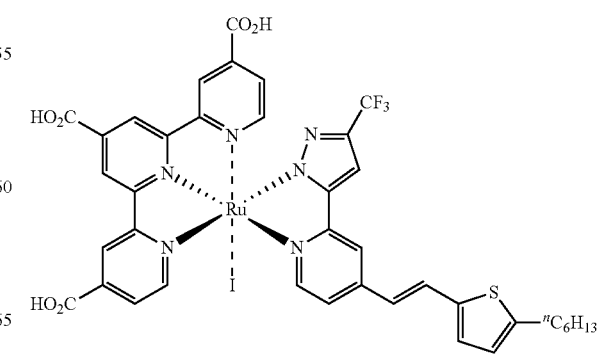

-continued
D-1-38a
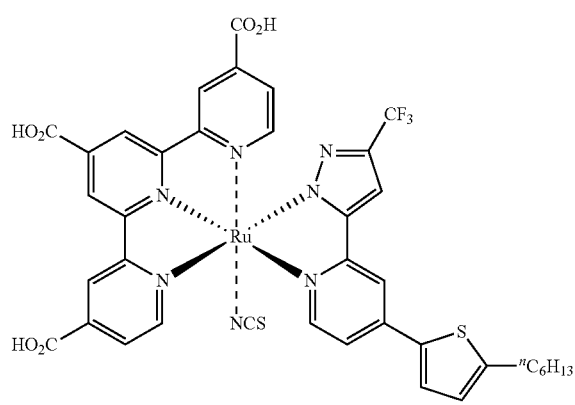
D-1-15a
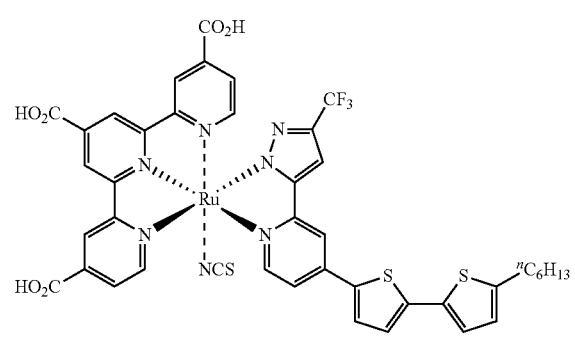
D-1-35a
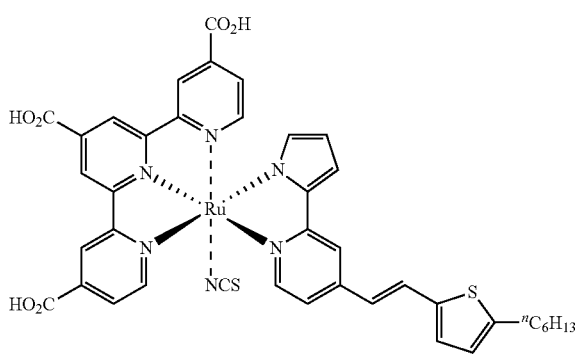
D-1-36a
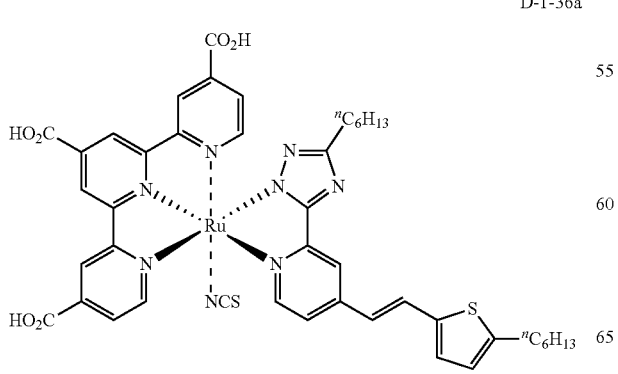
-continued
D-1-37a
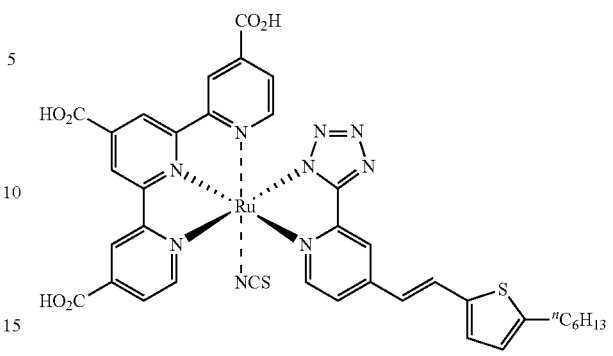
D-2-8a
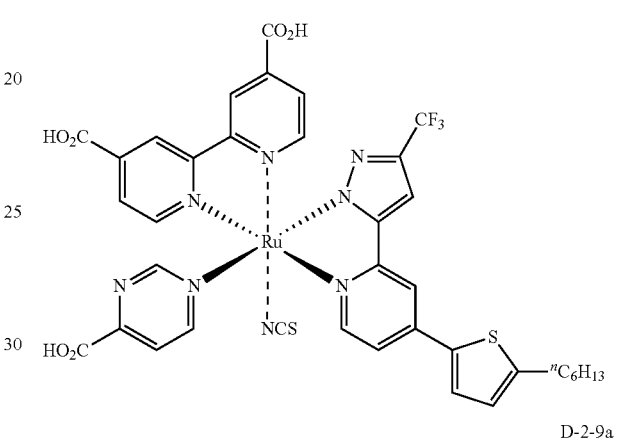
D-2-9a
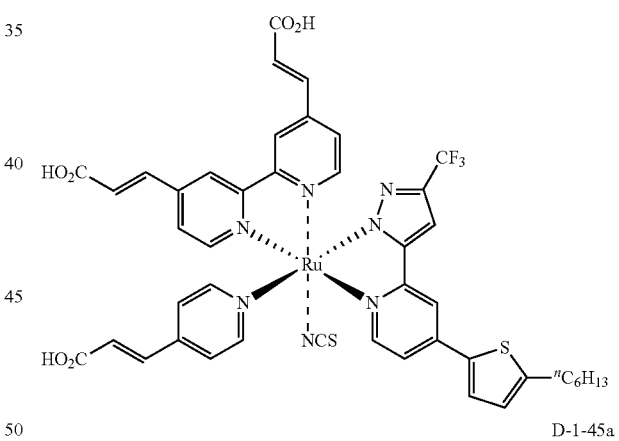
D-1-45a
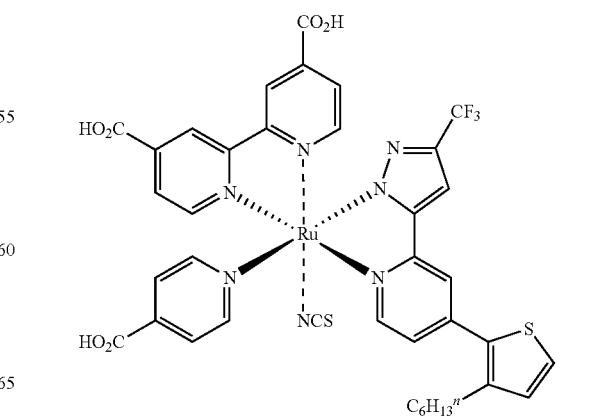

-continued
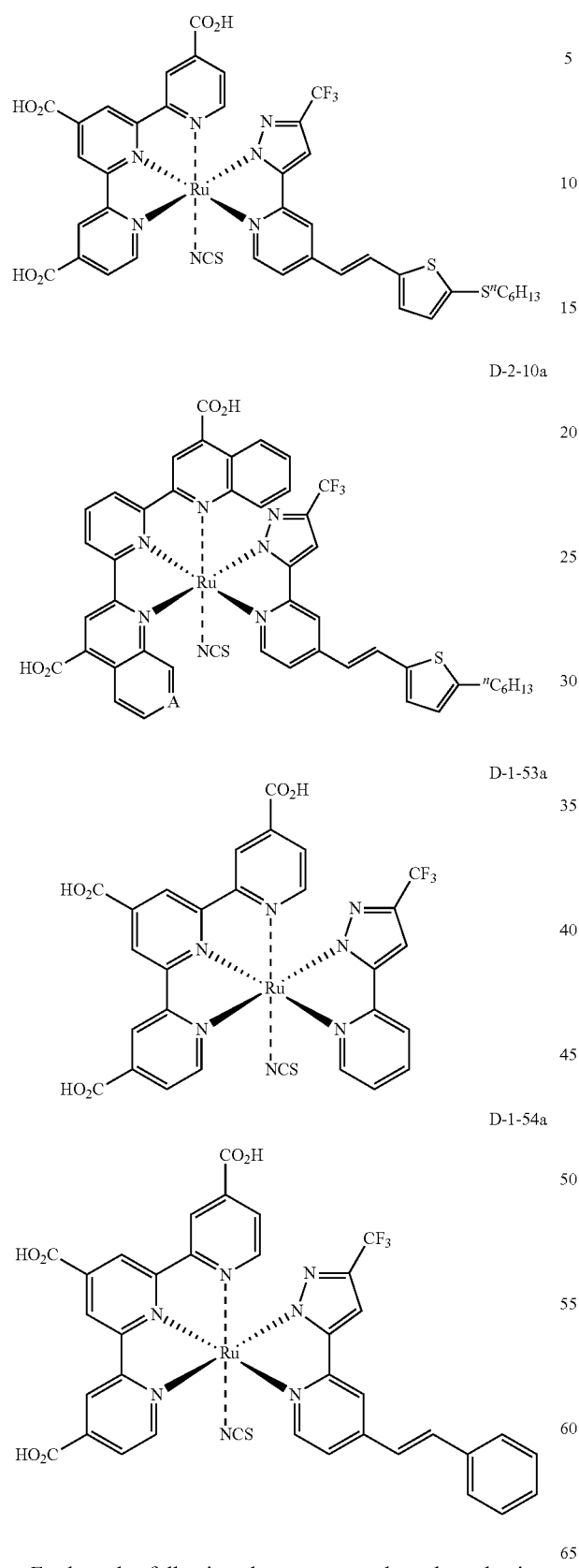
D-1-46a
D-2-10a
D-1-53a
D-1-54a
Further, the following dyes were used as those having comparative dye skeletons.
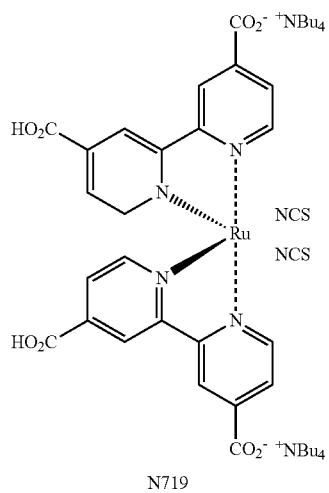
Comparative Dye D-1
N719
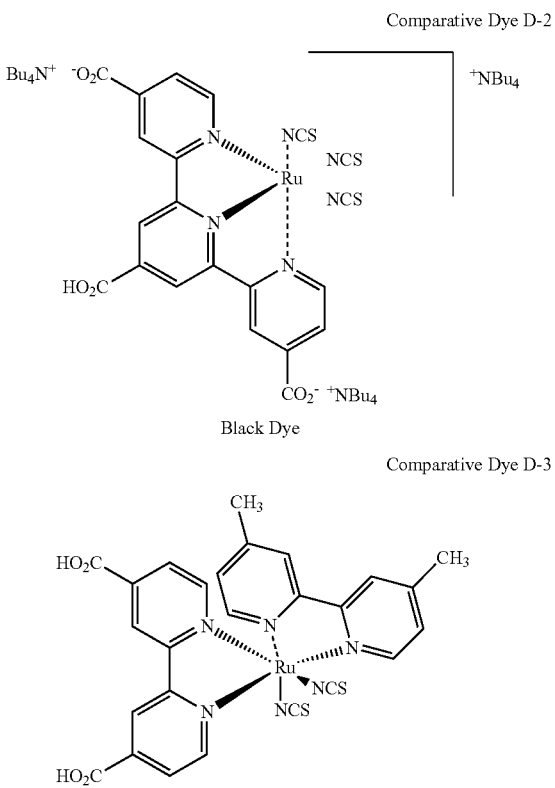
Comparative Dye D-2
Black Dye
Comparative Dye D-3
Comparative Dye D-4

Note that a partial salt-making was carried out by the dye control as described below using dye skeletons of the metal complex dye synthesized as described above, together with the comparative dyes.

[Dye Control]

A 0.05 mol/l methanol solution of each of the above-synthesized metal complex dyes (in each of the dyes, a carboxylate salt is non-existent) was prepared, and a methanol solution prepared with each of the bases shown in the following Tables 2 to 9 so as to be 0.01 mol/l was added thereto only in an amount shown in the following Tables 2 to 9 whereby a partial salt-making was carried out.

The methanol solution containing the partially salt-made metal complex dye was concentrated to obtain a final metal complex dye.

Note that the above-synthesized metal complex dye in which a carboxylate salt is non-existent and the final metal complex dye after addition of the base were able to be confirmed by acid-base neutralization titration. The carboxylate salt which was formed in proportion to the amount of the base was confirmed.

TABLE 2

| Metal complex dye | Dye skeleton | Base Kind | Addition amount in terms of mole per 1 mol of dye |
|---|---|---|---|
| Dye 1 | D-1-1a | KOH | 0.3 |
| Dye 2 | D-1-1a | KOH | 0.5 |
| Dye 3 | D-1-1a | KOH | 0.6 |
| Dye 4 | D-1-1a | KOH | 0.7 |
| Dye 5 | D-1-1a | KOH | 0.8 |
| Dye 6 | D-1-1a | KOH | 1 |
| Dye 7 | D-1-1a | KOH | 1.1 |
| Dye 8 | D-1-1a | KOH | 1.2 |
| Dye 9 | D-1-1a | KOH | 1.3 |
| Dye 10 | D-1-1a | KOH | 1.4 |
| Dye 11 | D-1-1a | KOH | 1.5 |
| Dye 12 | D-1-1a | KOH | 1.6 |
| Dye 13 | D-1-1a | KOH | 2 |
| Dye 14 | D-1-1a | KOH | 2.1 |
| Dye 15 | D-1-1a | KOH | 2.2 |
| Dye 16 | D-1-1a | KOH | 2.7 |
| Dye 17 | D-1-1a | CsOH | 1 |
| Dye 18 | D-1-38a | KOH | 0.3 |
| Dye 19 | D-1-38a | KOH | 0.5 |
| Dye 20 | D-1-38a | KOH | 0.6 |
| Dye 21 | D-1-38a | KOH | 0.7 |
| Dye 22 | D-1-38a | KOH | 0.8 |
| Dye 23 | D-1-38a | KOH | 1 |
| Dye 24 | D-1-38a | KOH | 1.1 |
| Dye 25 | D-1-38a | KOH | 1.2 |
| Dye 26 | D-1-38a | KOH | 1.3 |
| Dye 27 | D-1-38a | KOH | 1.4 |
| Dye 28 | D-1-38a | KOH | 1.5 |
| Dye 29 | D-1-38a | KOH | 1.6 |
| Dye 30 | D-1-38a | KOH | 2 |
| Dye 31 | D-1-38a | KOH | 2.1 |
| Dye 32 | D-1-38a | KOH | 2.2 |
| Dye 33 | D-1-38a | KOH | 2.7 |
| Dye 34 | D-1-5a | KOH | 0.3 |
| Dye 35 | D-1-5a | KOH | 0.5 |
| Dye 36 | D-1-5a | KOH | 0.6 |
| Dye 37 | D-1-5a | KOH | 0.7 |
| Dye 38 | D-1-5a | KOH | 0.8 |
| Dye 39 | D-1-5a | KOH | 1 |
| Dye 40 | D-1-5a | KOH | 1.1 |
| Dye 41 | D-1-5a | KOH | 1.2 |
| Dye 42 | D-1-5a | KOH | 1.3 |
| Dye 43 | D-1-5a | KOH | 1.4 |
| Dye 44 | D-1-5a | KOH | 1.5 |
| Dye 45 | D-1-5a | KOH | 1.6 |
| Dye 46 | D-1-5a | KOH | 2 |
| Dye 47 | D-1-5a | KOH | 2.1 |
| Dye 48 | D-1-5a | KOH | 2.2 |
| Dye 49 | D-1-5a | KOH | 2.7 |
| Dye 50 | D-1-54a | KOH | 0.3 |

TABLE 3

| Metal complex dye | Dye skeleton | Base Kind | Addition amount in terms of mole per 1 mol of dye |
|---|---|---|---|
| Dye 51 | D-1-54a | KOH | 0.5 |
| Dye 52 | D-1-54a | KOH | 0.6 |
| Dye 53 | D-1-54a | KOH | 0.7 |
| Dye 54 | D-1-54a | KOH | 0.8 |
| Dye 55 | D-1-54a | KOH | 1 |
| Dye 56 | D-1-54a | KOH | 1.1 |
| Dye 57 | D-1-54a | KOH | 1.2 |
| Dye 58 | D-1-54a | KOH | 1.3 |
| Dye 59 | D-1-54a | KOH | 1.4 |
| Dye 60 | D-1-54a | KOH | 1.5 |
| Dye 61 | D-1-54a | KOH | 1.6 |
| Dye 62 | D-1-54a | KOH | 2 |
| Dye 63 | D-1-54a | KOH | 2.1 |
| Dye 64 | D-1-54a | KOH | 2.2 |
| Dye 65 | D-1-54a | KOH | 2.7 |
| Dye 66 | D-1-54a | CsOH | 0.3 |
| Dye 67 | D-1-54a | CsOH | 0.5 |
| Dye 68 | D-1-54a | CsOH | 0.6 |
| Dye 69 | D-1-54a | CsOH | 0.7 |
| Dye 70 | D-1-54a | CsOH | 0.8 |
| Dye 71 | D-1-54a | CsOH | 1 |
| Dye 72 | D-1-54a | CsOH | 1.1 |
| Dye 73 | D-1-54a | CsOH | 1.2 |
| Dye 74 | D-1-54a | CsOH | 1.3 |
| Dye 75 | D-1-54a | CsOH | 1.4 |
| Dye 76 | D-1-54a | CsOH | 1.5 |
| Dye 77 | D-1-54a | CsOH | 1.6 |
| Dye 78 | D-1-54a | CsOH | 2 |
| Dye 79 | D-1-54a | CsOH | 2.1 |
| Dye 80 | D-1-54a | CsOH | 2.2 |
| Dye 81 | D-1-54a | CsOH | 2.7 |
| Dye 82 | D-1-54a | LiOH | 0.3 |
| Dye 83 | D-1-54a | LiOH | 0.5 |
| Dye 84 | D-1-54a | LiOH | 0.6 |
| Dye 85 | D-1-54a | LiOH | 0.7 |
| Dye 86 | D-1-54a | LiOH | 0.8 |
| Dye 87 | D-1-54a | LiOH | 1 |
| Dye 88 | D-1-54a | LiOH | 1.1 |
| Dye 89 | D-1-54a | LiOH | 1.2 |
| Dye 90 | D-1-54a | LiOH | 1.3 |
| Dye 91 | D-1-54a | LiOH | 1.4 |
| Dye 92 | D-1-54a | LiOH | 1.5 |
| Dye 93 | D-1-54a | LiOH | 1.6 |
| Dye 94 | D-1-54a | LiOH | 2 |
| Dye 95 | D-1-54a | LiOH | 2.1 |
| Dye 96 | D-1-54a | LiOH | 2.2 |
| Dye 97 | D-1-54a | LiOH | 2.7 |
| Dye 98 | D-2-8a | KOH | 0.3 |
| Dye 99 | D-2-8a | KOH | 0.5 |
| Dye 100 | D-2-8a | KOH | 0.6 |

TABLE 4

| Metal complex dye | Dye skeleton | Base Kind | Addition amount in terms of mole per 1 mol of dye |
|---|---|---|---|
| Dye 101 | D-2-8a | KOH | 0.7 |
| Dye 102 | D-2-8a | KOH | 0.8 |

TABLE 4-continued

| Metal complex dye | Dye skeleton | Base Kind | Addition amount in terms of mole per 1 mol of dye |
|---|---|---|---|
| Dye 103 | D-2-8a | KOH | 1 |
| Dye 104 | D-2-8a | KOH | 1.1 |
| Dye 105 | D-2-8a | KOH | 1.2 |
| Dye 106 | D-2-8a | KOH | 1.3 |
| Dye 107 | D-2-8a | KOH | 1.4 |
| Dye 108 | D-2-8a | KOH | 1.5 |
| Dye 109 | D-2-8a | KOH | 1.6 |
| Dye 110 | D-2-8a | KOH | 2 |
| Dye 111 | D-2-8a | KOH | 2.1 |
| Dye 112 | D-2-8a | KOH | 2.2 |
| Dye 113 | D-2-8a | KOH | 2.7 |
| Dye 114 | D-2-10a | KOH | 0.2 |
| Dye 115 | D-2-10a | KOH | 0.25 |
| Dye 116 | D-2-10a | KOH | 0.3 |
| Dye 117 | D-2-10a | KOH | 0.35 |
| Dye 118 | D-2-10a | KOH | 0.4 |
| Dye 119 | D-2-10a | KOH | 0.45 |
| Dye 120 | D-2-10a | KOH | 0.5 |
| Dye 121 | D-2-10a | KOH | 0.6 |
| Dye 122 | D-2-10a | KOH | 0.8 |
| Dye 123 | D-2-10a | KOH | 0.85 |
| Dye 124 | D-2-10a | KOH | 0.9 |
| Dye 125 | D-2-10a | KOH | 1 |
| Dye 126 | D-2-10a | KOH | 1.05 |
| Dye 127 | D-2-10a | KOH | 1.1 |
| Dye 128 | D-2-10a | KOH | 1.2 |
| Dye 129 | D-2-10a | KOH | 1.8 |
| Dye 130 | D-1-6a | KOH | 0.5 |
| Dye 131 | D-1-6a | KOH | 0.7 |
| Dye 132 | D-1-6a | KOH | 1 |
| Dye 133 | D-1-6a | KOH | 1.3 |
| Dye 134 | D-1-6a | KOH | 2 |
| Dye 135 | D-1-6a | KOH | 2.5 |
| Dye 136 | D-1-7a | KOH | 0.5 |
| Dye 137 | D-1-7a | KOH | 0.7 |
| Dye 138 | D-1-7a | KOH | 1 |
| Dye 139 | D-1-7a | KOH | 1.3 |
| Dye 140 | D-1-7a | KOH | 2 |
| Dye 141 | D-1-7a | KOH | 2.5 |
| Dye 142 | D-1-8a | KOH | 0.5 |
| Dye 143 | D-1-8a | KOH | 0.7 |
| Dye 144 | D-1-8a | KOH | 1 |
| Dye 145 | D-1-8a | KOH | 1.3 |
| Dye 146 | D-1-8a | KOH | 2 |
| Dye 147 | D-1-8a | KOH | 2.5 |
| Dye 148 | D-1-15a | KOH | 0.5 |
| Dye 149 | D-1-15a | KOH | 0.7 |
| Dye 150 | D-1-15a | KOH | 1 |

TABLE 5

| Metal complex dye | Dye skeleton | Base Kind | Addition amount in terms of mole per 1 mol of dye |
|---|---|---|---|
| Dye 151 | D-1-15a | KOH | 1.3 |
| Dye 152 | D-1-15a | KOH | 2 |
| Dye 153 | D-1-15a | KOH | 2.5 |
| Dye 154 | D-1-32a | KOH | 0.5 |
| Dye 155 | D-1-32a | KOH | 0.7 |
| Dye 156 | D-1-32a | KOH | 1 |
| Dye 157 | D-1-32a | KOH | 1.3 |
| Dye 158 | D-1-32a | KOH | 2 |
| Dye 159 | D-1-32a | KOH | 2.5 |
| Dye 160 | D-1-45a | KOH | 0.5 |
| Dye 161 | D-1-45a | KOH | 0.7 |
| Dye 162 | D-1-45a | KOH | 1 |
| Dye 163 | D-1-45a | KOH | 1.3 |
| Dye 164 | D-1-45a | KOH | 2 |
| Dye 165 | D-1-45a | KOH | 2.5 |
| Dye 166 | D-1-46a | KOH | 0.5 |

TABLE 5-continued

| Metal complex dye | Dye skeleton | Base Kind | Addition amount in terms of mole per 1 mol of dye |
|---|---|---|---|
| Dye 167 | D-1-46a | KOH | 0.7 |
| Dye 168 | D-1-46a | KOH | 1 |
| Dye 169 | D-1-46a | KOH | 1.3 |
| Dye 170 | D-1-46a | KOH | 2 |
| Dye 171 | D-1-46a | KOH | 2.5 |
| Dye 172 | D-1-53a | KOH | 0.5 |
| Dye 173 | D-1-53a | KOH | 0.7 |
| Dye 174 | D-1-53a | KOH | 1 |
| Dye 175 | D-1-53a | KOH | 1.3 |
| Dye 176 | D-1-53a | KOH | 2 |
| Dye 177 | D-1-53a | KOH | 2.5 |
| Dye 178 | D-3-5a | KOH | 0.5 |
| Dye 179 | D-3-5a | KOH | 0.7 |
| Dye 180 | D-3-5a | KOH | 1 |
| Dye 181 | D-3-5a | KOH | 1.3 |
| Dye 182 | D-3-5a | KOH | 2 |
| Dye 183 | D-3-5a | KOH | 2.5 |
| Dye 184 | D-1-2a | KOH | 0.5 |
| Dye 185 | D-1-2a | KOH | 0.7 |
| Dye 186 | D-1-2a | KOH | 1 |
| Dye 187 | D-1-2a | KOH | 1.3 |
| Dye 188 | D-1-2a | KOH | 2 |
| Dye 189 | D-1-2a | KOH | 2.5 |
| Dye 190 | D-1-9a | KOH | 0.5 |
| Dye 191 | D-1-9a | KOH | 0.7 |
| Dye 192 | D-1-9a | KOH | 1 |
| Dye 193 | D-1-9a | KOH | 1.3 |
| Dye 194 | D-1-9a | KOH | 2 |
| Dye 195 | D-1-9a | KOH | 2.5 |
| Dye 196 | D-1-12a | KOH | 0.5 |
| Dye 197 | D-1-12a | KOH | 0.7 |
| Dye 198 | D-1-12a | KOH | 1 |
| Dye 199 | D-1-12a | KOH | 1.3 |
| Dye 200 | D-1-12a | KOH | 2 |

TABLE 6

| Metal complex dye | Dye skeleton | Base Kind | Addition amount in terms of mole per 1 mol of dye |
|---|---|---|---|
| Dye 201 | D-1-12a | KOH | 2.5 |
| Dye 202 | D-1-13a | KOH | 0.5 |
| Dye 203 | D-1-13a | KOH | 0.7 |
| Dye 204 | D-1-13a | KOH | 1 |
| Dye 205 | D-1-13a | KOH | 1.3 |
| Dye 206 | D-1-13a | KOH | 2 |
| Dye 207 | D-1-13a | KOH | 2.5 |
| Dye 208 | D-1-14a | KOH | 0.5 |
| Dye 209 | D-1-14a | KOH | 0.7 |
| Dye 210 | D-1-14a | KOH | 1 |
| Dye 211 | D-1-14a | KOH | 1.3 |
| Dye 212 | D-1-14a | KOH | 2 |
| Dye 213 | D-1-14a | KOH | 2.5 |
| Dye 214 | D-1-16a | KOH | 0.5 |
| Dye 215 | D-1-16a | KOH | 0.7 |
| Dye 216 | D-1-16a | KOH | 1 |
| Dye 217 | D-1-16a | KOH | 1.3 |
| Dye 218 | D-1-16a | KOH | 2 |
| Dye 219 | D-1-16a | KOH | 2.5 |
| Dye 220 | D-1-18a | KOH | 0.5 |
| Dye 221 | D-1-18a | KOH | 0.7 |
| Dye 222 | D-1-18a | KOH | 1 |
| Dye 223 | D-1-18a | KOH | 1.3 |
| Dye 224 | D-1-18a | KOH | 2 |
| Dye 225 | D-1-18a | KOH | 2.5 |
| Dye 226 | D-3-1a | KOH | 0.5 |
| Dye 227 | D-3-1a | KOH | 0.7 |
| Dye 228 | D-3-1a | KOH | 1 |
| Dye 229 | D-3-1a | KOH | 1.3 |
| Dye 230 | D-3-1a | KOH | 2 |

TABLE 6-continued

| Metal complex dye | Dye skeleton | Base Kind | Addition amount in terms of mole per 1 mol of dye |
|---|---|---|---|
| Dye 231 | D-3-1a | KOH | 2.5 |
| Dye 232 | D-1-23a | KOH | 0.5 |
| Dye 233 | D-1-23a | KOH | 0.7 |
| Dye 234 | D-1-23a | KOH | 1 |
| Dye 235 | D-1-23a | KOH | 1.3 |
| Dye 236 | D-1-23a | KOH | 2 |
| Dye 237 | D-1-23a | KOH | 2.5 |
| Dye 238 | D-1-26a | KOH | 0.5 |
| Dye 239 | D-1-26a | KOH | 0.7 |
| Dye 240 | D-1-26a | KOH | 1 |
| Dye 241 | D-1-26a | KOH | 1.3 |
| Dye 242 | D-1-26a | KOH | 2 |
| Dye 243 | D-1-26a | KOH | 2.5 |
| Dye 244 | D-1-27a | KOH | 0.5 |
| Dye 245 | D-1-27a | KOH | 0.7 |
| Dye 246 | D-1-27a | KOH | 1 |
| Dye 247 | D-1-27a | KOH | 1.3 |
| Dye 248 | D-1-27a | KOH | 2 |
| Dye 249 | D-1-27a | KOH | 2.5 |
| Dye 250 | D-1-35a | KOH | 0.5 |

TABLE 7

| Metal complex dye | Dye skeleton | Base Kind | Addition amount in terms of mole per 1 mol of dye |
|---|---|---|---|
| Dye 251 | D-1-35a | KOH | 0.7 |
| Dye 252 | D-1-35a | KOH | 1 |
| Dye 253 | D-1-35a | KOH | 1.3 |
| Dye 254 | D-1-35a | KOH | 2 |
| Dye 255 | D-1-35a | KOH | 2.5 |
| Dye 256 | D-1-36a | KOH | 0.5 |
| Dye 257 | D-1-36a | KOH | 0.7 |
| Dye 258 | D-1-36a | KOH | 1 |
| Dye 259 | D-1-36a | KOH | 1.3 |
| Dye 260 | D-1-36a | KOH | 2 |
| Dye 261 | D-1-36a | KOH | 2.5 |
| Dye 262 | D-1-37a | KOH | 0.5 |
| Dye 263 | D-1-37a | KOH | 0.7 |
| Dye 264 | D-1-37a | KOH | 1 |
| Dye 265 | D-1-37a | KOH | 1.3 |
| Dye 266 | D-1-37a | KOH | 2 |
| Dye 267 | D-1-37a | KOH | 2.5 |
| Dye 268 | D-2-9a | KOH | 0.5 |
| Dye 269 | D-2-9a | KOH | 0.7 |
| Dye 270 | D-2-9a | KOH | 1 |
| Dye 271 | D-2-9a | KOH | 1.3 |
| Dye 272 | D-2-9a | KOH | 2 |
| Dye 273 | D-2-9a | KOH | 2.5 |
| Dye 274 | D-1-5a | LiOH | 1 |
| Dye 275 | D-1-5a | CsOH | 1 |
| Dye 276 | D-1-6a | LiOH | 1 |
| Dye 277 | D-1-6a | CsOH | 1 |
| Dye 278 | D-1-8a | LiOH | 1 |
| Dye 279 | D-1-8a | CsOH | 1 |
| Dye 280 | D-1-15a | LiOH | 1 |
| Dye 281 | D-1-15a | CsOH | 1 |
| Dye 282 | D-1-32a | LiOH | 1 |
| Dye 283 | D-1-32a | CsOH | 1 |
| Dye 284 | D-1-38a | LiOH | 1 |
| Dye 285 | D-1-38a | CsOH | 1 |
| Dye 286 | D-1-45a | LiOH | 1 |
| Dye 287 | D-1-45a | CsOH | 1 |
| Dye 288 | D-1-46a | LiOH | 1 |
| Dye 289 | D-1-46a | CsOH | 1 |
| Dye 290 | D-1-53a | LiOH | 1 |
| Dye 291 | D-1-53a | CsOH | 1 |
| Dye 292 | D-3-5a | LiOH | 1 |
| Dye 293 | D-3-5a | CsOH | 1 |
| Dye 294 | D-1-2a | LiOH | 1 |

TABLE 7-continued

| Metal complex dye | Dye skeleton | Base Kind | Addition amount in terms of mole per 1 mol of dye |
|---|---|---|---|
| Dye 295 | D-1-2a | CsOH | 1 |
| Dye 296 | D-1-9a | LiOH | 1 |
| Dye 297 | D-1-9a | CsOH | 1 |
| Dye 298 | D-1-12a | LiOH | 1 |
| Dye 299 | D-1-12a | CsOH | 1 |
| Dye 300 | D-1-13a | LiOH | 1 |

TABLE 8

| Metal complex dye | Dye skeleton | Base Kind | Addition amount in terms of mole per 1 mol of dye |
|---|---|---|---|
| Dye 301 | D-1-13a | CsOH | 1 |
| Dye 302 | D-1-14a | LiOH | 1 |
| Dye 303 | D-1-14a | CsOH | 1 |
| Dye 304 | D-1-16a | LiOH | 1 |
| Dye 305 | D-1-16a | CsOH | 1 |
| Dye 306 | D-1-18a | LiOH | 1 |
| Dye 307 | D-1-18a | CsOH | 1 |
| Dye 308 | D-3-1a | LiOH | 1 |
| Dye 309 | D-3-1a | CsOH | 1 |
| Dye 310 | D-1-23a | LiOH | 1 |
| Dye 311 | D-1-23a | CsOH | 1 |
| Dye 312 | D-1-26a | LiOH | 1 |
| Dye 313 | D-1-26a | CsOH | 1 |
| Dye 314 | D-1-27a | LiOH | 1 |
| Dye 315 | D-1-27a | CsOH | 1 |
| Dye 316 | D-1-35a | LiOH | 1 |
| Dye 317 | D-1-35a | CsOH | 1 |
| Dye 318 | D-1-36a | LiOH | 1 |
| Dye 319 | D-1-36a | CsOH | 1 |
| Dye 320 | D-1-37a | LiOH | 1 |
| Dye 321 | D-1-37a | CsOH | 1 |
| Dye 322 | D-2-9a | LiOH | 1 |
| Dye 323 | D-2-9a | CsOH | 1 |
| Dye 324 | D-2-8a | LiOH | 1 |
| Dye 325 | D-2-8a | CsOH | 1 |
| Dye 326 | D-2-10a | LiOH | 1 |
| Dye 327 | D-2-10a | CsOH | 1 |
| Dye 328 | D-1-48a | LiOH | 1 |
| Dye 329 | D-1-48a | CsOH | 1 |

TABLE 9

| Metal complex dye | Dye skeleton | Base Kind | Addition amount in terms of mole per 1 mol of dye |
|---|---|---|---|
| Comparative Dye c1 | D-1-38a | — | 0 |
| Comparative Dye c2 | D-1-38a | KOH | 0.2 |
| Comparative Dye c3 | D-1-38a | KOH | 2.8 |
| Comparative Dye c4 | D-1-38a | KOH | 3 |
| Comparative Dye c5 | D-2-10a | — | 0 |
| Comparative Dye c6 | D-2-10a | KOH | 0.1 |
| Comparative Dye c7 | D-2-10a | KOH | 1.9 |
| Comparative Dye c8 | D-2-10a | KOH | 2 |
| Comparative Dye c9 | D-2-8a | — | 0 |
| Comparative Dye c10 | D-2-8a | KOH | 0.2 |
| Comparative Dye c11 | D-2-8a | KOH | 2.8 |
| Comparative Dye c12 | D-2-8a | KOH | 3 |
| Comparative Dye c13 | D-1-54a | — | 0 |
| Comparative Dye c14 | D-1-54a | NaOH | 0.2 |
| Comparative Dye c15 | D-1-54a | NaOH | 1 |
| Comparative Dye c16 | D-1-54a | NaOH | 1.5 |

TABLE 9-continued

| Metal complex dye | Dye skeleton | Base Kind | Addition amount in terms of mole per 1 mol of dye |
|---|---|---|---|
| Comparative Dye c17 | D-1-54a | NaOH | 2 |
| Comparative Dye c18 | D-1-54a | NaOH | 2.8 |
| Comparative Dye c19 | D-1-54a | NaOH | 3 |
| Comparative Dye c20 | D-1-54a | KOH | 0.2 |
| Comparative Dye c21 | D-1-54a | KOH | 2.8 |
| Comparative Dye c22 | D-1-54a | KOH | 3 |
| Comparative Dye c23 | D-1-54a | CsOH | 0.2 |
| Comparative Dye c24 | D-1-54a | CsOH | 2.8 |
| Comparative Dye c25 | D-1-54a | CsOH | 3 |
| Comparative Dye c26 | D-1-54a | LiOH | 0.2 |
| Comparative Dye c27 | D-1-54a | LiOH | 2.8 |
| Comparative Dye c28 | D-1-54a | LiOH | 3 |
| Comparative Dye c29 | D-1-54a | NnBu$_4$OH | 0.2 |
| Comparative Dye c30 | D-1-54a | NnBu$_4$OH | 1 |
| Comparative Dye c31 | D-1-54a | NnBu$_4$OH | 1.5 |
| Comparative Dye c32 | D-1-54a | NnBu$_4$OH | 2 |
| Comparative Dye c33 | D-1-54a | NnBu$_4$OH | 2.8 |
| Comparative Dye c34 | D-1-54a | NnBu$_4$OH | 3 |
| Comparative Dye c35 | Comparative Dye D-1 | — | 0 |
| Comparative Dye c36 | Comparative Dye D-2 | — | 0 |
| Comparative Dye c37 | Comparative Dye D-3 | — | 0 |
| Comparative Dye c38 | Comparative Dye D-3 | NaOH | 0.5 |
| Comparative Dye c39 | Comparative Dye D-3 | NaOH | 1 |
| Comparative Dye c40 | Comparative Dye D-3 | NaOH | 1.5 |
| Comparative Dye c41 | Comparative Dye D-3 | NaOH | 2 |
| Comparative Dye c42 | Comparative Dye D-3 | NnBu$_4$OH | 0.5 |
| Comparative Dye c43 | Comparative Dye D-3 | NnBu$_4$OH | 1 |
| Comparative Dye c44 | Comparative Dye D-3 | NnBu$_4$OH | 1.5 |
| Comparative Dye c45 | Comparative Dye D-3 | NnBu$_4$OH | 2 |
| Comparative Dye c46 | Comparative Dye D-4 | — | 0 |
| Comparative Dye c47 | Comparative Dye D-4 | NaOH | 1 |
| Comparative Dye c48 | Comparative Dye D-4 | NaOH | 4 |
| Comparative Dye c49 | Comparative Dye D-5 | — | 0 |
| Comparative Dye c50 | Comparative Dye D-5 | NaOH | 3 |

[Preparation of Dye Solution]

The metal complex dyes shown in the above Tables 2 to 9 and a solution of t-butanol/acetonitrile=1/1 (volume ratio) were weighed and mixed in such a way that when the metal complex dye is completely dissolved in the solution of t-butanol/acetonitrile=1/1 (volume ratio), the dye concentration is $2 \times 10^{-4}$ mol/L, and then the mixture was stirred under the condition of 40° C. for 2 hours in a dark place.

[Measurement of Turbidity]

Turbidity was measured using an integrating turbidity meter PT-200 type Turbidity Meter (manufactured by Mitsubishi Chemical Analytech Co., Ltd.) and using a kaolin standard solution (manufactured by Kishida Chemical Co., Ltd.). Turbidity was evaluated in accordance with the following evaluation criteria.

Evaluation Criteria

AA: The turbidity was 0 ppm or more and less than 10 ppm.
A: The turbidity was 10 ppm or more and less than 20 ppm.
B: The turbidity was 20 ppm or more and less than 30 ppm.
C: The turbidity was 30 ppm or more and less than 45 ppm.
D: The turbidity was 45 ppm or more and less than 60 ppm.
E: The turbidity was 60 ppm or more and less than 75 ppm.
F: The turbidity was 75 ppm or more and less than 90 ppm.
G: The turbidity was 90 ppm or more and less than 105 ppm.
H: The turbidity was 105 ppm or more and less than 120 ppm.
I: The turbidity was 120 ppm or more and less than 135 ppm.
J: The turbidity was 135 ppm or more and less than 150 ppm.
K: The turbidity was 150 ppm or more and less than 200 ppm.
L: The turbidity was 200 ppm or more and less than 300 ppm.
M: The turbidity was 300 ppm or more.

Here, the higher the value of turbidity, the more the undissolved residue of the dye is, and therefore the turbidity provides an indication of resolvability.

Various kinds of pastes for forming a semiconductor layer or a light-scattering layer of a semiconductor electrode which composes a photoelectrode were prepared. The photoelectrodes were prepared using these pastes and adsorption time was measured.

[Preparation of Paste]

(Paste A)

Spherical $TiO_2$ particles (anatase, a mean particle diameter; 25 nm or less, hereinafter, referred to as spherical $TiO_2$ particles A) were put into a nitric acid solution, and the resultant mixture was stirred to prepare titania slurry. Next, a cellulose-based binder was added to the titania slurry as a thickening agent, and the resultant mixture was kneaded to prepare a paste.

(Paste 1)

Spherical $TiO_2$ particles A and spherical $TiO_2$ particles (anatase, a mean particle diameter; 200 nm or less, hereinafter, referred to as spherical $TiO_2$ particles B) were put into a nitric acid solution, and the resultant mixture was stirred to prepare titania slurry. Next, a cellulose-based binder was added to the titania slurry as a thickening agent, and the resultant mixture was kneaded to prepare a paste ((a mass of $TiO_2$ particles A):(a mass of $TiO_2$ particles B)=30:70).

(Paste 2)

Rod-shaped $TiO_2$ particles (anatase, diameter; 100 nm, aspect ratio; 5 or less, hereinafter, referred to as rod-shaped $TiO_2$ particles C) were mixed with the paste A, to prepare a paste having (a mass of rod-shaped $TiO_2$ particles C): (a mass of the paste A)=30:70.

[Production of Photoelectrode]

As described later, a photoelectrode having the same configuration as that of the photoelectrode 12 shown in FIG. 5 of JP-A-2002-289274 was produced, and using the photoelectrode, a dye-sensitized solar cell 1 of a scale of 10 mm×10 mm having the same configuration as that of the dye-sensitized solar cell 20 shown in FIG. 3 of JP-A-2002-289274 except for the photoelectrode, was produced. The specific configuration thereof was shown in FIG. 2 attached to the present application. In FIG. 2 of the present application, 20 denotes a dye-sensitized solar cell, 41 denotes a transparent electrode, 42 denotes a semiconductor electrode, 43 denotes a transparent electrically-conductive film, 44 denotes a substrate, 45 denotes a semiconductor layer, 46 denotes a light-scattering layer, 40 denotes a photoelectrode, CE denotes a counter electrode, E denotes an electrolyte, and S denotes a spacer.

A transparent electrode was prepared in which a fluorine-doped $SnO_2$ electrically-conductive film (thickness: 500 nm) was formed on a glass substrate. On this $SnO_2$ electrically-conductive film, the paste 1 was applied to by screen printing, followed by drying. Then, the paste was calcined under the conditions of 450° C. in the air. Further, by repeating this screen printing and calcination using the paste 2, semiconductor electrode A having the same configuration as that of the semiconductor electrode 42 shown in FIG. 2 of the present application (the area of the light-receiving face: 10 mm×10 mm; the layer thickness: 17 µm; the layer thickness of the dye-adsorbed layer: 12 µm; the layer thickness of the light-scattering layer: 5 µm; and the content of the rod-shaped $TiO_2$ particles C contained in the light-scattering layer: 30% by mass) was formed on the $SnO_2$ electrically-conductive film. Thus, a photoelectrode A, which did not contain a sensitized dye, was prepared.

[Measurement of Adsorption Time]

A semiconductor electrode was immersed in a dye solution prepared by the above method, and was pulled out on a 3 hour basis and dye adsorption amounts were each measured. The time necessary to adsorb 0.16 µmol/cm² of the dye on the semiconductor electrode was defined as an adsorption time. Thus, a photoelectrode 40 was completed.

Note that in measurement of the adsorption amount, the photoelectrode on which the dye adsorbed was washed with a methanol solution of tetrabutyl ammonium hydroxide to desorb the dye, and then measurement of solution absorption was carried out to determine quantity.

[Preparation of Dye-Sensitized Solar Cell]

Then, prepared were, as a counter electrode, a platinum electrode (thickness of Pt thin film: 100 nm) having the same shape and size as those of the photoelectrode, and as an electrolyte E, an iodine-based redox solution containing: 0.05 M iodine, 0.01 M lithium iodide, 0.6 M 1-propyl-3-methylimidazolium iodide and 4-tert-butylpyridine. Further, a spacer-S (trade name: "Surlyn") manufactured by DuPont, which had a shape matching to the size of the semiconductor electrode, was prepared. As shown in FIG. 3 of JP-A-2002-289274, the photoelectrode 40 and the counter electrode CE were arranged to face each other, with the spacer-S interposed therebetween, followed by filling the electrolyte in the inside thereof. Thus, a dye-sensitized solar cell (cell A) composed of a photoelectric conversion element in which the photoelectrode A was utilized, was completed.

[Heat Resistance Test Method]

The heat resistance of the dye-sensitized solar cell was evaluated in terms of decrease rate of photoelectric conversion efficiency measured by standing the prepared dye-sensitized solar cell at 80° C. with age for 200 hours in a dark place.

Photoelectric conversion efficiency η(%), together with the short-circuit current density Jsc (mA/cm²), the open-circuit voltage Voc (mV), and the fill factor FF of each of the dye-sensitized solar cells (cell A), were measured, with irradiating a pseudo sunlight of 1,000 W/m² from a xenon lamp through an AM 1.5 filter, using a solar similator (WXS-85H, manufactured by WACOM). The current-voltage characteristics were thus measured before and after the aging test, using an I-V tester.

The decrease rate (%) of photoelectric conversion efficiency was determined as follows.

[(Initial conversion efficiency−Conversion efficiency after dark aging)/Initial conversion efficiency]×100

As to the adsorption time, 18 hours or less is a level for passing the evaluation criteria. As to the heat resistance test, the decrease rate of 15% or less is a level for passing the evaluation criteria. In the present invention, it is necessary to fulfill both requirements.

The obtained results are shown together in the following Tables 10 to 17.

Here, α is a ratio (number of salt of carboxyl group/total number of carboxyl group and salt of carboxyl group) of the number of a salt of the carboxyl group to the total number of the carboxyl group and the salt of the carboxyl group to be found in 1 mole of the metal complex dye.

Further, the code "x" in the column of Adsorption time in the tables indicates that the adsorption amount has not reached yet the predetermined amount even a lapse of 24 hours.

TABLE 10

| Solar cell No. | Metal complex dye | α | Turbidity | Adsorption time | Heat resistance 80° C. × 200 hr dark place decrease rate (%) | Remarks |
|---|---|---|---|---|---|---|
| 101 | Dye 1 | 0.1 | D | 18 hr | 1 | This invention |
| 102 | Dye 2 | 0.17 | C | 15 hr | 1 | This invention |
| 103 | Dye 3 | 0.2 | B | 9 hr | 1 | This invention |
| 104 | Dye 4 | 0.23 | A | 9 hr | 1 | This invention |
| 105 | Dye 5 | 0.27 | A | 6 hr | 1 | This invention |
| 106 | Dye 6 | 0.33 | AA | 6 hr | 1 | This invention |
| 107 | Dye 7 | 0.37 | AA | 6 hr | 1 | This invention |
| 108 | Dye 8 | 0.4 | AA | 6 hr | 1 | This invention |
| 109 | Dye 9 | 0.43 | AA | 12 hr | 2 | This invention |
| 110 | Dye 10 | 0.47 | AA | 12 hr | 2 | This invention |
| 111 | Dye 11 | 0.5 | AA | 15 hr | 2 | This invention |
| 112 | Dye 12 | 0.53 | AA | 15 hr | 3 | This invention |
| 113 | Dye 13 | 0.67 | AA | 15 hr | 3 | This invention |
| 114 | Dye 14 | 0.7 | AA | 18 hr | 3 | This invention |
| 115 | Dye 15 | 0.73 | AA | 18 hr | 4 | This invention |
| 116 | Dye 16 | 0.9 | AA | 18 hr | 6 | This invention |
| 117 | Dye 17 | 0.33 | AA | 18 hr | 2 | This invention |
| 118 | Dye 18 | 0.1 | D | 18 hr | 1 | This invention |
| 119 | Dye 19 | 0.17 | C | 15 hr | 1 | This invention |
| 120 | Dye 20 | 0.2 | B | 9 hr | 1 | This invention |
| 121 | Dye 21 | 0.23 | A | 9 hr | 1 | This invention |
| 122 | Dye 22 | 0.27 | A | 6 hr | 1 | This invention |
| 123 | Dye 23 | 0.33 | AA | 6 hr | 1 | This invention |
| 124 | Dye 24 | 0.37 | AA | 6 hr | 1 | This invention |
| 125 | Dye 25 | 0.4 | AA | 6 hr | 1 | This invention |
| 126 | Dye 26 | 0.43 | AA | 12 hr | 2 | This invention |
| 127 | Dye 27 | 0.47 | AA | 12 hr | 2 | This invention |
| 128 | Dye 28 | 0.5 | AA | 15 hr | 2 | This invention |
| 129 | Dye 29 | 0.53 | AA | 15 hr | 3 | This invention |

TABLE 10-continued

| Solar cell No. | Metal complex dye | α | Turbidity | Adsorption time | Heat resistance 80° C. × 200 hr dark place decrease rate (%) | Remarks |
|---|---|---|---|---|---|---|
| 130 | Dye 30 | 0.67 | AA | 15 hr | 3 | This invention |
| 131 | Dye 31 | 0.7 | AA | 18 hr | 3 | This invention |
| 132 | Dye 32 | 0.73 | AA | 18 hr | 4 | This invention |
| 133 | Dye 33 | 0.9 | AA | 18 hr | 5 | This invention |
| 134 | Dye 34 | 0.1 | D | 18 hr | 1 | This invention |
| 135 | Dye 35 | 0.17 | C | 15 hr | 1 | This invention |
| 136 | Dye 36 | 0.2 | B | 9 hr | 1 | This invention |
| 137 | Dye 37 | 0.23 | A | 9 hr | 1 | This invention |
| 138 | Dye 38 | 0.27 | A | 6 hr | 1 | This invention |
| 139 | Dye 39 | 0.33 | AA | 6 hr | 1 | This invention |
| 140 | Dye 40 | 0.37 | AA | 6 hr | 1 | This invention |
| 141 | Dye 41 | 0.4 | AA | 6 hr | 1 | This invention |
| 142 | Dye 42 | 0.43 | AA | 12 hr | 2 | This invention |
| 143 | Dye 43 | 0.47 | AA | 12 hr | 2 | This invention |
| 144 | Dye 44 | 0.5 | AA | 15 hr | 2 | This invention |
| 145 | Dye 45 | 0.53 | AA | 15 hr | 3 | This invention |
| 146 | Dye 46 | 0.67 | AA | 15 hr | 3 | This invention |
| 147 | Dye 47 | 0.7 | AA | 18 hr | 3 | This invention |
| 148 | Dye 48 | 0.73 | AA | 18 hr | 4 | This invention |
| 149 | Dye 49 | 0.9 | AA | 18 hr | 7 | This invention |
| 150 | Dye 50 | 0.1 | D | 18 hr | 2 | This invention |

TABLE 11

| Solar cell No. | Metal complex dye | α | Turbidity | Adsorption time | Heat resistance 80° C. × 200 hr dark place decrease rate (%) | Remarks |
|---|---|---|---|---|---|---|
| 151 | Dye 51 | 0.17 | C | 18 hr | 2 | This invention |
| 152 | Dye 52 | 0.2 | B | 12 hr | 2 | This invention |
| 153 | Dye 53 | 0.23 | A | 9 hr | 2 | This invention |
| 154 | Dye 54 | 0.27 | A | 9 hr | 2 | This invention |
| 155 | Dye 55 | 0.33 | AA | 6 hr | 2 | This invention |
| 156 | Dye 56 | 0.37 | AA | 9 hr | 2 | This invention |
| 157 | Dye 57 | 0.4 | AA | 9 hr | 2 | This invention |
| 158 | Dye 58 | 0.43 | AA | 15 hr | 3 | This invention |
| 159 | Dye 59 | 0.47 | AA | 15 hr | 3 | This invention |
| 160 | Dye 60 | 0.5 | AA | 18 hr | 3 | This invention |
| 161 | Dye 61 | 0.53 | AA | 18 hr | 4 | This invention |
| 162 | Dye 62 | 0.67 | AA | 18 hr | 4 | This invention |
| 163 | Dye 63 | 0.7 | AA | 18 hr | 4 | This invention |
| 164 | Dye 64 | 0.73 | AA | 18 hr | 5 | This invention |
| 165 | Dye 65 | 0.9 | AA | 18 hr | 10 | This invention |
| 166 | Dye 66 | 0.1 | D | 18 hr | 3 | This invention |
| 167 | Dye 67 | 0.17 | C | 18 hr | 3 | This invention |
| 168 | Dye 68 | 0.2 | B | 15 hr | 3 | This invention |
| 169 | Dye 69 | 0.23 | A | 12 hr | 3 | This invention |
| 170 | Dye 70 | 0.27 | A | 9 hr | 3 | This invention |
| 171 | Dye 71 | 0.33 | AA | 9 hr | 3 | This invention |
| 172 | Dye 72 | 0.37 | AA | 9 hr | 3 | This invention |
| 173 | Dye 73 | 0.4 | AA | 9 hr | 3 | This invention |
| 174 | Dye 74 | 0.43 | AA | 15 hr | 4 | This invention |
| 175 | Dye 75 | 0.47 | AA | 15 hr | 4 | This invention |
| 176 | Dye 76 | 0.5 | AA | 15 hr | 4 | This invention |
| 177 | Dye 77 | 0.53 | AA | 15 hr | 5 | This invention |
| 178 | Dye 78 | 0.67 | AA | 15 hr | 5 | This invention |
| 179 | Dye 79 | 0.7 | AA | 18 hr | 5 | This invention |
| 180 | Dye 80 | 0.73 | AA | 18 hr | 6 | This invention |
| 181 | Dye 81 | 0.9 | AA | 18 hr | 12 | This invention |
| 182 | Dye 82 | 0.1 | D | 18 hr | 3 | This invention |
| 183 | Dye 83 | 0.17 | C | 18 hr | 3 | This invention |
| 184 | Dye 84 | 0.2 | B | 15 hr | 3 | This invention |
| 185 | Dye 85 | 0.23 | A | 12 hr | 3 | This invention |
| 186 | Dye 86 | 0.27 | A | 9 hr | 3 | This invention |
| 187 | Dye 87 | 0.33 | AA | 9 hr | 3 | This invention |
| 188 | Dye 88 | 0.37 | AA | 9 hr | 3 | This invention |
| 189 | Dye 89 | 0.4 | AA | 9 hr | 3 | This invention |
| 190 | Dye 90 | 0.43 | AA | 15 hr | 4 | This invention |
| 191 | Dye 91 | 0.47 | AA | 15 hr | 4 | This invention |
| 192 | Dye 92 | 0.5 | AA | 15 hr | 5 | This invention |
| 193 | Dye 93 | 0.53 | AA | 15 hr | 5 | This invention |
| 194 | Dye 94 | 0.67 | AA | 15 hr | 5 | This invention |
| 195 | Dye 95 | 0.7 | AA | 18 hr | 5 | This invention |
| 196 | Dye 96 | 0.73 | AA | 18 hr | 8 | This invention |
| 197 | Dye 97 | 0.9 | AA | 18 hr | 14 | This invention |

TABLE 11-continued

| Solar cell No. | Metal complex dye | α | Turbidity | Adsorption time | Heat resistance 80° C. × 200 hr dark place decrease rate (%) | Remarks |
|---|---|---|---|---|---|---|
| 198 | Dye 98 | 0.1 | H | 18 hr | 5 | This invention |
| 199 | Dye 99 | 0.17 | G | 18 hr | 5 | This invention |
| 200 | Dye 100 | 0.2 | F | 15 hr | 5 | This invention |

TABLE 12

| Solar cell No. | Metal complex dye | α | Turbidity | Adsorption time | Heat resistance 80° C. × 200 hr dark place decrease rate (%) | Remarks |
|---|---|---|---|---|---|---|
| 201 | Dye 101 | 0.23 | E | 12 hr | 5 | This invention |
| 202 | Dye 102 | 0.27 | D | 6 hr | 5 | This invention |
| 203 | Dye 103 | 0.33 | D | 6 hr | 5 | This invention |
| 204 | Dye 104 | 0.37 | D | 6 hr | 5 | This invention |
| 205 | Dye 105 | 0.4 | D | 9 hr | 6 | This invention |
| 206 | Dye 106 | 0.43 | D | 15 hr | 6 | This invention |
| 207 | Dye 107 | 0.47 | D | 15 hr | 6 | This invention |
| 208 | Dye 108 | 0.5 | D | 15 hr | 7 | This invention |
| 209 | Dye 109 | 0.53 | C | 15 hr | 7 | This invention |
| 210 | Dye 110 | 0.67 | B | 15 hr | 7 | This invention |
| 211 | Dye 111 | 0.7 | A | 18 hr | 8 | This invention |
| 212 | Dye 112 | 0.73 | A | 18 hr | 8 | This invention |
| 213 | Dye 113 | 0.9 | A | 18 hr | 12 | This invention |
| 214 | Dye 114 | 0.1 | H | 18 hr | 5 | This invention |
| 215 | Dye 115 | 0.13 | G | 18 hr | 5 | This invention |
| 216 | Dye 116 | 0.15 | F | 15 hr | 5 | This invention |
| 217 | Dye 117 | 0.18 | E | 15 hr | 5 | This invention |
| 218 | Dye 118 | 0.2 | D | 12 hr | 5 | This invention |
| 219 | Dye 119 | 0.23 | D | 12 hr | 5 | This invention |
| 220 | Dye 120 | 0.25 | D | 9 hr | 5 | This invention |
| 221 | Dye 121 | 0.3 | D | 9 hr | 5 | This invention |
| 222 | Dye 122 | 0.4 | D | 9 hr | 6 | This invention |
| 223 | Dye 123 | 0.43 | D | 12 hr | 6 | This invention |
| 224 | Dye 124 | 0.45 | D | 12 hr | 6 | This invention |
| 225 | Dye 125 | 0.5 | C | 15 hr | 7 | This invention |
| 226 | Dye 126 | 0.53 | B | 15 hr | 7 | This invention |
| 227 | Dye 127 | 0.55 | A | 18 hr | 8 | This invention |
| 228 | Dye 128 | 0.6 | A | 18 hr | 8 | This invention |
| 229 | Dye 129 | 0.9 | A | 18 hr | 12 | This invention |
| 230 | Dye 130 | 0.17 | B | 15 hr | 1 | This invention |
| 231 | Dye 131 | 0.23 | A | 9 hr | 1 | This invention |
| 232 | Dye 132 | 0.33 | AA | 6 hr | 1 | This invention |
| 233 | Dye 133 | 0.43 | AA | 9 hr | 2 | This invention |
| 234 | Dye 134 | 0.67 | AA | 12 hr | 3 | This invention |
| 235 | Dye 135 | 0.83 | AA | 15 hr | 6 | This invention |
| 236 | Dye 136 | 0.17 | B | 15 hr | 1 | This invention |
| 237 | Dye 137 | 0.23 | A | 9 hr | 1 | This invention |
| 238 | Dye 138 | 0.33 | AA | 6 hr | 1 | This invention |
| 239 | Dye 139 | 0.43 | AA | 9 hr | 2 | This invention |
| 240 | Dye 140 | 0.67 | AA | 12 hr | 3 | This invention |
| 241 | Dye 141 | 0.83 | AA | 15 hr | 7 | This invention |
| 242 | Dye 142 | 0.17 | B | 15 hr | 1 | This invention |
| 243 | Dye 143 | 0.23 | A | 9 hr | 1 | This invention |
| 244 | Dye 144 | 0.33 | AA | 6 hr | 1 | This invention |
| 245 | Dye 145 | 0.43 | AA | 9 hr | 2 | This invention |
| 246 | Dye 146 | 0.67 | AA | 12 hr | 3 | This invention |
| 247 | Dye 147 | 0.83 | AA | 15 hr | 6 | This invention |
| 248 | Dye 148 | 0.17 | B | 15 hr | 1 | This invention |
| 249 | Dye 149 | 0.23 | A | 9 hr | 1 | This invention |
| 250 | Dye 150 | 0.33 | AA | 6 hr | 1 | This invention |

TABLE 13

| Solar cell No. | Metal complex dye | α | Turbidity | Adsorption time | Heat resistance 80° C. × 200 hr dark place decrease rate (%) | Remarks |
|---|---|---|---|---|---|---|
| 251 | Dye 151 | 0.43 | AA | 9 hr | 2 | This invention |
| 252 | Dye 152 | 0.67 | AA | 12 hr | 3 | This invention |
| 253 | Dye 153 | 0.83 | AA | 15 hr | 6 | This invention |
| 254 | Dye 154 | 0.17 | B | 15 hr | 1 | This invention |
| 255 | Dye 155 | 0.23 | A | 9 hr | 1 | This invention |
| 256 | Dye 156 | 0.33 | AA | 6 hr | 1 | This invention |
| 257 | Dye 157 | 0.43 | AA | 9 hr | 2 | This invention |
| 258 | Dye 158 | 0.67 | AA | 12 hr | 3 | This invention |
| 259 | Dye 159 | 0.83 | AA | 15 hr | 6 | This invention |

TABLE 13-continued

| Solar cell No. | Metal complex dye | α | Turbidity | Adsorption time | Heat resistance 80° C. × 200 hr dark place decrease rate (%) | Remarks |
|---|---|---|---|---|---|---|
| 260 | Dye 160 | 0.17 | B | 15 hr | 1 | This invention |
| 261 | Dye 161 | 0.23 | A | 9 hr | 1 | This invention |
| 262 | Dye 162 | 0.33 | AA | 6 hr | 1 | This invention |
| 263 | Dye 163 | 0.43 | AA | 9 hr | 2 | This invention |
| 264 | Dye 164 | 0.67 | AA | 12 hr | 3 | This invention |
| 265 | Dye 165 | 0.83 | AA | 15 hr | 8 | This invention |
| 266 | Dye 166 | 0.17 | B | 15 hr | 1 | This invention |
| 267 | Dye 167 | 0.23 | A | 9 hr | 1 | This invention |
| 268 | Dye 168 | 0.33 | AA | 6 hr | 1 | This invention |
| 269 | Dye 169 | 0.43 | AA | 9 hr | 2 | This invention |
| 270 | Dye 170 | 0.67 | AA | 12 hr | 3 | This invention |
| 271 | Dye 171 | 0.83 | AA | 15 hr | 7 | This invention |
| 272 | Dye 172 | 0.17 | B | 15 hr | 1 | This invention |
| 273 | Dye 173 | 0.23 | A | 9 hr | 1 | This invention |
| 274 | Dye 174 | 0.33 | AA | 6 hr | 1 | This invention |
| 275 | Dye 175 | 0.43 | AA | 9 hr | 2 | This invention |
| 276 | Dye 176 | 0.67 | AA | 12 hr | 3 | This invention |
| 277 | Dye 177 | 0.83 | AA | 15 hr | 7 | This invention |
| 278 | Dye 178 | 0.17 | B | 15 hr | 1 | This invention |
| 279 | Dye 179 | 0.23 | A | 9 hr | 1 | This invention |
| 280 | Dye 180 | 0.33 | AA | 6 hr | 1 | This invention |
| 281 | Dye 181 | 0.43 | AA | 9 hr | 2 | This invention |
| 282 | Dye 182 | 0.67 | AA | 12 hr | 3 | This invention |
| 283 | Dye 183 | 0.83 | AA | 15 hr | 8 | This invention |
| 284 | Dye 184 | 0.17 | C | 18 hr | 2 | This invention |
| 285 | Dye 185 | 0.23 | B | 12 hr | 2 | This invention |
| 286 | Dye 186 | 0.33 | A | 9 hr | 2 | This invention |
| 287 | Dye 187 | 0.43 | AA | 12 hr | 3 | This invention |
| 288 | Dye 188 | 0.67 | AA | 15 hr | 4 | This invention |
| 289 | Dye 189 | 0.83 | AA | 18 hr | 8 | This invention |
| 290 | Dye 190 | 0.17 | C | 18 hr | 2 | This invention |
| 291 | Dye 191 | 0.23 | B | 12 hr | 2 | This invention |
| 292 | Dye 192 | 0.33 | A | 9 hr | 2 | This invention |
| 293 | Dye 193 | 0.43 | AA | 12 hr | 3 | This invention |
| 294 | Dye 194 | 0.67 | AA | 15 hr | 4 | This invention |
| 295 | Dye 195 | 0.83 | AA | 18 hr | 7 | This invention |
| 296 | Dye 196 | 0.17 | C | 18 hr | 2 | This invention |
| 297 | Dye 197 | 0.23 | B | 12 hr | 2 | This invention |
| 298 | Dye 198 | 0.33 | A | 9 hr | 2 | This invention |
| 299 | Dye 199 | 0.43 | AA | 12 hr | 3 | This invention |
| 300 | Dye 200 | 0.67 | AA | 15 hr | 4 | This invention |

TABLE 14

| Solar cell No. | Metal complex dye | α | Turbidity | Adsorption time | Heat resistance 80° C. × 200 hr dark place decrease rate (%) | Remarks |
|---|---|---|---|---|---|---|
| 301 | Dye 201 | 0.83 | AA | 18 hr | 6 | This invention |
| 302 | Dye 202 | 0.17 | C | 18 hr | 2 | This invention |
| 303 | Dye 203 | 0.23 | B | 12 hr | 2 | This invention |
| 304 | Dye 204 | 0.33 | A | 9 hr | 2 | This invention |
| 305 | Dye 205 | 0.43 | AA | 12 hr | 3 | This invention |
| 306 | Dye 206 | 0.67 | AA | 15 hr | 4 | This invention |
| 307 | Dye 207 | 0.83 | AA | 18 hr | 8 | This invention |
| 308 | Dye 208 | 0.17 | C | 18 hr | 2 | This invention |
| 309 | Dye 209 | 0.23 | B | 12 hr | 2 | This invention |
| 310 | Dye 210 | 0.33 | A | 9 hr | 2 | This invention |
| 311 | Dye 211 | 0.43 | AA | 12 hr | 3 | This invention |
| 312 | Dye 212 | 0.67 | AA | 15 hr | 4 | This invention |
| 313 | Dye 213 | 0.83 | AA | 18 hr | 7 | This invention |
| 314 | Dye 214 | 0.17 | C | 18 hr | 2 | This invention |
| 315 | Dye 215 | 0.23 | B | 12 hr | 2 | This invention |
| 316 | Dye 216 | 0.33 | A | 9 hr | 2 | This invention |
| 317 | Dye 217 | 0.43 | AA | 12 hr | 3 | This invention |
| 318 | Dye 218 | 0.67 | AA | 15 hr | 4 | This invention |
| 319 | Dye 219 | 0.83 | AA | 18 hr | 5 | This invention |
| 320 | Dye 220 | 0.17 | C | 18 hr | 2 | This invention |
| 321 | Dye 221 | 0.23 | B | 12 hr | 2 | This invention |
| 322 | Dye 222 | 0.33 | A | 9 hr | 2 | This invention |
| 323 | Dye 223 | 0.43 | AA | 12 hr | 3 | This invention |
| 324 | Dye 224 | 0.67 | AA | 15 hr | 4 | This invention |
| 325 | Dye 225 | 0.83 | AA | 18 hr | 7 | This invention |
| 326 | Dye 226 | 0.17 | C | 18 hr | 2 | This invention |
| 327 | Dye 227 | 0.23 | B | 12 hr | 2 | This invention |

TABLE 14-continued

| Solar cell No. | Metal complex dye | α | Turbidity | Adsorption time | Heat resistance 80° C. × 200 hr dark place decrease rate (%) | Remarks |
|---|---|---|---|---|---|---|
| 328 | Dye 228 | 0.33 | A | 9 hr | 2 | This invention |
| 329 | Dye 229 | 0.43 | AA | 12 hr | 3 | This invention |
| 330 | Dye 230 | 0.67 | AA | 15 hr | 4 | This invention |
| 331 | Dye 231 | 0.83 | AA | 18 hr | 8 | This invention |
| 332 | Dye 232 | 0.17 | D | 18 hr | 3 | This invention |
| 333 | Dye 233 | 0.23 | C | 12 hr | 3 | This invention |
| 334 | Dye 234 | 0.33 | B | 9 hr | 3 | This invention |
| 335 | Dye 235 | 0.43 | A | 12 hr | 4 | This invention |
| 336 | Dye 236 | 0.67 | AA | 15 hr | 5 | This invention |
| 337 | Dye 237 | 0.83 | AA | 18 hr | 8 | This invention |
| 338 | Dye 238 | 0.17 | D | 18 hr | 3 | This invention |
| 339 | Dye 239 | 0.23 | C | 12 hr | 3 | This invention |
| 340 | Dye 240 | 0.33 | B | 9 hr | 3 | This invention |
| 341 | Dye 241 | 0.43 | A | 12 hr | 4 | This invention |
| 342 | Dye 242 | 0.67 | AA | 15 hr | 5 | This invention |
| 343 | Dye 243 | 0.83 | AA | 18 hr | 8 | This invention |
| 344 | Dye 244 | 0.17 | D | 18 hr | 3 | This invention |
| 345 | Dye 245 | 0.23 | C | 12 hr | 3 | This invention |
| 346 | Dye 246 | 0.33 | B | 9 hr | 3 | This invention |
| 347 | Dye 247 | 0.43 | A | 12 hr | 4 | This invention |
| 348 | Dye 248 | 0.67 | AA | 15 hr | 5 | This invention |
| 349 | Dye 249 | 0.83 | AA | 18 hr | 7 | This invention |
| 350 | Dye 250 | 0.17 | D | 18 hr | 3 | This invention |

TABLE 15

| Solar cell No. | Metal complex dye | α | Turbidity | Adsorption time | Heat resistance 80° C. × 200 hr dark place decrease rate (%) | Remarks |
|---|---|---|---|---|---|---|
| 351 | Dye 251 | 0.23 | C | 12 hr | 3 | This invention |
| 352 | Dye 252 | 0.33 | B | 9 hr | 3 | This invention |
| 353 | Dye 253 | 0.43 | A | 12 hr | 4 | This invention |
| 354 | Dye 254 | 0.67 | AA | 15 hr | 5 | This invention |
| 355 | Dye 255 | 0.83 | AA | 18 hr | 7 | This invention |
| 356 | Dye 256 | 0.17 | D | 18 hr | 3 | This invention |
| 357 | Dye 257 | 0.23 | C | 12 hr | 3 | This invention |
| 358 | Dye 258 | 0.33 | B | 9 hr | 3 | This invention |
| 359 | Dye 259 | 0.43 | A | 12 hr | 4 | This invention |
| 360 | Dye 260 | 0.67 | AA | 15 hr | 5 | This invention |
| 361 | Dye 261 | 0.83 | AA | 18 hr | 6 | This invention |
| 362 | Dye 262 | 0.17 | D | 18 hr | 3 | This invention |
| 363 | Dye 263 | 0.23 | C | 12 hr | 3 | This invention |
| 364 | Dye 264 | 0.33 | B | 9 hr | 3 | This invention |
| 365 | Dye 265 | 0.43 | A | 12 hr | 4 | This invention |
| 366 | Dye 266 | 0.67 | AA | 15 hr | 5 | This invention |
| 367 | Dye 267 | 0.83 | AA | 18 hr | 8 | This invention |
| 368 | Dye 268 | 0.17 | E | 18 hr | 4 | This invention |
| 369 | Dye 269 | 0.23 | D | 18 hr | 4 | This invention |
| 370 | Dye 270 | 0.33 | C | 9 hr | 4 | This invention |
| 371 | Dye 271 | 0.43 | B | 12 hr | 5 | This invention |
| 372 | Dye 272 | 0.67 | A | 15 hr | 6 | This invention |
| 373 | Dye 273 | 0.83 | AA | 18 hr | 7 | This invention |
| 374 | Dye 274 | 0.33 | B | 9 hr | 2 | This invention |
| 375 | Dye 275 | 0.33 | A | 9 hr | 2 | This invention |
| 376 | Dye 276 | 0.33 | B | 9 hr | 2 | This invention |
| 377 | Dye 277 | 0.33 | A | 9 hr | 2 | This invention |
| 378 | Dye 278 | 0.33 | B | 9 hr | 2 | This invention |
| 379 | Dye 279 | 0.33 | A | 9 hr | 2 | This invention |
| 380 | Dye 280 | 0.33 | B | 9 hr | 2 | This invention |
| 381 | Dye 281 | 0.33 | A | 9 hr | 2 | This invention |
| 382 | Dye 282 | 0.33 | B | 9 hr | 2 | This invention |
| 383 | Dye 283 | 0.33 | A | 9 hr | 2 | This invention |
| 384 | Dye 284 | 0.33 | B | 9 hr | 2 | This invention |
| 385 | Dye 285 | 0.33 | A | 9 hr | 2 | This invention |
| 386 | Dye 288 | 0.33 | B | 9 hr | 2 | This invention |
| 387 | Dye 289 | 0.33 | A | 9 hr | 2 | This invention |
| 388 | Dye 290 | 0.33 | B | 9 hr | 2 | This invention |
| 389 | Dye 291 | 0.33 | A | 9 hr | 2 | This invention |
| 390 | Dye 292 | 0.33 | B | 9 hr | 2 | This invention |
| 391 | Dye 293 | 0.33 | A | 9 hr | 2 | This invention |
| 392 | Dye 294 | 0.33 | B | 9 hr | 2 | This invention |
| 393 | Dye 295 | 0.33 | A | 9 hr | 2 | This invention |
| 394 | Dye 298 | 0.33 | C | 9 hr | 4 | This invention |
| 395 | Dye 299 | 0.33 | B | 12 hr | 3 | This invention |

TABLE 15-continued

| Solar cell No. | Metal complex dye | α | Turbidity | Adsorption time | Heat resistance 80° C. × 200 hr dark place decrease rate (%) | Remarks |
|---|---|---|---|---|---|---|
| 396 | Dye 300 | 0.33 | C | 9 hr | 4 | This invention |
| 397 | Dye 301 | 0.33 | B | 12 hr | 3 | This invention |
| 398 | Dye 302 | 0.33 | C | 9 hr | 4 | This invention |
| 399 | Dye 303 | 0.33 | B | 12 hr | 3 | This invention |
| 400 | Dye 304 | 0.33 | C | 9 hr | 4 | This invention |

TABLE 16

| Solar cell No. | Metal complex dye | α | Turbidity | Adsorption time | Heat resistance 80° C. × 200 hr dark place decrease rate (%) | Remarks |
|---|---|---|---|---|---|---|
| 401 | Dye 305 | 0.33 | B | 12 hr | 3 | This invention |
| 402 | Dye 306 | 0.33 | C | 9 hr | 4 | This invention |
| 403 | Dye 307 | 0.33 | B | 12 hr | 3 | This invention |
| 404 | Dye 308 | 0.33 | C | 9 hr | 4 | This invention |
| 405 | Dye 309 | 0.33 | B | 12 hr | 3 | This invention |
| 406 | Dye 310 | 0.33 | C | 9 hr | 4 | This invention |
| 407 | Dye 311 | 0.33 | B | 12 hr | 3 | This invention |
| 408 | Dye 312 | 0.33 | C | 9 hr | 4 | This invention |
| 409 | Dye 313 | 0.33 | B | 12 hr | 3 | This invention |
| 410 | Dye 314 | 0.33 | D | 9 hr | 4 | This invention |
| 411 | Dye 315 | 0.33 | C | 12 hr | 3 | This invention |
| 412 | Dye 316 | 0.33 | D | 9 hr | 4 | This invention |
| 413 | Dye 317 | 0.33 | C | 12 hr | 3 | This invention |
| 414 | Dye 318 | 0.33 | D | 9 hr | 4 | This invention |
| 415 | Dye 319 | 0.33 | C | 12 hr | 3 | This invention |
| 416 | Dye 320 | 0.33 | D | 9 hr | 4 | This invention |
| 417 | Dye 321 | 0.33 | C | 12 hr | 3 | This invention |
| 418 | Dye 322 | 0.33 | D | 9 hr | 4 | This invention |
| 419 | Dye 323 | 0.33 | C | 12 hr | 3 | This invention |
| 420 | Dye 324 | 0.33 | D | 9 hr | 4 | This invention |
| 421 | Dye 325 | 0.33 | C | 12 hr | 3 | This invention |
| 422 | Dye 326 | 0.33 | E | 12 hr | 5 | This invention |
| 423 | Dye 327 | 0.33 | D | 12 hr | 4 | This invention |
| 424 | Dye 328 | 0.33 | F | 12 hr | 5 | This invention |
| 425 | Dye 329 | 0.33 | E | 12 hr | 4 | This invention |
| 426 | Dye 330 | 0.5 | F | 12 hr | 6 | This invention |
| 427 | Dye 331 | 0.5 | E | 12 hr | 6 | This invention |
| 428 | Dye 336 | 0.33 | H | 12 hr | 8 | This invention |
| 429 | Dye 337 | 0.33 | G | 12 hr | 9 | This invention |

TABLE 17

| Solar cell No. | Metal complex dye | α | Turbidity | Adsorption time | Heat resistance 80° C. × 200 hr dark place decrease rate (%) | Remarks |
|---|---|---|---|---|---|---|
| C01 | C-Dye c1 | 0 | M | x | 17 | C Ex |
| C02 | C-Dye c2 | 0.07 | K | 21 hr | 16 | C Ex |
| C03 | C-Dye c3 | 0.93 | AA | x | 30 | C Ex |
| C04 | C-Dye c4 | 1 | AA | x | 68 | C Ex |
| C05 | C-Dye c5 | 0 | M | x | 18 | C Ex |
| C06 | C-Dye c6 | 0.05 | K | 21 hr | 15 | C Ex |
| C07 | C-Dye c7 | 0.95 | AA | x | 28 | C Ex |
| C08 | C-Dye c8 | 1 | AA | x | 64 | C Ex |
| C09 | C-Dye c9 | 0 | M | x | 19 | C Ex |
| C10 | C-Dye c10 | 0.07 | K | x | 16 | C Ex |
| C11 | C-Dye c11 | 0.93 | AA | 21 hr | 27 | C Ex |
| C12 | C-Dye c12 | 1 | AA | x | 60 | C Ex |
| C13 | C-Dye c13 | 0 | M | x | 20 | C Ex |
| C14 | C-Dye c14 | 0.07 | K | x | 18 | C Ex |
| C15 | C-Dye c15 | 0.33 | K | 21 hr | 19 | C Ex |
| C16 | C-Dye c16 | 0.5 | F | 21 hr | 21 | C Ex |
| C17 | C-Dye c17 | 0.67 | B | x | 23 | C Ex |
| C18 | C-Dye c18 | 0.93 | AA | 21 hr | 32 | C Ex |
| C19 | C-Dye c19 | 1 | AA | x | 70 | C Ex |
| C20 | C-Dye c20 | 0.07 | K | x | 16 | C Ex |
| C21 | C-Dye c21 | 0.93 | AA | 21 hr | 29 | C Ex |
| C22 | C-Dye c22 | 1 | AA | x | 64 | C Ex |
| C23 | C-Dye c23 | 0.07 | L | x | 19 | C Ex |
| C24 | C-Dye c24 | 0.93 | AA | 21 hr | 33 | C Ex |
| C25 | C-Dye c25 | 1 | AA | x | 69 | C Ex |
| C26 | C-Dye c26 | 0.07 | K | x | 17 | C Ex |
| C27 | C-Dye c27 | 0.93 | A | 21 hr | 29 | C Ex |
| C28 | C-Dye c28 | 1 | AA | x | 67 | C Ex |
| C29 | C-Dye c29 | 0.07 | L | x | 16 | C Ex |
| C30 | C-Dye c30 | 0.33 | K | 21 hr | 19 | C Ex |
| C31 | C-Dye c31 | 0.5 | E | 21 hr | 22 | C Ex |
| C32 | C-Dye c32 | 0.67 | A | 21 hr | 30 | C Ex |
| C33 | C-Dye c33 | 0.93 | A | 21 hr | 32 | C Ex |
| C34 | C-Dye c34 | 1 | AA | x | 72 | C Ex |
| C35 | C-Dye c35 | 0.5 | A | 18 hr | 31 | C Ex |
| C36 | C-Dye c36 | 0.67 | A | 21 hr | 32 | C Ex |
| C37 | C-Dye c37 | 0 | M | x | 19 | C Ex |
| C38 | C-Dye c38 | 0.25 | K | x | 18 | C Ex |
| C39 | C-Dye c39 | 0.5 | G | 18 hr | 16 | C Ex |
| C40 | C-Dye c40 | 0.75 | D | x | 22 | C Ex |
| C41 | C-Dye c41 | 1 | C | x | 68 | C Ex |
| C42 | C-Dye c42 | 0.25 | M | x | 21 | C Ex |
| C43 | C-Dye c43 | 0.5 | I | x | 19 | C Ex |
| C44 | C-Dye c44 | 0.75 | F | 21 hr | 28 | C Ex |
| C45 | C-Dye c45 | 1 | A | x | 75 | C Ex |
| C46 | C-Dye c46 | 0 | M | x | 37 | C Ex |
| C47 | C-Dye c47 | 0.33 | L | 21 hr | 32 | C Ex |
| C48 | C-Dye c48 | 1 | AA | x | 85 | C Ex |
| C49 | C-Dye c49 | 0 | M | 21 hr | 32 | C Ex |
| C50 | C-Dye c50 | 1 | A | x | 61 | C Ex |

"C-Dye" means Comparative Dye, and "C Ex" means Comparative Example.

The time of 18 hours or less in terms of the adsorption time and the decrease rate of 15% or less in the heat resistance test are each a level for passing the evaluation criteria. Fulfillment of both requirements results in achievement of a goal.

As is apparent from the above tables, in the metal complex dye of the present invention in which a ratio (number of salt of carboxyl group/total number of carboxyl group and salt of carboxyl group) a of the number of a salt of the carboxyl group to the total number of the carboxyl group and the salt of the carboxyl group to be found in 1 mole of the metal complex dye, lies in the range of 0.1 to 0.9, the results of the adsorption time and the heat resistance test go together. It is found that a is preferably 0.1 to 0.7, more preferably 0.2 to 0.5, and most preferably 0.25 to 0.4. Further, as regards the kind of the salt, lithium, potassium and cesium used in the present invention fulfill both requirements of the adsorption time and the heat resistance test. However, even though sodium and quaternary ammonium which are out of the present invention fulfill the range of a, such effects as the present invention were not obtained. Note that as regards the kind of the salt, potassium was preferred among lithium, potassium and cesium.

Having described our invention as related to the present embodiments, it is our intention that the invention not be limited by any of the details of the description, unless otherwise specified, but rather be construed broadly within its spirit and scope as set out in the accompanying claims.

REFERENCE SIGNS LIST

1 Electrically-conductive support
2 Photoconductor layer
21 Dye
22 Semiconductor fine-particle
3 Charge-transfer layer
4 Counter electrode
5 Light-receiving electrode
6 Circuit
10 Photoelectric conversion element
100 System using dye-sensitized solar cell
M Electric motor (electric fan)
20 Dye-sensitized solar cell
40 Photoelectrode
41 Transparent electrode
42 Semiconductor electrode
43 Transparent electrically-conductive film
44 Substrate
45 Semiconductor layer
46 Light-scattering layer
CE Counter electrode
E Electrolyte
S Spacer

The invention claimed is:
1. A photoelectric conversion element comprising an electrically conductive support, a photoconductor layer containing an electrolyte, a charge transfer layer containing an electrolyte, and a counter electrode,
wherein the photoconductor layer contains semiconductor fine particles carrying a metal complex dye represented by the following Formula (I); and
wherein the metal complex dye has at least a carboxyl group and a salt of the carboxyl group, the salt being selected from the group consisting of a potassium salt, a lithium salt, and a cesium salt, and the ratio α defined by the expression: (number of the salt of the carboxyl group)/(the total number of the carboxyl group and the salt of the carboxyl group) to be found in one molecule of the metal complex dye, lying in the range of 0.1 to 0.9:

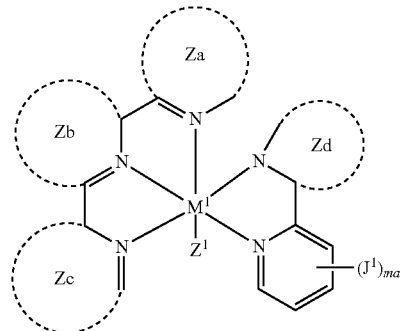

Formula (I)

wherein, in Formula (I), $M^1$ represents a Ru atom or an Os atom; $Z^1$ represents a monodentate ligand; the rings Za, Zb and Zc each independently represent a group of nonmetallic atoms necessary for forming a nitrogen-containing 5- or 6-membered ring, provided that at least two rings among the rings formed by Za, Zb and Zc each contain a carboxyl group, or a potassium salt, a lithium salt or a cesium salt of a carboxyl group; the ring Zd represents a group represented by any one of the following Formulas (Zd-1) to (Zd-5); $J^1$ represents a substituent; and ma represents an integer of 0 to 2;

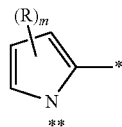

Formula (Zd-1)

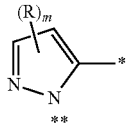

Formula (Zd-2)

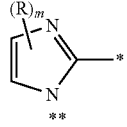

Formula (Zd-3)

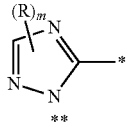

Formula (Zd-4)

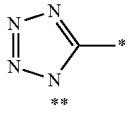

Formula (Zd-5)

wherein, in Formulas (Zd-1) to (Zd-5), R represents an alkyl group which may be substituted with a halogen atom, an aromatic group, or a heterocyclic group; m represents an integer of 0 or more; the symbol "*" represents a binding site with the pyridine ring having $J^1$; and the symbol "**" represents an atom or an atom anion coordinated with $M^1$, and
wherein the substituent represented by $J^1$ is selected from the group consisting of an alkyl group having 1 to 20 carbon atoms, an alkenyl group having 2 to 20 carbon atoms, an alkynyl group having 2 to 20 carbon atoms, a cycloalkyl group having 3 to 20 carbon atoms, a cycloalkenyl group having 5 to 20 carbon atoms, an aryl group having 6 to 26 carbon atoms, a heterocyclic group having 2 to 20 carbon atoms and at least one oxygen atom, sulfur atom, or nitrogen atom, an alkoxy group having 1 to 20 carbon atoms, an alkenyloxy group having 2 to 20 carbon atoms, an alkynyloxy group having 2 to 20 carbon atoms, a cycloalkyloxy group having 3 to 20 carbon atoms, an aryloxy group having 6 to 26 carbon atoms, a heterocyclic oxy group, an alkoxycarbonyl group having 2 to 20 carbon atoms, a cycloalkoxycarbonyl group having 4 to 20 carbon atoms, an aryloxycarbonyl group having 6 to 20 carbon atoms, an amino group having 0 to 20 carbon atoms, a sulfamoyl group having 0 to 20 carbon atoms, an acyl group having 1 to 20 carbon atoms, an acyloxy group having 1 to 20 carbon atoms, a carbamoyl group having 1 to 20 carbon atoms, an acylamino group having 1 to 20 carbon atoms, a sulfonamide group having 0 to 20 carbon atoms, an alkylthio group having 1 to 20 carbon atoms, a cycloalkylthio group having 3 to 20 carbon atoms, an arylthio group having 6 to 26 carbon atoms, an alkyl-, cycloalkyl- or aryl-sulfonyl group having 1 to 20 carbon atoms, a silyl group having 1 to 20 carbon atoms, a silyloxy group having 1 to 20 carbon atoms, a hydroxyl group, a cyano group, a nitro group, a halogen atom, a carboxyl group, a sulfo group, a phosphonyl group, a phosphoryl group and a boric-acid group.

2. The photoelectric conversion element according to claim 1, wherein, in Formula (I), when any two of rings formed as the ring Za, the ring Zb and the ring Zc have the carboxyl group, or the potassium salt, the lithium salt or the cesium salt of the carboxyl group, the ratio α is 0.15 to 0.55, and when all of rings formed as the ring Za, the ring Zb and the ring Zc have the carboxyl group, or the potassium salt, the lithium salt or the cesium salt of the carboxyl group, the ratio α is 0.1 to 0.7.

3. The photoelectric conversion element according to claim 1, wherein, in Formula (I), all of the rings formed as the ring Za, the ring Zb and the ring Zc have a carboxyl group, or a potassium salt, a lithium salt or a cesium salt of a carboxyl group; and the ratio α is 0.1 to 0.7.

4. The photoelectric conversion element according to claim 1, wherein the ratio α is 0.2 to 0.5.

5. The photoelectric conversion element according to claim 1, wherein the ratio α is 0.25 to 0.4.

6. The photoelectric conversion element according to claim 1, wherein the metal complex dye is represented by the following Formula (I-1):

Formula (I-1)

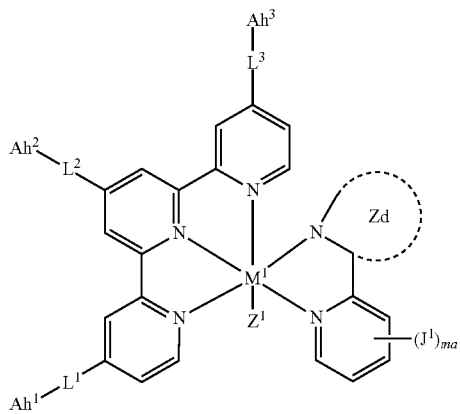

wherein, in Formula (I-1), the ring Zd, $M^1$, $Z^1$, $J^1$ and ma have the same meaning as the ring Zd, $M^1$, $Z^1$, $J^1$ and ma in Formula (I); $L^1$ to $L^3$ each independently represent a single bond or a divalent linking group; $Ah^1$ to $Ah^3$ each independently represent a hydrogen atom, a carboxyl group, or a potassium salt, a lithium salt or a cesium salt of a carboxyl group; and at least two of $Ah^1$ to $Ah^3$ are a carboxyl group, or a potassium salt, a lithium salt or a cesium salt of a carboxyl group.

7. The photoelectric conversion element according to claim 1, wherein the metal complex dye is represented by the following Formula (I-2):

Formula (I-2)

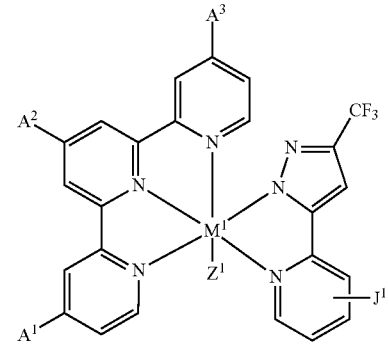

wherein, in Formula (I-2), $M^1$, $Z^1$ and $J^1$ have the same meaning as $M^1$, $Z^1$ and $J^1$ in Formula (I-1); and $A^1$ to $A^3$ each independently represent a carboxyl group, or a potassium salt, a lithium salt or a cesium salt of a carboxyl group.

8. The photoelectric conversion element according to claim 1, wherein the metal complex dye is represented by any one of the following Formulas (I-3A) to (I-3C):

Formula (I-3A)

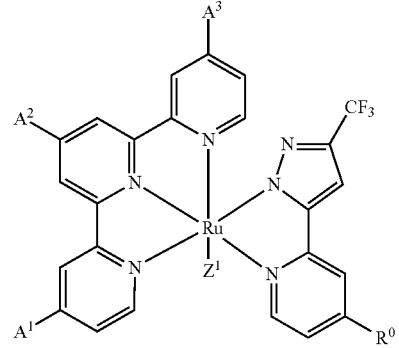

Formula (I-3B)

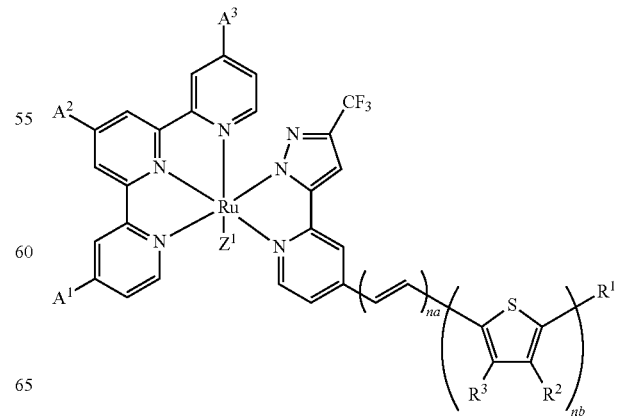

115

-continued

Formula (I-3C)

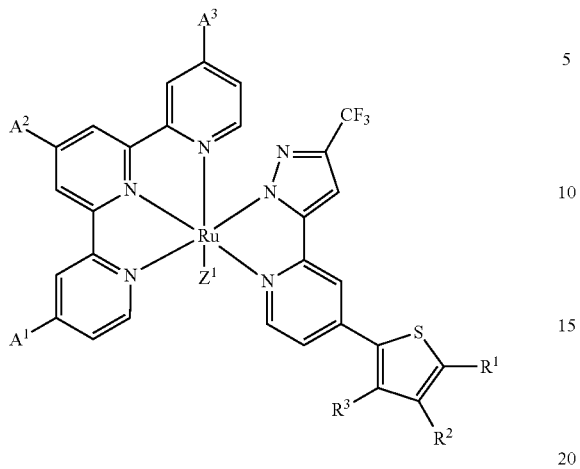

wherein, in Formulas (I-3A) to (I-3C), $Z^1$ has the same meaning as $Z^1$ in Formula (I); $A^1$ to $A^3$ each independently represent a carboxyl group, or a potassium salt, a lithium salt or a cesium salt of a carboxyl group; $R^0$ represents a hydrogen atom; $R^1$ represents a hydrogen atom, an alkyl group, an alkynyl group, an alkenyl group, an alkylthio group, an amino group or a heterocyclic group; $R^2$ and $R^3$ each independently represent a hydrogen atom, an alkyl group, an alkoxy group or a heterocyclic group; and na and nb each independently represent an integer of 0 or more, provided that the sum of na and nb is 2 or more.

9. The photoelectric conversion element according to claim 8, wherein, in Formula (I-3B), $R^1$ is an alkyl group, an alkynyl group, an amino group or an alkylthio group, and $R^2$ and $R^3$ each independently are a hydrogen atom or an alkoxy group.

10. The photoelectric conversion element according to claim 8, wherein, in Formula (I-3C), $R^1$ is an alkyl group, an alkynyl group or a heterocyclic group, and $R^2$ and $R^3$ are a hydrogen atom; or wherein, in Formula (I-3C), $R^1$ and $R^2$ are a hydrogen atom, and $R^3$ is an alkyl group.

11. A photoelectric conversion element comprising an electrically conductive support, a photoconductor layer containing an electrolyte, a charge transfer layer containing an electrolyte, and a counter electrode, wherein the photoconductor layer contains semiconductor fine particles carrying a metal complex dye represented by the following Formula (IA):

Formula (IA)

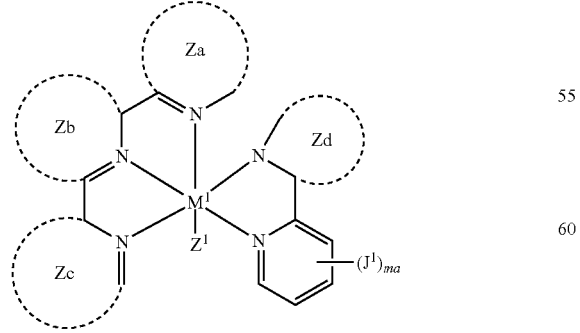

wherein, in Formula (IA), $M^1$ represents a Ru atom or an Os atom; $Z^1$ represents a monodentate ligand; the rings Za, Zb and Zc each independently represent a group of nonmetallic atoms necessary for forming a nitrogen-containing 5- or 6-membered ring, provided that at least two of rings formed as the rings Za, Zb and Zc have a carboxyl group, or a potassium salt, a lithium salt or a cesium salt of the carboxyl group, at least one thereof being the carboxyl group, and at least one of the remainder being the potassium salt, the lithium salt or the cesium salt of the carboxyl group; the ring Zd represents a group represented by any one of the following Formulas (Zd-1) to (Zd-5); $J^1$ represents a substituent; and ma represents an integer of 0 to 2;

Formula (Zd-1)

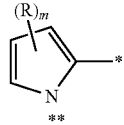

Formula (Zd-2)

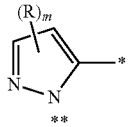

Formula (Zd-3)

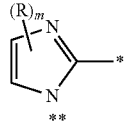

Formula (Zd-4)

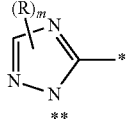

Formula (Zd-5)

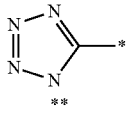

wherein, in Formulas (Zd-1) to (Zd-5), R represents an alkyl group which may be substituted with a halogen atom, an aromatic group, or a heterocyclic group; m represents an integer of 0 or more; the symbol "*" represents a binding site with the pyridine ring having $J^1$; and the symbol "**" represents an atom or an atom anion coordinated with $M^1$, and wherein the substituent represented by $J^1$ is selected from the group consisting of an alkyl group having 1 to 20 carbon atoms, an alkenyl group having 2 to 20 carbon atoms, an alkynyl group having 2 to 20 carbon atoms, a cycloalkyl group having 3 to 20 carbon atoms, a cycloalkenyl group having 5 to 20 carbon atoms, an aryl group having 6 to 26 carbon atoms, a heterocyclic group having 2 to 20 carbon atoms and at least one oxygen atom, sulfur atom, or nitrogen atom, an alkoxy group having 1 to 20 carbon atoms, an alkenyloxy group having 2 to 20 carbon atoms, an alkynyloxy group having 2 to 20 carbon atoms, a cycloalkyloxy group having 3 to 20 carbon atoms, an aryloxy group having 6 to 26 carbon atoms, a heterocyclic oxy group, an alkoxycarbonyl group having 2 to 20 carbon atoms, a cycloalkoxycarbonyl group having 4 to 20 carbon atoms, an aryloxycarbonyl group having 6 to 20 carbon atoms, an amino group having 0 to 20 carbon atoms, a sulfamoyl group having 0 to 20 carbon atoms, an acyl group having 1 to 20 carbon atoms, an acyloxy group having 1 to 20 carbon atoms, a carbamoyl group having 1 to 20 carbon atoms, an acylamino group having 1 to 20 carbon atoms, a sulfonamide group having 0 to 20 carbon atoms, an alkylthio group having 1 to 20 carbon atoms, a cycloalkylthio group having 3 to 20 carbon atoms, an arylthio group having 6 to 26 carbon atoms, an alkyl-, cycloalkyl- or aryl-sulfonyl group having 1 to 20 carbon atoms, a silyl group having 1 to 20 carbon atoms, a silyloxy group having 1 to 20 carbon atoms, a hydroxyl group, a cyano group, a nitro group, a halogen atom, a carboxyl group, a sulfo group, a phosphonyl group, a phosphoryl group and a boric-acid group.

12. The photoelectric conversion element according to claim 11, wherein the metal complex dye represented by Formula (IA) is represented by the following Formula (IA-1):

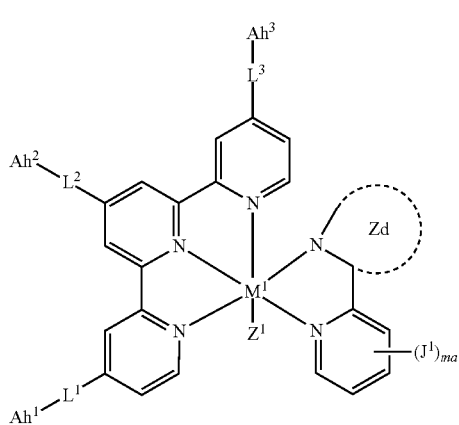

Formula (IA-1)

wherein, in Formula (IA-1), the ring Zd, $M^1$, $Z^1$, $J^1$ and ma have the same meaning as the ring Zd, $M^1$, $Z^1$, $J^1$ and ma in Formula (IA); $L^1$ to $L^3$ each independently represent a single bond or a divalent linking group; $Ah^1$ to $Ah^3$ each independently represent a hydrogen atom, a carboxyl group, or a potassium salt, a lithium salt or a cesium salt of a carboxyl group; and at least two of $Ah^1$ to $Ah^3$ are a carboxyl group, or a potassium salt, a lithium salt or a cesium salt of a carboxyl group.

13. The photoelectric conversion element according to claim 11, wherein the metal complex dye is represented by the following Formula (IA-2):

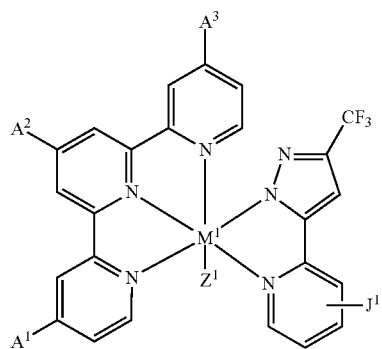

Formula (IA-2)

wherein, in Formula (IA-2), $M^1$, $Z^1$ and $J^1$ have the same meaning as $M^1$, $Z^1$ and $J^1$ in Formula (IA-1); $A^1$ to $A^3$ each independently represent a carboxyl group, or a potassium salt, a lithium salt or a cesium salt of a carboxyl group, provided that at least one of $A^1$ to $A^3$ represents a carboxyl group, and at least one of $A^1$ to $A^3$ represents a potassium salt, a lithium salt or a cesium salt of a carboxyl group.

14. The photoelectric conversion element according to claim 11, wherein the metal complex dye is represented by any one of the following Formulas (IA-3A) to (IA-3C):

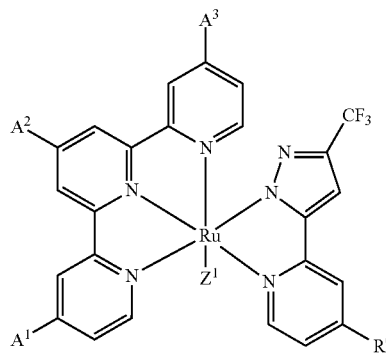

Formula (IA-3A)

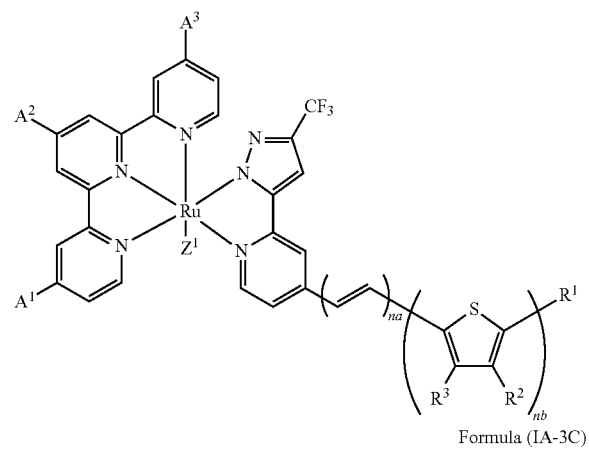

Formula (IA-3B)

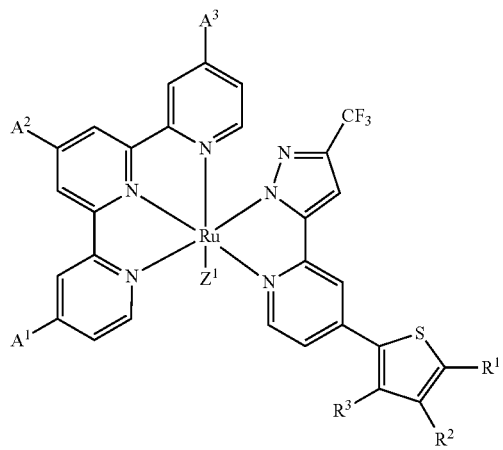

Formula (IA-3C)

wherein, in Formulas (IA-3A) to (IA-3C), $Z^1$ has the same meaning as $Z^1$ in Formula (IA); $A^1$ to $A^3$ each independently represent a carboxyl group, or a potassium salt, a lithium salt or a cesium salt of a carboxyl group, provided that at least one of $A^1$ to $A^3$ represents a carboxyl group, and at least one of $A^1$ to $A^3$ represents a potassium salt, a lithium salt or a cesium salt of a carboxyl group; $R^0$ represents a hydrogen atom; $R^1$ represents a hydrogen atom, an alkyl group, an alkynyl group, an alkenyl group, an alkylthio group, an amino group or a heterocyclic group; $R^2$ and $R^3$ each independently represent a hydrogen atom, an alkyl group, an alkoxy group or a heterocyclic group; and na and nb each independently represent an integer of 0 or more, provided that the sum of na and nb is 2 or more.

15. The photoelectric conversion element according to claim 14, wherein, in Formula (IA-3B), $R^1$ is an alkyl group, an alkynyl group, an amino group or an alkylthio group, and $R^2$ and $R^3$ each independently are a hydrogen atom or an alkoxy group.

16. The photoelectric conversion element according to claim 14, wherein, in Formula (IA-3C), $R^1$ is an alkyl group, an alkynyl group or a heterocyclic group, and $R^2$ and $R^3$ are a hydrogen atom; or wherein, in Formula (I-3C), $R^1$ and $R^2$ are a hydrogen atom, and $R^3$ is an alkyl group.

17. The photoelectric conversion element according to claim 13, wherein one of $A^1$ to $A^3$ is a carboxyl group, and the other two are a potassium salt, a lithium salt or a cesium salt of a carboxyl group.

18. The photoelectric conversion element according to claim 1, wherein the semiconductor fine particles are titanium oxide.

19. The photoelectric conversion element according to claim 1, wherein the salt of a carboxyl group is a potassium salt.

20. The photoelectric conversion element according to claim 11, wherein the salt of a carboxyl group is a potassium salt.

21. A dye-sensitized solar cell comprising the photoelectric conversion element according to claim 1.

22. A dye-sensitized solar cell comprising the photoelectric conversion element according to claim 11.

* * * * *